(12) United States Patent
Farritor et al.

(10) Patent No.: US 11,903,658 B2
(45) Date of Patent: Feb. 20, 2024

(54) ROBOTICALLY ASSISTED SURGICAL SYSTEM AND RELATED DEVICES AND METHODS

(71) Applicant: Virtual Incision Corporation, Lincoln, NE (US)

(72) Inventors: Shane Farritor, Lincoln, NE (US);
Nathan Wood, Lincoln, NE (US);
Jeffrey Shasho, Brooklyn, NY (US);
Dave Matsuura, Del Mar, CA (US);
Belinko Matsuura, Encinitas, CA (US);
Phil Simpson, Escondido, CA (US);
Alexander Rissler, Sexau (DE)

(73) Assignee: Virtual Incision Corporation, Lincoln, NE (US)

( * ) Notice: Subject to any disclaimer, the term of this patent is extended or adjusted under 35 U.S.C. 154(b) by 1020 days.

(21) Appl. No.: 16/736,329

(22) Filed: Jan. 7, 2020

(65) Prior Publication Data
US 2020/0214775 A1 Jul. 9, 2020

Related U.S. Application Data

(60) Provisional application No. 62/789,029, filed on Jan. 7, 2019.

(51) Int. Cl.
*A61B 1/00* (2006.01)
*A61B 34/30* (2016.01)
(Continued)

(52) U.S. Cl.
CPC .......... *A61B 34/30* (2016.02); *A61B 1/00057* (2013.01); *A61B 1/0057* (2013.01);
(Continued)

(58) Field of Classification Search
CPC ............ A61B 1/00057; A61B 1/00128; A61B 1/00149; A61B 1/0057; A61B 34/30; A61B 2017/00477
See application file for complete search history.

(56) References Cited

U.S. PATENT DOCUMENTS 2,858,947 A 11/1958 Chapman, Jr.
3,817,403 A 6/1974 Glachet et al.
(Continued)

FOREIGN PATENT DOCUMENTS

CA 2918531 A1 1/2015
CN 102499759 A 6/2012
(Continued)

OTHER PUBLICATIONS

Franzino, "The Laprotek Surgical System and the Next Generation of Robotics," Surg Clin North Am, 2003 83(6): 1317-1320.
(Continued)

*Primary Examiner* — Anh Tuan T Nguyen
*Assistant Examiner* — Rynae E Boler
(74) *Attorney, Agent, or Firm* — Fredrikson & Byron, P.A.

(57) ABSTRACT

Disclosed herein are various robotic surgical systems having various robotic devices. Further, disclosed herein are removable coupleable connection ports, each of which can be coupled to a robotic device and a camera assembly that is disposed into and through the robotic device. Also disclosed herein are removable connection ports having at least one of a elongate device body coupling mechanism, a camera assembly coupling mechanism, and/or a presence detection mechanism. Further discussed herein is a camera assembly with at least one actuation mechanism for actuating movement of the steerable distal tip thereof.

16 Claims, 24 Drawing Sheets

(51) Int. Cl.
*A61B 17/00* (2006.01)
*A61B 1/313* (2006.01)
*A61B 1/005* (2006.01)

(52) U.S. Cl.
CPC ...... *A61B 1/00128* (2013.01); *A61B 1/00149* (2013.01); *A61B 1/3132* (2013.01); *A61B 2017/00477* (2013.01)

(56) References Cited

U.S. PATENT DOCUMENTS

| | | |
|---|---|---|
| 3,870,264 A | 3/1975 | Robinson |
| 3,922,930 A | 12/1975 | Fletcher et al. |
| 3,971,266 A | 7/1976 | Inakura et al. |
| 3,989,952 A | 11/1976 | Timberlake et al. |
| 4,246,661 A | 1/1981 | Pinson |
| 4,258,716 A | 3/1981 | Sutherland |
| 4,278,077 A | 7/1981 | Mizumoto |
| 4,353,677 A | 10/1982 | Susnjara et al. |
| 4,538,594 A | 9/1985 | Boebel et al. |
| 4,568,311 A | 2/1986 | Miyaki |
| 4,576,545 A | 3/1986 | Maeda |
| 4,623,183 A | 11/1986 | Aomori |
| 4,636,138 A | 1/1987 | Gorman |
| 4,645,409 A | 2/1987 | Gorman |
| 4,684,313 A | 8/1987 | Minematsu et al. |
| 4,736,645 A | 4/1988 | Zimmer |
| 4,762,455 A | 8/1988 | Coughlan et al. |
| 4,771,652 A | 9/1988 | Zimmer |
| 4,852,391 A | 8/1989 | Ruch et al. |
| 4,854,808 A | 8/1989 | Bisiach |
| 4,896,015 A | 1/1990 | Taboada et al. |
| 4,897,014 A | 1/1990 | Tietze |
| 4,922,755 A | 5/1990 | Oshiro et al. |
| 4,922,782 A | 5/1990 | Kawai |
| 4,984,959 A | 1/1991 | Kato |
| 4,990,050 A | 2/1991 | Tsuge et al. |
| 5,019,968 A | 5/1991 | Wang et al. |
| 5,036,724 A | 8/1991 | Rosheim |
| 5,108,140 A | 4/1992 | Bartholet |
| 5,172,639 A | 12/1992 | Wiesman et al. |
| 5,176,649 A | 1/1993 | Wakabayashi |
| 5,178,032 A | 1/1993 | Zona et al. |
| 5,187,032 A | 2/1993 | Sasaki et al. |
| 5,187,796 A | 2/1993 | Wang et al. |
| 5,195,388 A | 3/1993 | Zona et al. |
| 5,201,325 A | 4/1993 | McEwen et al. |
| 5,217,003 A | 6/1993 | Wilk |
| 5,263,382 A | 11/1993 | Brooks et al. |
| 5,271,384 A | 12/1993 | McEwen et al. |
| 5,284,096 A | 2/1994 | Pelrine et al. |
| 5,297,443 A | 3/1994 | Wentz |
| 5,297,536 A | 3/1994 | Wilk |
| 5,304,899 A | 4/1994 | Sasaki et al. |
| 5,305,653 A | 4/1994 | Ohtani et al. |
| 5,307,447 A | 4/1994 | Asano et al. |
| 5,353,807 A | 10/1994 | DeMarco |
| 5,363,935 A | 11/1994 | Schempf et al. |
| 5,372,147 A | 12/1994 | Lathrop, Jr. et al. |
| 5,382,885 A | 1/1995 | Salcudean et al. |
| 5,441,494 A | 1/1995 | Oritz |
| 5,388,528 A | 2/1995 | Pelrine et al. |
| 5,397,323 A | 3/1995 | Taylor et al. |
| 5,436,542 A | 7/1995 | Petelin et al. |
| 5,456,673 A * | 10/1995 | Ziegler .............. A61B 17/3462 604/533 |
| 5,458,131 A | 10/1995 | Wilk |
| 5,458,583 A | 10/1995 | McNeely et al. |
| 5,458,598 A | 10/1995 | Feinberg et al. |
| 5,471,515 A | 11/1995 | Fossum et al. |
| 5,515,478 A | 5/1996 | Wang |
| 5,524,180 A | 6/1996 | Wang et al. |
| 5,553,198 A | 9/1996 | Wang et al. |
| 5,562,448 A | 10/1996 | Mushabac |
| 5,588,442 A | 12/1996 | Scovil et al. |
| 5,620,417 A | 4/1997 | Jang et al. |
| 5,623,582 A | 4/1997 | Rosenberg |
| 5,624,380 A | 4/1997 | Takayama et al. |
| 5,624,398 A | 4/1997 | Smith et al. |
| 5,632,761 A | 5/1997 | Smith et al. |
| 5,645,520 A | 7/1997 | Nakamura et al. |
| 5,657,429 A | 8/1997 | Wang et al. |
| 5,657,584 A | 8/1997 | Hamlin |
| 5,667,354 A | 9/1997 | Nakazawa |
| 5,672,168 A | 9/1997 | de la Torre et al. |
| 5,674,030 A | 10/1997 | Sigel |
| 5,728,599 A | 3/1998 | Rosteker et al. |
| 5,736,821 A | 4/1998 | Suyama et al. |
| 5,754,741 A | 5/1998 | Wang et al. |
| 5,762,458 A | 6/1998 | Wang et al. |
| 5,769,640 A | 6/1998 | Jacobus et al. |
| 5,791,231 A | 8/1998 | Cohn et al. |
| 5,792,135 A | 8/1998 | Madhani et al. |
| 5,797,538 A | 8/1998 | Heaton et al. |
| 5,797,900 A | 8/1998 | Madhani et al. |
| 5,807,377 A | 9/1998 | Madhani et al. |
| 5,808,665 A | 9/1998 | Green |
| 5,815,640 A | 9/1998 | Wang et al. |
| 5,825,982 A | 10/1998 | Wright et al. |
| 5,833,656 A | 11/1998 | Smith et al. |
| 5,841,950 A | 11/1998 | Wang et al. |
| 5,845,646 A | 12/1998 | Lemelson |
| 5,855,583 A | 1/1999 | Wang et al. |
| 5,876,325 A | 3/1999 | Mizuno et al. |
| 5,878,193 A | 3/1999 | Wang et al. |
| 5,878,783 A | 3/1999 | Smart |
| 5,895,377 A | 4/1999 | Smith et al. |
| 5,895,417 A | 4/1999 | Pomeranz et al. |
| 5,906,591 A | 5/1999 | Dario et al. |
| 5,907,664 A | 5/1999 | Wang et al. |
| 5,910,129 A | 6/1999 | Koblish et al. |
| 5,911,036 A | 6/1999 | Wright et al. |
| 5,954,692 A | 9/1999 | Smith et al. |
| 5,971,976 A | 10/1999 | Wang et al. |
| 5,993,467 A | 11/1999 | Yoon |
| 6,001,108 A | 12/1999 | Wang et al. |
| 6,007,550 A | 12/1999 | Wang et al. |
| 6,030,365 A | 2/2000 | Laufer |
| 6,031,371 A | 2/2000 | Smart |
| 6,058,323 A | 5/2000 | Lemelson |
| 6,063,095 A | 5/2000 | Wang et al. |
| 6,066,090 A | 5/2000 | Yoon |
| 6,086,529 A | 7/2000 | Arndt |
| 6,102,850 A | 8/2000 | Wang et al. |
| 6,106,521 A | 8/2000 | Blewett et al. |
| 6,107,795 A | 8/2000 | Smart |
| 6,132,368 A | 10/2000 | Cooper |
| 6,132,441 A | 10/2000 | Grace |
| 6,139,563 A | 10/2000 | Cosgrove, III et al. |
| 6,156,006 A | 12/2000 | Brosens et al. |
| 6,159,146 A | 12/2000 | El Gazayerli |
| 6,162,171 A | 12/2000 | Ng et al. |
| D438,617 S | 3/2001 | Cooper et al. |
| 6,206,903 B1 | 3/2001 | Ramans |
| D441,076 S | 4/2001 | Cooper et al. |
| 6,223,100 B1 | 4/2001 | Green |
| D441,862 S | 5/2001 | Cooper et al. |
| 6,238,415 B1 | 5/2001 | Sepetka et al. |
| 6,240,312 B1 | 5/2001 | Alfano et al. |
| 6,241,730 B1 | 6/2001 | Alby |
| 6,244,809 B1 | 6/2001 | Wang et al. |
| 6,246,200 B1 | 6/2001 | Blumenkranz et al. |
| D444,555 S | 7/2001 | Cooper et al. |
| 6,286,514 B1 | 9/2001 | Lemelson |
| 6,292,678 B1 | 9/2001 | Hall et al. |
| 6,293,282 B1 | 9/2001 | Lemelson |
| 6,296,635 B1 | 10/2001 | Smith et al. |
| 6,309,397 B1 | 10/2001 | Julian et al. |
| 6,309,403 B1 | 10/2001 | Minor et al. |
| 6,312,435 B1 | 11/2001 | Wallace et al. |
| 6,321,106 B1 | 11/2001 | Lemelson |
| 6,327,492 B1 | 12/2001 | Lemelson |
| 6,331,181 B1 | 12/2001 | Tierney et al. |
| 6,346,072 B1 | 2/2002 | Cooper |

(56) References Cited

U.S. PATENT DOCUMENTS

| | | |
|---|---|---|
| 6,352,503 B1 | 3/2002 | Matsui et al. |
| 6,364,888 B1 | 4/2002 | Niemeyer et al. |
| 6,371,952 B1 | 4/2002 | Madhani et al. |
| 6,394,998 B1 | 5/2002 | Wallace et al. |
| 6,398,726 B1 | 6/2002 | Ramans et al. |
| 6,400,980 B1 | 6/2002 | Lemelson |
| 6,408,224 B1 | 6/2002 | Lemelson |
| 6,424,885 B1 | 7/2002 | Niemeyer et al. |
| 6,432,112 B2 | 8/2002 | Brock et al. |
| 6,436,107 B1 | 8/2002 | Wang et al. |
| 6,441,577 B2 | 8/2002 | Blumenkranz et al. |
| 6,450,104 B1 | 9/2002 | Grant et al. |
| 6,450,992 B1 * | 9/2002 | Cassidy, Jr. ........ A61B 17/3421 604/164.01 |
| 6,451,027 B1 | 9/2002 | Cooper et al. |
| 6,454,758 B1 | 9/2002 | Thompson et al. |
| 6,459,926 B1 | 10/2002 | Nowlin et al. |
| 6,463,361 B1 | 10/2002 | Wang et al. |
| 6,468,203 B2 | 10/2002 | Belson |
| 6,468,265 B1 | 10/2002 | Evans et al. |
| 6,470,236 B2 | 10/2002 | Ohtsuki |
| 6,491,691 B1 | 12/2002 | Morley et al. |
| 6,491,701 B2 | 12/2002 | Nemeyer et al. |
| 6,493,608 B1 | 12/2002 | Niemeyer et al. |
| 6,496,099 B2 | 12/2002 | Wang et al. |
| 6,497,651 B1 | 12/2002 | Kan et al. |
| 6,508,413 B2 | 1/2003 | Bauer et al. |
| 6,512,345 B2 | 1/2003 | Borenstein |
| 6,522,906 B1 | 2/2003 | Salisbury, Jr. et al. |
| 6,544,276 B1 | 4/2003 | Azizi |
| 6,548,982 B1 | 4/2003 | Papanikolopoulos et al. |
| 6,554,790 B1 | 4/2003 | Moll |
| 6,565,554 B1 | 5/2003 | Niemeyer |
| 6,574,355 B2 | 6/2003 | Green |
| 6,587,750 B2 | 7/2003 | Gerbi et al. |
| 6,591,239 B1 | 7/2003 | McCall et al. |
| 6,594,552 B1 | 7/2003 | Nowlin et al. |
| 6,610,007 B2 | 8/2003 | Belson et al. |
| 6,620,173 B2 | 9/2003 | Gerbi et al. |
| 6,642,836 B1 | 11/2003 | Wang et al. |
| 6,645,196 B1 | 11/2003 | Nixon et al. |
| 6,646,541 B1 | 11/2003 | Wang et al. |
| 6,648,814 B2 | 11/2003 | Kim et al. |
| 6,659,939 B2 | 12/2003 | Moll et al. |
| 6,661,571 B1 | 12/2003 | Shioda et al. |
| 6,671,581 B2 | 12/2003 | Niemeyer et al. |
| 6,676,684 B1 | 1/2004 | Morley et al. |
| 6,684,129 B2 | 1/2004 | Salisbury, Jr. et al. |
| 6,685,648 B2 | 2/2004 | Flaherty et al. |
| 6,685,698 B2 | 2/2004 | Morley et al. |
| 6,687,571 B1 | 2/2004 | Byme et al. |
| 6,692,485 B1 | 2/2004 | Brock et al. |
| 6,699,177 B1 | 3/2004 | Wang et al. |
| 6,699,235 B2 | 3/2004 | Wallace et al. |
| 6,702,734 B2 | 3/2004 | Kim et al. |
| 6,702,805 B1 | 3/2004 | Stuart |
| 6,714,839 B2 | 3/2004 | Salisbury, Jr. et al. |
| 6,714,841 B1 | 3/2004 | Wright et al. |
| 6,719,684 B2 | 4/2004 | Kim et al. |
| 6,720,988 B1 | 4/2004 | Gere et al. |
| 6,726,699 B1 | 4/2004 | Wright et al. |
| 6,728,599 B2 | 4/2004 | Wright et al. |
| 6,730,021 B2 | 5/2004 | Vassiliades, Jr. et al. |
| 6,731,988 B1 | 5/2004 | Green |
| 6,746,443 B1 | 6/2004 | Morley et al. |
| 6,764,441 B2 | 7/2004 | Chiel et al. |
| 6,764,445 B2 | 7/2004 | Ramans et al. |
| 6,766,204 B2 | 7/2004 | Niemeyer et al. |
| 6,770,081 B1 | 8/2004 | Cooper et al. |
| 6,774,597 B1 | 8/2004 | Borenstein |
| 6,776,165 B2 | 8/2004 | Jin |
| 6,780,184 B2 | 8/2004 | Tanrisever |
| 6,783,524 B2 | 8/2004 | Anderson et al. |
| 6,785,593 B2 | 8/2004 | Wang et al. |
| 6,788,018 B1 | 9/2004 | Blumenkranz |
| 6,792,663 B2 | 9/2004 | Krzyzanowski |
| 6,793,653 B2 | 9/2004 | Sanchez et al. |
| 6,799,065 B1 | 9/2004 | Niemeyer |
| 6,799,088 B2 | 9/2004 | Wang et al. |
| 6,801,325 B2 | 10/2004 | Farr et al. |
| 6,804,581 B2 | 10/2004 | Wang et al. |
| 6,810,281 B2 | 10/2004 | Brock et al. |
| 6,817,972 B2 | 11/2004 | Snow |
| 6,817,974 B2 | 11/2004 | Cooper et al. |
| 6,817,975 B1 | 11/2004 | Farr et al. |
| 6,820,653 B1 | 11/2004 | Schempf et al. |
| 6,824,508 B2 | 11/2004 | Kim et al. |
| 6,824,510 B2 | 11/2004 | Kim et al. |
| 6,826,977 B2 | 12/2004 | Grover et al. |
| 6,832,988 B2 | 12/2004 | Sprout |
| 6,832,996 B2 | 12/2004 | Woloszko et al. |
| 6,836,703 B2 | 12/2004 | Wang et al. |
| 6,837,846 B2 | 1/2005 | Jaffe et al. |
| 6,837,883 B2 | 1/2005 | Moll et al. |
| 6,839,612 B2 | 1/2005 | Sanchez et al. |
| 6,840,938 B1 | 1/2005 | Morley et al. |
| 6,843,793 B2 | 1/2005 | Brock et al. |
| 6,852,107 B2 | 2/2005 | Wang et al. |
| 6,853,879 B2 | 2/2005 | Sunaoshi |
| 6,858,003 B2 | 2/2005 | Evans et al. |
| 6,860,346 B2 | 3/2005 | Burt et al. |
| 6,860,877 B1 | 3/2005 | Sanchez et al. |
| 6,866,671 B2 | 3/2005 | Tiemey et al. |
| 6,870,343 B2 | 3/2005 | Borenstein et al. |
| 6,871,117 B2 | 3/2005 | Wang et al. |
| 6,871,563 B2 | 3/2005 | Choset et al. |
| 6,879,880 B2 | 4/2005 | Nowlin et al. |
| 6,892,112 B2 | 5/2005 | Wang et al. |
| 6,899,705 B2 | 5/2005 | Niemeyer |
| 6,902,560 B1 | 6/2005 | Morley et al. |
| 6,905,460 B2 | 6/2005 | Wang et al. |
| 6,905,491 B1 | 6/2005 | Wang et al. |
| 6,911,916 B1 | 6/2005 | Wang et al. |
| 6,917,176 B2 | 7/2005 | Schempf et al. |
| 6,933,695 B2 | 8/2005 | Blumenkranz |
| 6,936,001 B1 | 8/2005 | Snow |
| 6,936,003 B2 | 8/2005 | Iddan |
| 6,936,042 B2 | 8/2005 | Wallace et al. |
| 6,943,663 B2 | 9/2005 | Wang et al. |
| 6,949,096 B2 | 9/2005 | Davison et al. |
| 6,951,535 B2 | 10/2005 | Ghodoussi et al. |
| 6,963,792 B1 | 11/2005 | Green |
| 6,965,812 B2 | 11/2005 | Wang et al. |
| 6,974,411 B2 | 12/2005 | Belson |
| 6,974,449 B2 | 12/2005 | Niemeyer |
| 6,979,423 B2 | 12/2005 | Moll |
| 6,984,203 B2 | 1/2006 | Tartaglia et al. |
| 6,984,205 B2 | 1/2006 | Gazdzinski |
| 6,991,627 B2 | 1/2006 | Madhani et al. |
| 6,993,413 B2 | 1/2006 | Sunaoshi |
| 6,994,703 B2 | 2/2006 | Wang et al. |
| 6,994,708 B2 | 2/2006 | Manzo |
| 6,997,908 B2 | 2/2006 | Carrillo, Jr. et al. |
| 6,999,852 B2 | 2/2006 | Green |
| 7,025,064 B2 | 4/2006 | Wang et al. |
| 7,027,892 B2 | 4/2006 | Wang et al. |
| 7,033,344 B2 | 4/2006 | Imran |
| 7,039,453 B2 | 5/2006 | Mullick |
| 7,042,184 B2 | 5/2006 | Oleynikov et al. |
| 7,048,745 B2 | 5/2006 | Tierney et al. |
| 7,053,752 B2 | 5/2006 | Wang et al. |
| 7,063,682 B1 | 6/2006 | Whayne et al. |
| 7,066,879 B2 | 6/2006 | Fowler et al. |
| 7,066,926 B2 | 6/2006 | Wallace et al. |
| 7,074,179 B2 | 7/2006 | Wang et al. |
| 7,077,446 B2 | 7/2006 | Kameda et al. |
| 7,083,571 B2 | 8/2006 | Wang et al. |
| 7,083,615 B2 | 8/2006 | Peterson et al. |
| 7,087,049 B2 | 8/2006 | Nowlin et al. |
| 7,090,683 B2 | 8/2006 | Brock et al. |
| 7,097,640 B2 | 8/2006 | Wang et al. |
| 7,105,000 B2 | 9/2006 | McBrayer |
| 7,107,090 B2 | 9/2006 | Salisbury, Jr. et al. |
| 7,109,678 B2 | 9/2006 | Kraus et al. |

(56) References Cited

U.S. PATENT DOCUMENTS

| | | |
|---|---|---|
| 7,118,582 B1 | 10/2006 | Wang et al. |
| 7,121,781 B2 | 10/2006 | Sanchez et al. |
| 7,125,403 B2 | 10/2006 | Julian et al. |
| 7,126,303 B2 | 10/2006 | Farritor et al. |
| 7,147,650 B2 | 12/2006 | Lee |
| 7,155,315 B2 | 12/2006 | Niemeyer et al. |
| 7,155,316 B2 | 12/2006 | Sutherland et al. |
| 7,163,525 B2 | 1/2007 | Franer |
| 7,169,141 B2 | 1/2007 | Brock et al. |
| 7,182,025 B2 | 2/2007 | Ghorbel et al. |
| 7,182,089 B2 | 2/2007 | Ries |
| 7,199,545 B2 | 4/2007 | Oleynikov et al. |
| 7,206,626 B2 | 4/2007 | Quaid, III |
| 7,206,627 B2 | 4/2007 | Abovitz et al. |
| 7,210,364 B2 | 5/2007 | Ghorbel et al. |
| 7,214,230 B2 | 5/2007 | Brock et al. |
| 7,217,240 B2 | 5/2007 | Snow |
| 7,239,940 B2 | 7/2007 | Wang et al. |
| 7,250,028 B2 | 7/2007 | Julian et al. |
| 7,259,652 B2 | 8/2007 | Wang et al. |
| 7,273,488 B2 | 9/2007 | Nakamura et al. |
| 7,311,107 B2 | 12/2007 | Harel et al. |
| 7,339,341 B2 | 3/2008 | Oleynikov et al. |
| 7,372,229 B2 | 5/2008 | Farritor et al. |
| 7,403,836 B2 | 7/2008 | Aoyama |
| 7,438,702 B2 | 10/2008 | Hart et al. |
| 7,447,537 B1 | 11/2008 | Funda et al. |
| 7,492,116 B2 | 2/2009 | Oleynikov et al. |
| 7,566,300 B2 | 7/2009 | Devierre et al. |
| 7,574,250 B2 | 8/2009 | Niemeyer |
| 7,637,905 B2 | 12/2009 | Saadat et al. |
| 7,645,230 B2 | 1/2010 | Mikkaichi et al. |
| 7,655,004 B2 | 2/2010 | Long |
| 7,670,329 B2 | 3/2010 | Flaherty et al. |
| 7,678,043 B2 | 3/2010 | Gilad |
| 7,731,727 B2 | 6/2010 | Sauer |
| 7,734,375 B2 | 6/2010 | Buehler et al. |
| 7,762,825 B2 | 7/2010 | Burbank et al. |
| 7,772,796 B2 | 8/2010 | Farritor et al. |
| 7,785,251 B2 | 8/2010 | Wilk |
| 7,785,294 B2 | 8/2010 | Hueil et al. |
| 7,785,333 B2 | 8/2010 | Miyamoto et al. |
| 7,789,825 B2 | 9/2010 | Nobis et al. |
| 7,789,861 B2 | 9/2010 | Franer |
| 7,794,494 B2 | 9/2010 | Sahatjian et al. |
| 7,865,266 B2 | 1/2011 | Moll et al. |
| 7,960,935 B2 | 6/2011 | Farritor et al. |
| 7,979,157 B2 | 7/2011 | Anvari |
| 8,021,358 B2 | 9/2011 | Doyle et al. |
| 8,179,073 B2 | 5/2012 | Farritor et al. |
| 8,231,610 B2 | 7/2012 | Jo et al. |
| 8,343,171 B2 | 1/2013 | Farritor et al. |
| 8,353,897 B2 | 1/2013 | Doyle et al. |
| 8,377,045 B2 | 2/2013 | Schena |
| 8,430,851 B2 * | 4/2013 | McGinley ............ A61M 13/003 604/167.03 |
| 8,604,742 B2 | 12/2013 | Farritor et al. |
| 8,636,686 B2 | 1/2014 | Minnelli et al. |
| 8,679,096 B2 | 3/2014 | Farritor et al. |
| 8,827,337 B2 | 9/2014 | Murata et al. |
| 8,828,024 B2 | 9/2014 | Farritor et al. |
| 8,834,488 B2 | 9/2014 | Farritor et al. |
| 8,864,652 B2 | 10/2014 | Diolaiti et al. |
| 8,888,687 B2 | 11/2014 | Ostrovsky et al. |
| 8,968,332 B2 | 3/2015 | Farritor et al. |
| 8,974,440 B2 | 3/2015 | Farritor et al. |
| 8,986,196 B2 | 3/2015 | Larkin et al. |
| 9,010,214 B2 | 4/2015 | Markvicka et al. |
| 9,060,781 B2 | 6/2015 | Farritor et al. |
| 9,089,256 B2 | 7/2015 | Tognaccini et al. |
| 9,089,353 B2 | 7/2015 | Farritor et al. |
| 9,138,129 B2 | 9/2015 | Diolaiti |
| 9,198,728 B2 | 12/2015 | Wang et al. |
| 9,516,996 B2 | 12/2016 | Diolaiti et al. |
| 9,579,088 B2 | 2/2017 | Farritor et al. |
| 9,649,020 B2 | 5/2017 | Finlay |
| 9,717,563 B2 | 8/2017 | Tognaccini et al. |
| 9,743,987 B2 | 8/2017 | Farritor et al. |
| 9,757,187 B2 | 9/2017 | Farritor et al. |
| 9,770,305 B2 | 9/2017 | Farritor et al. |
| 9,789,608 B2 | 10/2017 | Itkowitz et al. |
| 9,814,640 B1 | 11/2017 | Khaligh |
| 9,816,641 B2 | 11/2017 | Bock-Aronson et al. |
| 9,849,586 B2 | 12/2017 | Rosheim |
| 9,857,786 B2 | 1/2018 | Cristiano |
| 9,888,966 B2 | 2/2018 | Farritor et al. |
| 9,956,043 B2 | 5/2018 | Farritor et al. |
| 10,008,017 B2 | 6/2018 | Itkowitz et al. |
| 10,111,711 B2 | 10/2018 | Farritor et al. |
| 10,137,575 B2 | 11/2018 | Itkowitz et al. |
| 10,159,533 B2 | 12/2018 | Moll et al. |
| 10,220,522 B2 | 3/2019 | Rockrohr |
| 10,258,425 B2 | 4/2019 | Mustufa et al. |
| 10,307,199 B2 | 6/2019 | Farritor et al. |
| 10,342,561 B2 | 7/2019 | Farritor et al. |
| 10,368,952 B2 | 8/2019 | Tognaccini et al. |
| 10,398,516 B2 | 9/2019 | Jackson et al. |
| 10,470,828 B2 | 11/2019 | Markvicka et al. |
| 10,507,066 B2 | 12/2019 | Dimaio et al. |
| 10,555,775 B2 | 2/2020 | Hoffman et al. |
| 10,582,973 B2 | 3/2020 | Wilson et al. |
| 10,695,137 B2 | 6/2020 | Farritor et al. |
| 10,729,503 B2 | 8/2020 | Cameron |
| 10,737,394 B2 | 8/2020 | Itkowitz et al. |
| 10,751,136 B2 | 8/2020 | Farritor et al. |
| 10,751,883 B2 | 8/2020 | Nahum |
| 10,806,538 B2 | 10/2020 | Farritor et al. |
| 10,966,700 B2 | 4/2021 | Farritor et al. |
| 11,032,125 B2 | 6/2021 | Farritor et al. |
| 11,298,195 B2 | 4/2022 | Ye et al. |
| 11,382,702 B2 | 7/2022 | Tognaccini et al. |
| 11,529,201 B2 | 12/2022 | Mondry et al. |
| 11,595,242 B2 | 2/2023 | Farritor et al. |
| 2001/0018591 A1 | 8/2001 | Brock et al. |
| 2001/0049497 A1 | 12/2001 | Kalloo et al. |
| 2002/0003173 A1 | 1/2002 | Bauer et al. |
| 2002/0013601 A1 | 1/2002 | Nobles et al. |
| 2002/0026186 A1 | 2/2002 | Woloszko et al. |
| 2002/0038077 A1 | 3/2002 | de la Torre et al. |
| 2002/0065507 A1 | 5/2002 | Zando-Azizi |
| 2002/0091374 A1 | 6/2002 | Cooper |
| 2002/0103417 A1 | 8/2002 | Gazdzinski |
| 2002/0111535 A1 | 8/2002 | Kim et al. |
| 2002/0120254 A1 | 8/2002 | Julian et al. |
| 2002/0128552 A1 | 9/2002 | Nowlin et al. |
| 2002/0140392 A1 | 10/2002 | Borenstein et al. |
| 2002/0147487 A1 | 10/2002 | Sundquist et al. |
| 2002/0151906 A1 | 10/2002 | Demarais et al. |
| 2002/0156347 A1 | 10/2002 | Kim et al. |
| 2002/0171385 A1 | 11/2002 | Kim et al. |
| 2002/0173700 A1 | 11/2002 | Kim et al. |
| 2002/0190682 A1 | 12/2002 | Schempf et al. |
| 2003/0020810 A1 | 1/2003 | Takizawa et al. |
| 2003/0045888 A1 | 3/2003 | Brock et al. |
| 2003/0065250 A1 | 4/2003 | Chiel et al. |
| 2003/0089267 A1 | 5/2003 | Ghorbel et al. |
| 2003/0092964 A1 | 5/2003 | Kim et al. |
| 2003/0097129 A1 | 5/2003 | Davison et al. |
| 2003/0100817 A1 | 5/2003 | Wang et al. |
| 2003/0109780 A1 | 6/2003 | Coste-Maniere et al. |
| 2003/0114731 A1 | 6/2003 | Cadeddu et al. |
| 2003/0135203 A1 | 6/2003 | Wang et al. |
| 2003/0139742 A1 | 7/2003 | Wampler et al. |
| 2003/0144656 A1 | 7/2003 | Ocel et al. |
| 2003/0159535 A1 | 8/2003 | Grover et al. |
| 2003/0167000 A1 | 9/2003 | Mullick |
| 2003/0172871 A1 | 9/2003 | Scherer |
| 2003/0179308 A1 | 9/2003 | Zamorano et al. |
| 2003/0181788 A1 | 9/2003 | Yokoi et al. |
| 2003/0225479 A1 | 12/2003 | Waled |
| 2003/0229268 A1 | 12/2003 | Uchiyama et al. |
| 2003/0229338 A1 | 12/2003 | Irion et al. |
| 2003/0230372 A1 | 12/2003 | Schmidt |
| 2004/0024311 A1 | 2/2004 | Quaid |

(56) References Cited

U.S. PATENT DOCUMENTS

| | | |
|---|---|---|
| 2004/0034282 A1 | 2/2004 | Quaid |
| 2004/0034283 A1 | 2/2004 | Quaid |
| 2004/0034302 A1 | 2/2004 | Abovitz et al. |
| 2004/0050394 A1 | 3/2004 | Jin |
| 2004/0070822 A1 | 4/2004 | Shioda et al. |
| 2004/0099175 A1 | 5/2004 | Perrot et al. |
| 2004/0102772 A1 | 5/2004 | Baxter et al. |
| 2004/0106916 A1 | 6/2004 | Quaid et al. |
| 2004/0111113 A1 | 6/2004 | Nakamura et al. |
| 2004/0117032 A1 | 6/2004 | Roth |
| 2004/0138525 A1 | 7/2004 | Saadat et al. |
| 2004/0138552 A1 | 7/2004 | Harel et al. |
| 2004/0140786 A1 | 7/2004 | Borenstein |
| 2004/0153057 A1 | 8/2004 | Davison |
| 2004/0173116 A1 | 9/2004 | Ghorbel et al. |
| 2004/0176664 A1 | 9/2004 | Iddan |
| 2004/0215331 A1 | 10/2004 | Chew et al. |
| 2004/0225229 A1 | 11/2004 | Viola |
| 2004/0254680 A1 | 12/2004 | Sunaoshi |
| 2004/0267326 A1 | 12/2004 | Ocel |
| 2005/0014994 A1 | 1/2005 | Fowler et al. |
| 2005/0021069 A1 | 1/2005 | Feuer et al. |
| 2005/0029978 A1 | 2/2005 | Oleynikov et al. |
| 2005/0043583 A1 | 2/2005 | Killmann et al. |
| 2005/0049462 A1 | 3/2005 | Kanazawa |
| 2005/0054901 A1 | 3/2005 | Yoshino |
| 2005/0054902 A1 | 3/2005 | Konno |
| 2005/0064378 A1 | 3/2005 | Toly |
| 2005/0065400 A1 | 3/2005 | Banik et al. |
| 2005/0070850 A1* | 3/2005 | Albrecht ............ A61B 17/3462 604/167.03 |
| 2005/0083460 A1 | 4/2005 | Hattori et al. |
| 2005/0095650 A1 | 5/2005 | Julius et al. |
| 2005/0096502 A1 | 5/2005 | Khalili |
| 2005/0143644 A1 | 6/2005 | Gilad et al. |
| 2005/0154376 A1 | 7/2005 | Riviere et al. |
| 2005/0165449 A1 | 7/2005 | Cadeddu et al. |
| 2005/0177026 A1 | 8/2005 | Hoeg et al. |
| 2005/0234294 A1 | 10/2005 | Saadat et al. |
| 2005/0234435 A1 | 10/2005 | Layer |
| 2005/0272977 A1 | 12/2005 | Saadat et al. |
| 2005/0283137 A1 | 12/2005 | Doyle et al. |
| 2005/0288555 A1 | 12/2005 | Binmoeller |
| 2005/0288665 A1 | 12/2005 | Woloszko |
| 2006/0020272 A1 | 1/2006 | Gildenberg |
| 2006/0046226 A1 | 3/2006 | Bergler et al. |
| 2006/0079889 A1 | 4/2006 | Scott |
| 2006/0100501 A1 | 5/2006 | Berkelman et al. |
| 2006/0119304 A1 | 6/2006 | Farritor et al. |
| 2006/0149135 A1 | 7/2006 | Paz |
| 2006/0152591 A1 | 7/2006 | Lin |
| 2006/0155263 A1 | 7/2006 | Lipow |
| 2006/0189845 A1 | 8/2006 | Maahs et al. |
| 2006/0195015 A1 | 8/2006 | Mullick et al. |
| 2006/0196301 A1 | 9/2006 | Oleynikov et al. |
| 2006/0198619 A1 | 9/2006 | Oleynikov et al. |
| 2006/0241570 A1 | 10/2006 | Wilk |
| 2006/0241732 A1 | 10/2006 | Denker |
| 2006/0253109 A1 | 11/2006 | Chu |
| 2006/0258938 A1 | 11/2006 | Hoffman et al. |
| 2006/0258954 A1 | 11/2006 | Timberlake et al. |
| 2006/0261770 A1 | 11/2006 | Kishi et al. |
| 2007/0032701 A1 | 2/2007 | Fowler et al. |
| 2007/0043397 A1 | 2/2007 | Ocel et al. |
| 2007/0055342 A1 | 3/2007 | Wu et al. |
| 2007/0080658 A1 | 4/2007 | Farritor et al. |
| 2007/0088277 A1* | 4/2007 | McGinley ............ A61M 13/003 604/167.01 |
| 2007/0088340 A1 | 4/2007 | Brock et al. |
| 2007/0106113 A1 | 5/2007 | Ravo |
| 2007/0106317 A1 | 5/2007 | Shelton et al. |
| 2007/0123748 A1 | 5/2007 | Meglan |
| 2007/0135803 A1 | 6/2007 | Belson |
| 2007/0142725 A1 | 6/2007 | Hardin et al. |
| 2007/0156019 A1 | 7/2007 | Arkin et al. |
| 2007/0156211 A1 | 7/2007 | Ferren et al. |
| 2007/0167955 A1 | 7/2007 | De La Menardiere et al. |
| 2007/0225633 A1 | 9/2007 | Ferren et al. |
| 2007/0225634 A1 | 9/2007 | Ferren et al. |
| 2007/0241714 A1 | 10/2007 | Oleynikov et al. |
| 2007/0244520 A1 | 10/2007 | Ferren et al. |
| 2007/0250064 A1 | 10/2007 | Darois et al. |
| 2007/0255273 A1 | 11/2007 | Fernandez et al. |
| 2007/0287884 A1 | 12/2007 | Schena |
| 2008/0004634 A1 | 1/2008 | Farritor et al. |
| 2008/0015565 A1 | 1/2008 | Davison |
| 2008/0015566 A1 | 1/2008 | Livneh |
| 2008/0021440 A1 | 1/2008 | Solomon |
| 2008/0033569 A1 | 2/2008 | Ferren et al. |
| 2008/0045803 A1 | 2/2008 | Williams et al. |
| 2008/0058835 A1 | 3/2008 | Farritor et al. |
| 2008/0058989 A1 | 3/2008 | Oleynikov et al. |
| 2008/0071289 A1 | 3/2008 | Cooper et al. |
| 2008/0071290 A1 | 3/2008 | Larkin et al. |
| 2008/0103440 A1 | 5/2008 | Ferren et al. |
| 2008/0109014 A1 | 5/2008 | de la Pena |
| 2008/0111513 A1 | 5/2008 | Farritor et al. |
| 2008/0119870 A1 | 5/2008 | Williams et al. |
| 2008/0132890 A1 | 6/2008 | Woloszko et al. |
| 2008/0161804 A1 | 6/2008 | Rioux et al. |
| 2008/0164079 A1 | 7/2008 | Ferren et al. |
| 2008/0168639 A1 | 7/2008 | Otake et al. |
| 2008/0183033 A1 | 7/2008 | Bern et al. |
| 2008/0221591 A1 | 9/2008 | Farritor et al. |
| 2008/0269557 A1 | 10/2008 | Marescaux et al. |
| 2008/0269562 A1 | 10/2008 | Marescaux et al. |
| 2009/0002414 A1 | 1/2009 | Shibata et al. |
| 2009/0012532 A1 | 1/2009 | Quaid et al. |
| 2009/0020724 A1 | 1/2009 | Paffrath |
| 2009/0024142 A1 | 1/2009 | Ruiz Morales |
| 2009/0048612 A1 | 2/2009 | Farritor et al. |
| 2009/0054909 A1 | 2/2009 | Farritor et al. |
| 2009/0069821 A1 | 3/2009 | Farritor et al. |
| 2009/0076536 A1 | 3/2009 | Rentschler et al. |
| 2009/0137952 A1 | 5/2009 | Ramamurthy et al. |
| 2009/0143787 A9 | 6/2009 | De La Pena |
| 2009/0163929 A1 | 6/2009 | Yeung et al. |
| 2009/0171373 A1 | 7/2009 | Farritor et al. |
| 2009/0192524 A1 | 7/2009 | Itkowitz et al. |
| 2009/0234369 A1 | 9/2009 | Bax et al. |
| 2009/0236400 A1 | 9/2009 | Cole et al. |
| 2009/0240246 A1 | 9/2009 | Devill et al. |
| 2009/0247821 A1 | 10/2009 | Rogers |
| 2009/0248038 A1 | 10/2009 | Blumenkranz et al. |
| 2009/0281377 A1 | 11/2009 | Newell et al. |
| 2009/0299143 A1 | 12/2009 | Conlon et al. |
| 2009/0305210 A1 | 12/2009 | Guru et al. |
| 2009/0326322 A1 | 12/2009 | Diolaiti |
| 2010/0010294 A1 | 1/2010 | Conlon et al. |
| 2010/0016659 A1 | 1/2010 | Weitzner et al. |
| 2010/0016853 A1 | 1/2010 | Burbank |
| 2010/0026347 A1 | 2/2010 | Iizuka |
| 2010/0042097 A1 | 2/2010 | Newton et al. |
| 2010/0056863 A1 | 3/2010 | Dejima et al. |
| 2010/0069710 A1 | 3/2010 | Yamatani et al. |
| 2010/0069940 A1 | 3/2010 | Miller et al. |
| 2010/0081875 A1 | 4/2010 | Fowler et al. |
| 2010/0101346 A1 | 4/2010 | Johnson et al. |
| 2010/0130986 A1 | 5/2010 | Mailloux et al. |
| 2010/0139436 A1 | 6/2010 | Kawashima et al. |
| 2010/0185212 A1 | 7/2010 | Sholev |
| 2010/0198231 A1 | 8/2010 | Manzo et al. |
| 2010/0204713 A1 | 8/2010 | Ruiz Morales |
| 2010/0245549 A1 | 9/2010 | Allen et al. |
| 2010/0250000 A1 | 9/2010 | Blumenkranz et al. |
| 2010/0262162 A1 | 10/2010 | Omori |
| 2010/0263470 A1 | 10/2010 | Bannasch et al. |
| 2010/0274079 A1 | 10/2010 | Kim et al. |
| 2010/0292691 A1 | 11/2010 | Brogna |
| 2010/0301095 A1 | 12/2010 | Shelton, IV et al. |
| 2010/0318059 A1 | 12/2010 | Farritor et al. |
| 2010/0331856 A1 | 12/2010 | Carlson et al. |
| 2011/0015569 A1 | 1/2011 | Kirschenman et al. |
| 2011/0020779 A1 | 1/2011 | Hannaford et al. |

(56) References Cited

U.S. PATENT DOCUMENTS

| | | |
|---|---|---|
| 2011/0071347 A1 | 3/2011 | Rogers et al. |
| 2011/0071544 A1 | 3/2011 | Steger et al. |
| 2011/0075693 A1 | 3/2011 | Kuramochi et al. |
| 2011/0077478 A1 | 3/2011 | Freeman et al. |
| 2011/0082365 A1 | 4/2011 | Mcgrogan et al. |
| 2011/0098529 A1 | 4/2011 | Ostrovsky et al. |
| 2011/0107866 A1 | 5/2011 | Oka et al. |
| 2011/0152615 A1 | 6/2011 | Schostek et al. |
| 2011/0224605 A1 | 9/2011 | Farritor et al. |
| 2011/0230894 A1 | 9/2011 | Simaan et al. |
| 2011/0237890 A1 | 9/2011 | Farritor et al. |
| 2011/0238079 A1 | 9/2011 | Hannaford et al. |
| 2011/0238080 A1 | 9/2011 | Ranjit et al. |
| 2011/0264078 A1 | 10/2011 | Lipow et al. |
| 2011/0270443 A1 | 11/2011 | Kamiya et al. |
| 2011/0276046 A1 | 11/2011 | Heimbecker et al. |
| 2012/0016175 A1 | 1/2012 | Roberts et al. |
| 2012/0029727 A1 | 2/2012 | Sholev |
| 2012/0035582 A1 | 2/2012 | Nelson et al. |
| 2012/0059392 A1 | 3/2012 | Diolaiti |
| 2012/0078053 A1 | 3/2012 | Phee et al. |
| 2012/0109150 A1 | 5/2012 | Quaid et al. |
| 2012/0116362 A1 | 5/2012 | Kieturakis |
| 2012/0179168 A1 | 7/2012 | Farritor et al. |
| 2012/0221147 A1 | 8/2012 | Goldberg et al. |
| 2012/0253515 A1 | 10/2012 | Coste-Maniere et al. |
| 2013/0001970 A1 | 1/2013 | Suyama et al. |
| 2013/0041360 A1 | 2/2013 | Farritor et al. |
| 2013/0055560 A1 | 3/2013 | Nakasugi et al. |
| 2013/0125696 A1 | 5/2013 | Long |
| 2013/0131695 A1 | 5/2013 | Scarfogliero et al. |
| 2013/0178867 A1 | 7/2013 | Farritor et al. |
| 2013/0282023 A1 | 10/2013 | Burbank et al. |
| 2013/0304084 A1 | 11/2013 | Beira et al. |
| 2013/0325030 A1 | 12/2013 | Hourtash et al. |
| 2013/0325181 A1 | 12/2013 | Moore |
| 2013/0345717 A1 | 12/2013 | Markvicka et al. |
| 2013/0345718 A1 | 12/2013 | Crawford et al. |
| 2014/0039515 A1 | 2/2014 | Mondry et al. |
| 2014/0046340 A1 | 2/2014 | Wilson et al. |
| 2014/0055489 A1 | 2/2014 | Itkowitz et al. |
| 2014/0058205 A1 | 2/2014 | Frederick et al. |
| 2014/0100587 A1 | 4/2014 | Farritor et al. |
| 2014/0137687 A1 | 5/2014 | Nogami et al. |
| 2014/0221749 A1 | 8/2014 | Grant et al. |
| 2014/0232824 A1 | 8/2014 | Dimaio et al. |
| 2014/0276944 A1 | 9/2014 | Farritor et al. |
| 2014/0303434 A1 | 10/2014 | Farritor et al. |
| 2014/0371762 A1 | 12/2014 | Farritor et al. |
| 2015/0051446 A1 | 2/2015 | Farritor et al. |
| 2015/0057537 A1* | 2/2015 | Dillon .................. A61B 1/0014 600/113 |
| 2015/0157191 A1 | 6/2015 | Phee et al. |
| 2015/0223896 A1 | 8/2015 | Farritor et al. |
| 2015/0297299 A1 | 10/2015 | Yeung et al. |
| 2016/0066999 A1 | 3/2016 | Forgione et al. |
| 2016/0135898 A1 | 5/2016 | Frederick et al. |
| 2016/0291571 A1 | 10/2016 | Cristiano |
| 2016/0303745 A1 | 10/2016 | Rockrohr |
| 2017/0014197 A1 | 1/2017 | Mccrea et al. |
| 2017/0035526 A1* | 2/2017 | Farritor .................. A61B 34/35 |
| 2017/0078583 A1 | 3/2017 | Haggerty et al. |
| 2017/0252096 A1 | 9/2017 | Felder et al. |
| 2017/0354470 A1 | 12/2017 | Farritor et al. |
| 2018/0132956 A1 | 5/2018 | Cameron |
| 2018/0153578 A1 | 6/2018 | Cooper et al. |
| 2018/0338777 A1 | 11/2018 | Bonadio et al. |
| 2019/0059983 A1* | 2/2019 | Germain ............ A61B 17/1606 |
| 2019/0090965 A1 | 3/2019 | Farritor et al. |
| 2019/0209262 A1 | 7/2019 | Mustufa et al. |
| 2019/0327394 A1 | 10/2019 | Ramirez Luna et al. |
| 2020/0138534 A1 | 5/2020 | Garcia Kilroy et al. |
| 2020/0214775 A1 | 7/2020 | Farritor et al. |
| 2020/0330175 A1 | 10/2020 | Cameron |
| 2020/0368915 A1 | 11/2020 | Itkowitz et al. |

FOREIGN PATENT DOCUMENTS

| | | |
|---|---|---|
| CN | 102821918 | 12/2012 |
| CN | 104523309 A | 4/2015 |
| CN | 104582600 A | 4/2015 |
| CN | 104622528 A | 5/2015 |
| CN | 204337044 U | 5/2015 |
| CN | 105025826 A | 11/2015 |
| DE | 102010040405 | 3/2012 |
| EP | 0105656 A2 | 4/1984 |
| EP | 0279591 A1 | 8/1988 |
| EP | 1354670 | 10/2003 |
| EP | 2286756 | 2/2011 |
| EP | 2286756 A1 | 2/2011 |
| EP | 2329787 | 6/2011 |
| EP | 2563261 | 3/2013 |
| EP | 2684528 A1 | 1/2014 |
| EP | 2123225 B1 | 12/2014 |
| EP | 2815705 A1 | 12/2014 |
| EP | 2881046 A2 | 10/2015 |
| EP | 2937047 A1 | 10/2015 |
| JP | S59059371 A | 4/1984 |
| JP | S61165061 A | 7/1986 |
| JP | S62068293 A | 3/1987 |
| JP | H04144533 A | 5/1992 |
| JP | 05-115425 | 5/1993 |
| JP | 2006508049 | 9/1994 |
| JP | H06507809 A | 9/1994 |
| JP | H06508049 A | 9/1994 |
| JP | 07-016235 | 1/1995 |
| JP | 07-136173 | 5/1995 |
| JP | 7306155 | 11/1995 |
| JP | 08-224248 | 9/1996 |
| JP | 2001500510 | 1/2001 |
| JP | 2001505810 | 5/2001 |
| JP | 2002000524 A | 1/2002 |
| JP | 2003220065 | 8/2003 |
| JP | 2004144533 | 5/2004 |
| JP | 2004-180781 | 7/2004 |
| JP | 2004283940 A | 10/2004 |
| JP | 2004322310 | 11/2004 |
| JP | 2004329292 | 11/2004 |
| JP | 2006507809 | 3/2006 |
| JP | 2009106606 | 5/2009 |
| JP | 2009297809 A | 12/2009 |
| JP | 2010533045 | 10/2010 |
| JP | 2010536436 | 12/2010 |
| JP | 2011504794 | 2/2011 |
| JP | 2011045500 | 3/2011 |
| JP | 2011115591 | 6/2011 |
| JP | 2012504017 A | 2/2012 |
| JP | 2012176489 A | 9/2012 |
| JP | 5418704 B1 | 2/2014 |
| JP | 2015526171 A | 9/2015 |
| JP | 2016213937 A | 12/2016 |
| JP | 2017113837 A | 6/2017 |
| WO | 199221291 | 5/1991 |
| WO | 2001089405 | 11/2001 |
| WO | 2002082979 | 10/2002 |
| WO | 2002100256 | 12/2002 |
| WO | 2005009211 | 7/2004 |
| WO | 2005044095 | 5/2005 |
| WO | 2006052927 | 8/2005 |
| WO | 2006005075 | 1/2006 |
| WO | 2006079108 | 1/2006 |
| WO | 2006079108 | 7/2006 |
| WO | 2007011654 | 1/2007 |
| WO | 2007111571 | 10/2007 |
| WO | 2007149559 | 12/2007 |
| WO | 2009014917 A2 | 1/2009 |
| WO | 2009023851 | 2/2009 |
| WO | 2009144729 | 12/2009 |
| WO | 2009158164 A1 | 12/2009 |
| WO | 2010039394 A1 | 4/2010 |
| WO | 2010042611 A1 | 4/2010 |
| WO | 2010046823 A1 | 4/2010 |
| WO | 2010050771 | 5/2010 |
| WO | 2010083480 A2 | 7/2010 |
| WO | 2011075693 | 6/2011 |

(56) References Cited

FOREIGN PATENT DOCUMENTS

| WO | 2011118646 | | 9/2011 |
|---|---|---|---|
| WO | 2011135503 | | 11/2011 |
| WO | 2011163520 | A2 | 12/2011 |
| WO | 2013009887 | | 1/2013 |
| WO | 2013052137 | A2 | 4/2013 |
| WO | 2013106569 | A2 | 7/2013 |
| WO | 2014011238 | | 1/2014 |
| WO | 2014025399 | A1 | 2/2014 |
| WO | 2014144220 | A1 | 9/2014 |
| WO | 2014146090 | A1 | 9/2014 |
| WO | 2015009949 | A2 | 1/2015 |
| WO | 2015031777 | A1 | 3/2015 |
| WO | 2015088655 | A1 | 6/2015 |
| WO | 2016077478 | A1 | 5/2016 |
| WO | 2017024081 | A1 | 2/2017 |
| WO | 2017064303 | A1 | 4/2017 |
| WO | 2017201310 | A1 | 11/2017 |
| WO | 2018045036 | A1 | 3/2018 |

OTHER PUBLICATIONS

Franklin et al., "Prospective Comparison of Open vs. Laparoscopic Colon Surgery for Carcinoma: Five-Year Results," Dis Colon Rectum, 1996; 39: S35-S46.
Flynn et al, "Tomorrow's surgery: micromotors and microrobots for minimally invasive procedures," Minimally Invasive Surgery & Allied Technologies, 1998; 7(4): 343-352.
Fireman et al., "Diagnosing small bowel Crohn's desease with wireless capsule endoscopy," Gut 2003; 52: 390-392.
Fearing et al., "Wing Transmission for a Micromechanical Flying Insect," Proceedings of the 2000 IEEE International Conference to Robotics & Automation, Apr. 2000; 1509-1516.
Faraz et al., "Engineering Approaches to Mechanical and Robotic Design for Minimaly Invasive Surgery (MIS)," Kluwer Academic Publishers (Boston), 2000, 13pp.
Falcone et al., "Robotic Surgery," Clin. Obstet. Gynecol. 2003, 46(1): 37-43.
Fraulob et al., "Miniature assistance module for robot-assisted heart surgery," Biomed. Tech. 2002, 47 Suppl. 1, Pt. 1: 12-15.
Fukuda et al., "Mechanism and Swimming Experiment of Micro Mobile Robot in Water," Proceedings of the 1994 IEEE International Conference on Robotics and Automation, 1994: 814-819.
Fukuda et al., "Micro Active Catheter System with Multi Degrees of Freedom," Proceedings of the IEEE International Conference on Robotics and Automation, May 1994, pp. 2290-2295.
Fuller et al., "Laparoscopic Trocar Injuries: A Report from a U.S. Food and Drug Administration (FDA) Center for Devices and Radiological Health (CDRH) Systematic Technology Assessment of Medical Products (STAMP) Committe," U.S. Food and Drug Adminstration, available at http://www.fdaJ:?;ov, Finalized: Nov. 7, 2003; Updated: Jun. 24, 2005, 11 pp.
Dumpert et al., "Improving in Vivo Robot Visioin Quality," from the Proceedings of Medicine Meets Virtual Realtiy, Long Beach, CA, Jan. 26-29, 2005. 1 pg.
Dakin et al., "Comparison of laparoscopic skills performance between standard instruments and two surgical robotic systems," Surg Endosc., 2003; 17: 574-579.
Cuschieri, "Technology for Minimal Access Surgery," BMJ, 1999, 319: 1-6.
Grady, "Doctors Try New Surgery for Gallbladder Removal," The New York Times, Apr. 20, 2007, 3 pp.
Choi et al., "Flexure-based Manipulator for Active Handheld Microsurgical Instrument," Proceedings of the 27th Annual International Conference of the IEEE Engineering in Medicine and Biology Society (EMBS), Sep. 2005, 4pp.
Chanthasopeephan et al., (2003), "Measuring Forces in Liver Cutting: New Equipment and Experimenal Results," Annals of Biomedical Engineering 31: 1372-1382.
Cavusoglu et al., "Robotics for Telesurgery: Second Generation Berkeley/UCSF Laparoscopic Telesurgical Workstation and Looking Towards the Future Applications," Industrial Robot: An International Journal, 2003; 30(1): 22-29.
Guber et al., "Miniaturized Instrument Systems for Minimally Invasive Diagnosis and Therapy," Biomedizinische Technic. 2002, Band 47, Erganmngsband 1: 198-201.
Abbott et al., "Design of an Endoluminal NOTES Robotic System," from the Proceedings of the 2007 IEEE/RSJ Int'l Conf. on Intelligent Robot Systems, San Diego, CA, Oct. 29-Nov. 2, 2007, pp. 410-416.
Allendorf et al., "Postoperative Immune Function Varies Inversely with the Degree of Surgical Trauma in a Murine Model," Surgical Endoscopy 1997; 11:427-430.
Ang, "Active Tremor Compensation in Handheld Instrument for Microsurgery," Doctoral Dissertation, tech report Cmu- RI-TR-04-28, Robotics Institute, Carnegie Mellon Unviersity, May 2004, 167pp.
Atmel 80C5X2 Core, http://www.atmel.com, 2006, 186pp.
Bailey et al., "Complications of Laparoscopic Surgery," Quality Medical Publishers, Inc., 1995, 25pp.
Ballantyne, "Robotic Surgery, Telerobotic Surgery, Telepresence, and Telementoring," Surgical Endoscopy, 2002; 16: 1389-1402.
Bauer et al., "Case Report: Remote Percutaneous Renal Percutaneous Renal Access Using a New Automated Telesurgical Robotic System," Telemedicine Journal and e-Health 2001; (4): 341-347.
Begos et al., "Laparoscopic Cholecystectomy: From Gimmick to Gold Standard," J Clin Gastroenterol, 1994; 19(4): 325-330.
Berg et al., "Surgery with Cooperative Robots," Medicine Meets Virtual Reality, Feb. 2007, 1 pg.
Breda et al., "Future developments and perspectives in laparoscopy," Eur. Urology 2001; 40(1): 84-91.
Breedveld et al., "Design of Steerable Endoscopes to Improve the Visual Perception of Depth During Laparoscopic Surgery," ASME, Jan. 2004; vol. 126, pp. 1-5.
Breedveld et al., "Locomotion through the Intestine by means of Rolling Stents," Proceedings of the ASME Design Engineering Technical Conferences, 2004, pp. 1-7.
Calafiore et al., Multiple Arterial Conduits Without Cardiopulmonary Bypass: Early Angiographic Results,: Ann Thorac Surg, 1999; 67: 450-456.
Camarillo et al., "Robotic Technology in Surgery: Past, Present and Future," The American Journal of Surgery, 2004; 188: 28-15.
Cavusoglu et al., "Telesurgery and Surgical Simulation: Haptic Interfaces to Real and Virtual Surgical Environments," In Mclaughlin, M.L., Hespanha, J.P., and Sukhatme, G., editors. Touch in virtual environments, IMSC Series in Multimedia 2001, 28pp.
Dumpert et al., "Stereoscopic In Vivo Surgical Robots," IEEE Sensors Special Issue on In Vivo Sensors for Medicine, Jan. 2007, 10 pp.
Green, "Telepresence Surgery", Jan. 1, 1995, Publisher: IEEE Engineering in Medicine and Biology.
Cleary et al., "State of the Art in Surgical Rootics: Clinical Applications and Technology Challenges", "Computer Aided Surgery", Jan. 1, 2002, pp. 312-328, vol. 6.
Stoianovici et al., "Robotic Tools for Minimally Invasive Urologic Surgery", Jan. 1, 2002, pp. 1-17.
Lehman et al., Dexterous miniature in vivo robot for NOTES, 2009, IEEE, p. 244-249.
Mihelj et al., ARMin II—7 DoF rehabilitation robot: mechanics and kinematics, 2007, IEEE, p. 4120-4125.
Zhang et al., Cooperative robotic assistant for laparoscopic surgery: CoBRASurge, 2009, IEEE, p. 5540-5545.
Abbou et al., "Laparoscopic Radical Prostatectomy with a Remote Controlled Robot," The Journal of Urology, Jun. 2001; 165: 1964-1966.
Albers et al., Design and development process of a humanoid robot upper body through experimentation, 2004, IEEE, p. 77-92 (Year: 2004).
Crystal Eyes, http://www.reald.com, 2007 (Stereo 3D visualization for CAVEs, theaters and immersive environments), 1 pg.
Definition of Individually. Dictionary.com, retrieved on Aug. 9, 2016; Retrieved from the Internet: <http://www.dictionary.com/browse/individually>, 1 page.

(56) References Cited

OTHER PUBLICATIONS

Glukhovsky et al., "The development and application of wireless capsule endoscopy," Int. J. Med. Robot. Comput. Assist. Surgery, 2004; 1(1): 114-123.
Gong et al., "Wireless endoscopy," Gastrointestinal Endoscopy 2000; 51 (6): 725-729.
Gopura et al., Mechanical designs of active upper-limb exoskeleton robots: State-of-the-art and design difficulties, 2009, IEEE, p. 178-187 (Year: 2009).
Gopura et al., A brief review on upper extremity robotic exoskeleton systems, 2011, IEEE, p. 346-351 (Year: 2011).
Guo et al., "Micro Active Guide Wire Catheter System—Characteristic Evaluation, Electrical Model* and Operability Evaluation of Micro Active Catheter," Proceedings of the 1996 IEEE International Conference on Robotics and Automation, Apr. 1996; 2226-2231.
Guo et al., "Fish-like Underwater Microrobot with 3 DOF," Proceedings of the 2002 IEEE International Conference on Robotics & Automation, May 2002; 738-743.
Hanly et al., "Robotic Abdominal Surgery," The American Journal of Surgery, 2004; 188 (Suppl. to Oct. 1994); 19S-26S.
Hanly et al., "Value of the SAGES Learning Center in introducing new technology," Surgical Endoscopy, 2004; 19(4): 477-483.
Heikkinen et al., "Comparison of laparoscopic and open Nissen fundoplication two years after operation: A prospective randomized trial," Surgical Endoscopy, 2000; 14:1019-1023.
Hissink, "Olympus Medical develops capsule camera technology," Dec. 2004, accessed Aug. 29, 2007, http://www.letsgodigital.org, 3 pp.
Horgan et al., "Technical Report: Robots in Laparoscopic Surgery," Journal of Laparoendoscopic & Advanced Surgical Techniques, 2001; 11(6): 415-419.
Ishiyama et al., "Spiral-type Micro-machine for Medical Applications," 2000 International Symposium on Micromechatronics and Human Science, 2000; 65-69.
Jagannath et al., "Peroral transgastric endoscopic ligation of fallopian tubes with long-term survival in a porcine model," Gastrointestinal Endoscopy, 2005; 61 (3): 449-453.
Kalloo et al., "Flexible transgastric peritoneoscopy: a novel approach to diagnostic and therapeutic interventions in the peritoneal cavity," Gastrointestinal Endoscopy, 2004; 60(1): 114-117.
Kang et al., "Robotic Assistants Aid Surgeons During Minimally Invasive Procedures," IEEE Engineering in Medicine and Biology, Jan.-Feb. 2001: 94-104.
Kantsevoy et al., "Transgastric endoscopic splenectomy," Surgical Endoscopy, 2006; 20: 522-525.
Kantsevoy et al., "Endoscopic gastrojejunostomy with survival in a porcine model," Gastrointestinal Endoscopy, 2005; 62(2): 287-292.
Kazemier et al. (1998), "Vascular Injuries During Laparoscopy," J. Am. Coll. Surg. 186(5): 604-5.
Keller et al., Design of the pediatric arm rehabilitation robot ChARMin, 2014, IEEE, p. 530-535 (Year: 2014).
Kim, "Early Experience with Telemanipulative Robot-Assisted Laparoscopic Cholecystectomy Using da Vinci," Surgical Laparoscopy, Endoscopy & Percutaneous Techniques, 2002; 12(1): 33-40.
Ko et al., "Per-Oral transgastric abdominal surgery," Chinese Journal of Digestive Diseases, 2006; 7: 67-70.
Lafullarde et al., "Laparoscopic Nissen Fundoplication: Five-year Results and Beyond," Arch/Surg, Feb. 2001; 136: 180-184.
Leggett et al. (2002), "Aortic injury during laparoscopic Fundoplication," Surg. Endoscopy 16(2): 362.
Li et al. (2000), "Microvascular Anastomoses Performed in Rats Using a Microsurgical Telemanipulator," Comp. Aid. Surg., 5: 326-332.
Liem et al., "Comparison of Conventional Anterior Surgery and Laparoscopic Surgery for Inguinal-hernia Repair," New England Journal of Medicine, 1997; 336 (22):1541-1547.

Lou Cubrich, "A Four-DOF Laparo-Endoscopic Single Site Platform for Rapidly-Developing Next Generation Surgical Robotics", Journal of Medical Robotics Research, vol. 1, No. 4, 2016, 165006-1-165006-15.
Macfarlane et al., "Force-Feedback Grasper Helps Restore the Sense of Touch in Minimally Invasive Surgery," Journal of Gastrointestinal Surgery, 1999; 3: 278-285.
Mack et al., "Present Role of Thoracoscopy in the Diagnosis and Treatment of Diseases of the Chest," Ann Thorac Surgery, 1992; 54: 403-409.
Mack, "Minimally Invasive and Robotic Surgery," JAMA, Feb. 2001; 285(5): 568-572.
Mei et al., "Wireless Drive and Control of a Swimming Microrobot," Proceedings of the 2002 IEEE International Conference on Robotics & Automation, May 2002: 1131-1136.
Menciassi et al., "Robotic Solutions and Mechanisms for a Semi-Autonomous Endoscope," Proceedings of the 2002 IEEE/RSJ Intl. Conference on Intelligent Robots and Systems, Oct. 2002; 1379-1384.
Melvin et al., "Computer-Enhanced vs. Standard Laparoscopic Antireflux Surgery," J Gastrointest Surg 2002; 6: 11-16.
Leggedmenciassi et al., "Locomotion of a Legged Capsule in the Gastrointestinal Tract: Theoretical Study and Preliminary Technological Results," IEEE Int. Conf. on Engineering in Medicine and Biology, San Francisco, CA, pp. 2767-2770, Sep. 2004.
Menciassi et al., "Shape memory alloy clamping devices of a capsule for monitoring tasks in the gastrointestinal tract," J. Micromech. Microeng, 2005; 15: 2045-2055.
Meron, "The development of the swallowable video capsule (M2A)," Gastrointestinal Endoscopy 2000; 52 6: 817-819.
Micron, http://www.micron.com, 2006, ¼-inch VGA NTSC/PAL CMOS Digital Image Sensor, 98 pp.
Midday Jeff et al., "Material Handling System for Robotic natural Orifice Surgery,", Proceedings of the 2011 Design of medical Devices Conference, Apr. 12-14, 2011, Minneapolis, MN 4 pages.
Miller, Ph.D., et al., "In-Vivo Stereoscopic Imaging System with 5 Degrees-of-Freedom for Minimal Access Surgery," Dept. of Computer Science and Dept. of Surgery, Columbia University, New York, NY, 7 pp., 2004.
Munro (2002), "Laparoscopic access: complications, technologies, and techniques," Curro Opin. Obstet. Gynecol., 14 (4): 365-74.
Nio et al., "Efficiency of manual vs robotical (Zeus) assisted laparoscopic surgery in the performance of standardized tasks," Surg Endosc, 2002; 16: 412-415.
Oleynikov et al., "In Vivo Camera Robots Provide Improved Vision for Laparoscopic Surgery," Computer Assisted Radiology and Surgery (CARS), Chicago, IL, Jun. 23-26, 2004b.
Oleynikov et al., "Miniature Robots Can Assist in Laparoscopic Cholecystectomy," Journal of Surgical Endoscopy, 19-4: 473-476, 2005.
Oleynikov et al., "In Vivo Robotic Laparoscopy," Surgical Innovation, Jun. 2005, 12(2): 177-181.
O'Neill, "Surgeon takes new route to gallbladder," The Oregonian, Jun. 2007; 2 pp.
Orlando et al. (2003), "Needle and Trocar Injuries in Diagnostic Laparoscopy under Local Anesthesia: What Is the True Incidence of These Complications?" Journal of Laparoendoscopic & Advanced Surgical Techniques, 13(3): 181-184.
Palm. William. "Rapid Prototyping Primer" May 1998 (revised Jul. 30, 2002) (http://www.me.psu.edu/lamancusa/rapidpro/primer/chapter2.htm), 12 pages.
Park et al., "Experimental studies of transgastric gallbladder surgery: cholecystectomy and cholecystogastric anastomosis (videos)," Gastrointestinal Endoscopy, 2005; 61 (4): 601-606.
Park et al., "Trocar-less Instrumentation for Laparoscopy: Magnetic Positioning of Intra-abdominal Camera and Retractor," Ann Surg, Mar. 2007; 245(3): 379-384.
Patronik et al., "Crawling on the Heart: A Mobile Robotic Device for Minimally Invasive Cardiac Interventions," MICCAI, 2004, pp. 9-16.
Patronik et al., "Development of a Tethered Epicardial Crawler for Minimally Invasive Cardiac Therapies," IEEE, pp. 239-240, 2004.

(56) References Cited

OTHER PUBLICATIONS

Patronik et al., "Preliminary evaluation of a mobile robotic device for navigation and intervention on the beating heart," Computer Aided Surgery, 10(4): 225-232, Jul. 2005.
Peirs et al., "A miniature manipulator for integration in a self-propelling endoscope," Sensors and Actuators A, 2001, 92: 343-349.
Peters, "Minimally Invasive Colectomy: Are the Potential Benefits Realized?" Dis Colon Rectum 1993; 36: 751-756.
Phee et al., "Development of Microrobotic Devices for Locomotion in the Human Gastrointestinal Tract," International Conference on Computational Intelligence, Robotics and Autonomous Systems (CIRAS 2001), Nov. 28-30, (2001), Singapore, 6 pages.
Phee et al., "Analysis and Development of Locomotion Devices for the Gastrointestinal Tract," IEEE Transactions on Biomedical Engineering, vol. 49, No. 6, Jun. 2002: 613-616.
Platt et al., "In Vivo Robotic Cameras can Enhance Imaging Capability During Laparoscopic Surgery," from the Proceedings of the Society of American Gastrointestinal Endoscopic Surgeons (SAGES) Scientific Conference, Ft. Lauderdale, FL, Apr. 13-16, 2005; 1 pg.
Qian Huan et al., "Multi-joint Single-wound Minimally Invasive Abdominal Surgery Robot Design," Mechanical Design and Manufacturing, May 8, 2014, pp. 134-137.
Rentschler et al., "In vivo Mobile Surgical Robotic Task Assistance," 1 pg.
Rentschler et al., "Theoretical and Experimental Analysis of In Vivo Wheeled Mobility," ASME Design Engineering Technical Conferences: 28th Biennial Mechanisms and Robotics Conference, Salt Lake City, Utah, Sep. 28-Oct. 2, 2004; pp. 1-9.
Rentschler et al., "In Vivo Robots for Laparoscopic Surgery," Studies in Health Technology and Infonnatics—Medicine Meets Virtual Reality, ISO Press, Newport Beach, CA, 2004a, 98: 316-322.
Rentschler et al., "Toward In Vivo Mobility," Studies in Health Technology and Infonnatics—Medicine Meets Virtual Reality, ISO Press, Long Beach, CA, 2005a, III: 397-403.
Rentschler et al., "Mobile In Vivo Robots Can Assist in Abdominal Exploration," from the Proceedings of the Society of American Gastrointestinal Endoscopic Surgeons (SAGES) Scientific Conference, Ft. Lauderdale, FL, April 13-16, 2005b.
Rentschler et al., "Modeling, Analysis, and Experimental Study of In Vivo Wheeled Robotic Mobility," IEEE Transactions on Robotics, 22 (2): 308-321, 2005c.
Rentschler et al., "Miniature in vivo robots for remote and harsh environments," IEEE Transaction on Information Technology in Biomedicine, Jan. 2006; 12(1): pp. 66-75.
Rentschler et al., "Mechanical Design of Robotic In Vivo Wheeled Mobility," ASME Journal of Mechanical Design, 2006a; pp. 1-11, Accepted.
Rentschler et al., "Mobile In Vivo Camera Robots Provide Sole Visual Feedback for Abdominal Exploration and Cholecystectomy," Journal of Surgical Endoscopy, 20-1: 135-138, 2006b.
Rentschler et al., "Natural Orifice Surgery with an Endoluminal Mobile Robot," The Society of American Gastrointestinal Endoscopic Surgeons, Dallas, TX, April 2006d.
Rentschler et al., "Mobile In Vivo Biopsy and Camera Robot," Studies in Health and Infonnatics Medicine Meets Virtual Reality, vol. 119: 449-454, IOS Press, Long Beach, CA, 2006e.
Rentschler et al., "Mobile In Vivo Biopsy Robot," IEEE International Conference on Robotics and Automation, Orlando, Florida, May 2006; 4155-4160.
Rentschler et al., "In vivo Robotics during the NEEMO 9 Mission," Medicine Meets Virtual Reality, Feb. 2007; 1 pg.
Rentschler et al., "An In Vivo Mobile Robot for Surgical Vision and Task Assistance," Journal of Medical Devices, Mar. 2007; vol. 1: 23-29.
Riviere et al., "Toward Active Tremor Canceling in Handheld Microsurgical Instruments," IEEE Transactions on Robotics and Automation, Oct. 2003, 19(5): 793-800.

Rosen et al., "Force Controlled and Teleoperated Endoscopic, Grasper for Minimally Invasive Surgery-Experimental Performance Evaluation," IEEE Transactions of Biomedical Engineering, Oct. 1999; 46(10): 1212-1221.
Rosen et al., "Task Decomposition of Laparoscopic Surgery for Objective Evaluation of Surgical Residents' Learning Curve Using Hidden Markov Model," Computer Aided Surgery, vol. 7, pp. 49-61, 2002.
Rosen et al., "The Blue DRAGON—A System of Measuring the Kinematics and the Dynamics of Minimally Invasive Surgical Tools In-Vivo," Proc. of the 2002 IEEE International Conference on Robotics and Automation, Washington, DC, pp. 1876-1881, May 2002.
Rosen et al., "Spherical Mechanism Analysis of a Surgical Robot for Minimally Invasive Surgery—Analytical and Experimental Approaches," Studies in Health Technology and Infonnatics-Medicine Meets Virtual Reality, pp. 442-448, Jan. 2005.
Ruurda et al., "Feasibility of Robot-Assisted Laparoscopic Surgery," Surgical Laparoscopy, Endoscopy & Percutaneous Techniques, 2002; 12(1):41-45.
Ruurda et al, "Robot-Assisted surgical systems: a new era in laparoscopic surgery," Ann R. Coll Surg Engl. 2002; 84: 223-226.
Sackier et al., "Robotically assisted laparoscopic surgery," Surgical Endoscopy, 1994; 8:63-6.
Salky, "What is the Penetration of Endoscopic Techniques into Surgical Practice?" Digestive Surgery 2000; 17:422-426.
Satava, "Surgical Robotics: The Early Chronicles," Surgical Laparoscopy, Endoscopy & Percutaneous Techniques, 2002; 12(1):6-16.
Schippers et al. (1996), "Requirements and Possibilities of Computer-Assisted Endoscopic Surgery," In: Computer Integrated Surgery: Technology and Clinical Applications, pp. 561-565.
Schurr et al., "Robotics and Telemanipulation Technologies for Endoscopic Surgery," Surgical Endoscopy, 2000; 14:375-381.
Schwartz, "In the Lab: Robots that Slink and Squirm," The New York Times, Mar. 27, 2007, 4 pp.
Sharp LL-151-3D, http://www.sharp3d.com, 2006, 2 pp.
Slatkin et al., "The Development of a Robotic Endoscope," Proceedings of the 1995 IEEE International Conference on Robotics and Automation, pp. 162-171, 1995.
Smart Pill "Fastastic Voyage: Smart Pill to Expand Testing," http://www.smartpilldiagnostics.com, Apr. 13, 2005, 1 pg.
Sodeyama et al., A shoulder structure of muscle-driven humanoid with shoulder blades, 2005, IEEE, p. 1-6 (Year: 2005).
Southern Surgeons Club (1991), "A prospective analysis of 1518 laparoscopic cholecystectomies," N. Eng. 1 Med. 324 (16): 1073-1078.
Stefanini et al., "Modeling and Experiments on a Legged Microrobot Locomoting in a Tubular Compliant and Slippery Environment," Int. Journal of Robotics Research, vol. 25, No. 5-6, pp. 551-560, May-Jun. 2006.
Stiff et al., "Long-term Pain: Less Common After Laparoscopic than Open Cholecystectomy," British Journal of Surgery, 1994; 81: 1368-1370.
Strong et al., "Efficacy of Novel Robotic Camera vs. a Standard Laproscopic Camera," Surgical Innovation vol. 12, No. 4, Dec. 2005, Westminster Publications, Inc., pp. 315-318.
Suzumori et al., "Development of Flexible Microactuator and its Applications to Robotics Mechanisms," Proceedings of the IEEE International Conference on Robotics and Automation, 1991: 1622-1627.
Taylor et al., "A Telerobotic Assistant for Laparoscopic Surgery," IEEE Eng Med Biol, 1995; 279-87.
Tendick et al. (1993), "Sensing and Manipulation Problems in Endoscopic Surgery: Experiment, Analysis, and Observation," Presence 2(1): 66-81.
Tendick et al., "Applications of Micromechatronics in Minimally Invasive Surgery," IEEE/ASME Transactions on Mechatronics, 1998; 3(1): 34-42.
Thomann et al., "The Design of a new type of Micro Robot for the Intestinal Inspection," Proceedings of the 2002 IEEE Intl. Conference on Intelligent Robots and Systems, Oct. 2002: 1385-1390.
U.S. Appl. No. 60/180,960, filed Feb. 2000.
U.S. Appl. No. 60/956,032, filed Aug. 15, 2007.

(56) References Cited

OTHER PUBLICATIONS

U.S. Appl. No. 60/983,445, filed Oct. 29, 2007.
U.S. Appl. No. 60/990,062, filed Nov. 26, 2007.
U.S. Appl. No. 60/990,076, filed Nov. 26, 2007.
U.S. Appl. No. 60/990,086, filed Nov. 26, 2007.
U.S. Appl. No. 60/990,106, filed Nov. 26, 2007.
U.S. Appl. No. 60/990,470, filed Nov. 27, 2007.
U.S. Appl. No. 61/025,346, filed Feb. 1, 2008.
U.S. Appl. No. 61/030,588, filed Feb. 22, 2008.
U.S. Appl. No. 61/030,617, filed Feb. 22, 2008.
Worn et al., "Espirit Project No. 33915: Miniaturised Robot for Micro Manipulation (MINIMAN)," Nov. 1998, http://www.ipr.ira.ujka.de/-microbot/miniman.
Way et al., editors, "Fundamentals of Laparoscopic Surgery," Churchill Livingstone Inc., 1995; 14 pp.
Wolfe et al. (1991), Endoscopic Cholecystectomy: An analysis of Complications, Arch. Surg. 1991; 126: 1192-1196.
Xu et al., "System Design of an Insertable Robotic Effector Platform for Single Access (SPA) Surgery", The 2009 IEEE/RSJ International Conference on Intelligent Robots and Systems, Oct. 11-15, 2009, St. Louis MO USA pp. 5546-5552.
Yu, BSN, RN, "M2ATM Capsule Endoscopy A Breakthrough Diagnostic Tool for Small Intestine Imagining," vol. 25, No. 1, 2001, Gastroenterology Nursing, pp. 24-27.
Yu et al., "Microrobotic Cell Injection," Proceedings of the 2001 IEEE International Conference on Robotics and Automation, May 2001: 620-625.

* cited by examiner

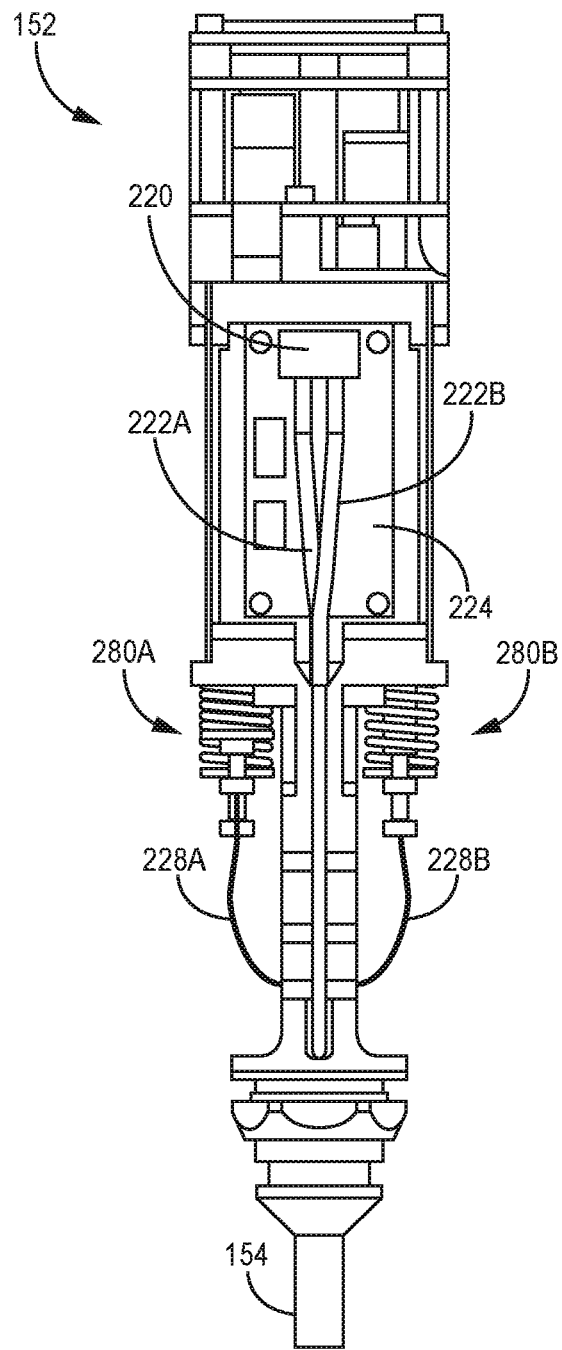 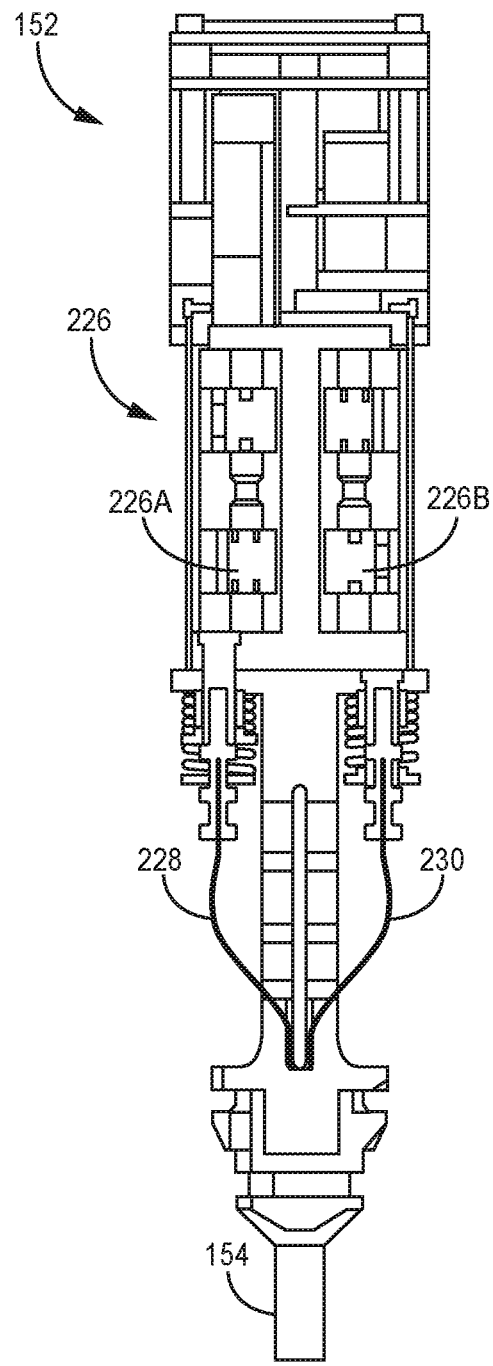
FIG. 10A  FIG. 10B

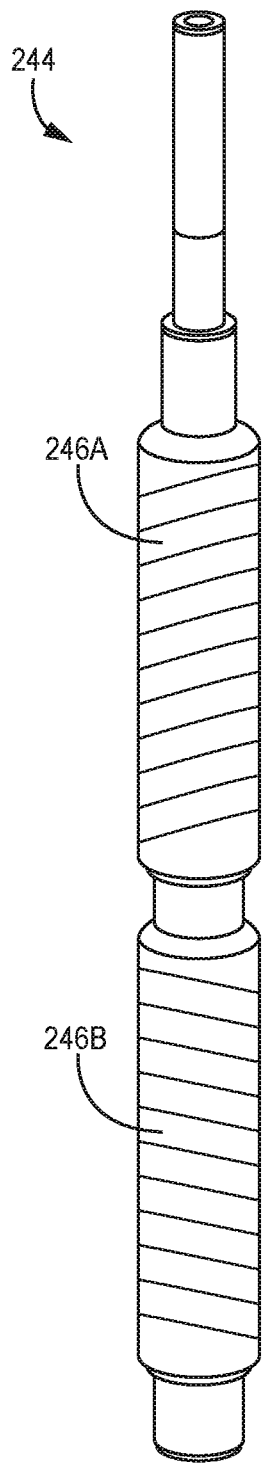
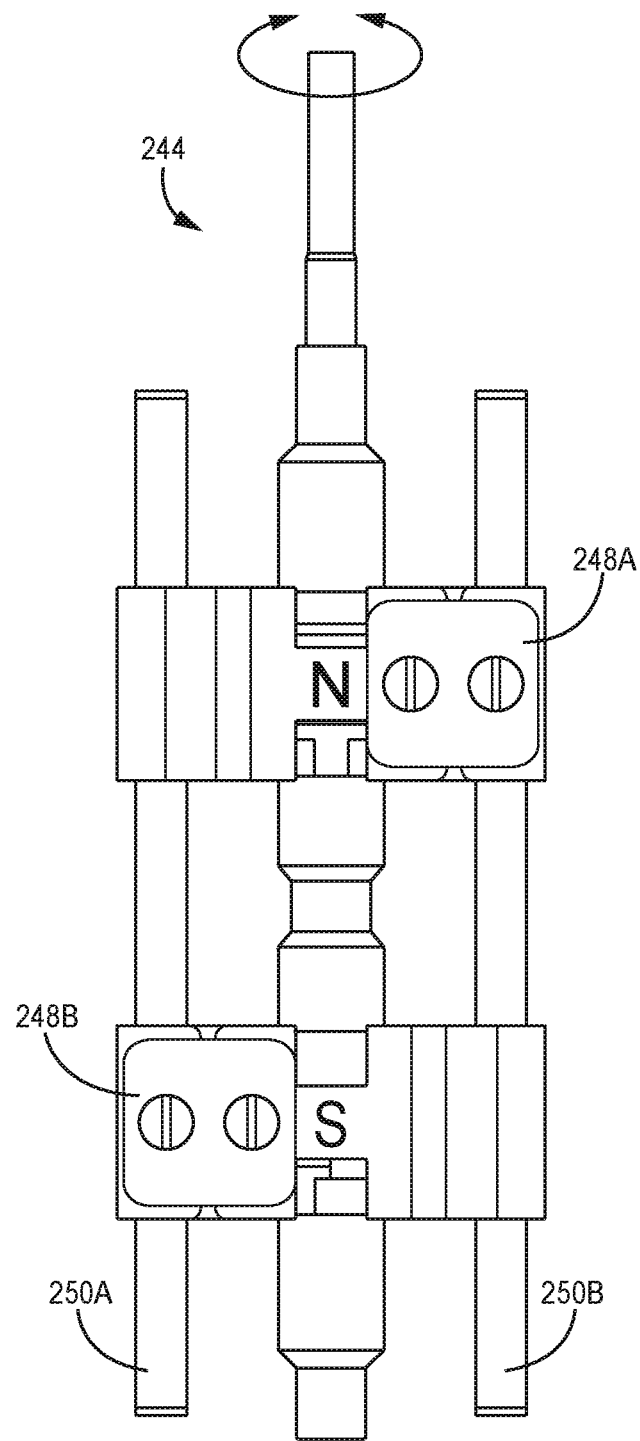
FIG. 10D  FIG. 10E

ROBOTICALLY ASSISTED SURGICAL SYSTEM AND RELATED DEVICES AND METHODS

CROSS-REFERENCE TO RELATED APPLICATION(S)

This application claims the benefit under 35 U.S.C. § 119(e) to U.S. Provisional Application 62/789,029, filed Jan. 7, 2019 and entitled "Robotically Assisted Surgical System," which is hereby incorporated herein by reference in its entirety.

FIELD

The embodiments disclosed herein relate to various medical devices and related components that can make up a surgical system, including robotic and/or in vivo medical devices and related components. Certain embodiments include various robotic medical devices, including robotic devices that are disposed within a body cavity and positioned using a body or support component disposed through an orifice or opening in the body cavity. Other embodiments relate to various systems that have a robotic surgical device and a controller, wherein the device has one or more sensors and the controller has one or more motors such that the sensors transmit information that is used at the controller to actuate the motors to provide haptic feedback to a user.

BACKGROUND

Invasive surgical procedures are essential for addressing various medical conditions. When possible, minimally invasive procedures such as laparoscopy are preferred.

However, known minimally invasive technologies such as laparoscopy are limited in scope and complexity due in part to 1) mobility restrictions resulting from using rigid tools inserted through access ports, and 2) limited visual feedback. Known robotic systems such as the da Vinci® Surgical System (available from Intuitive Surgical, Inc., located in Sunnyvale, CA) are also restricted by the access ports, as well as having the additional disadvantages of being very large, very expensive, unavailable in most hospitals, and having limited sensory and mobility capabilities.

There is a need in the art for improved surgical methods, systems, and devices.

BRIEF SUMMARY

Discussed herein are various robotic surgical systems having various robotic devices. Certain of the robotic devices have coupleable connection ports (also referred to as "nests") that receive and couple to various camera assemblies. The various connection ports herein can have coupling mechanisms therein for coupling to the robotic device and/or the camera assembly. In addition, certain ports have presence detection mechanisms as well. Further discussed herein are camera assemblies with actuation mechanisms for actuating movement of the steerable distal tip thereof.

In Example 1, a robotic surgical system comprises a robotic surgical device and a removable camera component. The robotic surgical device comprises an elongate device body comprising a distal end and a proximal end, a removable connection port disposed at the proximal end of the device body, and first and second robotic arms operably coupled to the distal end of the device body. The connection port comprises a device body coupling mechanism disposed within the connection port, a camera receiving opening defined in a proximal end of the connection port; a seal package disposed in the removable connection port, the seal package comprising at least two seals; and a camera coupling mechanism disposed within the removable connection port. The removable camera component is removably disposable in the camera receiving opening and through the seal package, the removable camera component comprising a camera body, an elongate camera tube, a flexible section, and a distal imager.

Example 2 relates to the robotic surgical system according to Example 1, wherein the device body coupling mechanism comprises first and second hinged coupling mechanisms hingedly coupled to the connection port.

Example 3 relates to the robotic surgical system according to Example 2, wherein each of the first and second hinged coupling mechanisms comprises a coupling mechanism body, a tensioned hinge at a proximal end of the coupling mechanism body, wherein the tensioned hinge is hingedly coupled to the connection port, a coupleable structure at a distal end of the coupling mechanism, wherein the coupleable structure comprises at least one coupling feature configured to be coupleable with a matching coupling feature on the proximal end of the device body and an actuable button.

Example 4 relates to the robotic surgical system according to Example 1, wherein the elongate device body comprises a male connector disposed at a proximal end of the elongate device body, wherein the male connector is coupleable with the connection port.

Example 5 relates to the robotic surgical system according to Example 1, wherein the removable connection port further comprises a presence detection mechanism operably coupled to the camera coupling mechanism.

Example 6 relates to the robotic surgical system according to Example 1, wherein the camera coupling mechanism comprises a slidable body disposed within the connection port, a camera receiving opening defined within the slidable body, an actuable camera release button attached to a first end of the slidable body, and a tensioned spring operably coupled to a second end of the slidable body.

Example 7 relates to the robotic surgical system according to Example 6, wherein the slidable body is slidable along a plane substantially transverse to a longitudinal axis of the elongate device body.

Example 8 relates to the robotic surgical system according to Example 1, further comprising a presence detection mechanism comprising a rotatable lever operably coupled to the camera coupling mechanism at a pivot point, wherein the rotatable lever rotates around the pivot point, a first sensing component disposed on the rotatable lever, and a second sensing component disposed on the elongate body, wherein the second sensing component is configured to sense the presence or absence of the first sensing component.

Example 9 relates to the robotic surgical system according to Example 8, wherein the first sensing component is a magnet.

In Example 10, a removable connection port for a robotic surgical device comprises a connection port body, a distal opening defined at a distal end of the port body, wherein the distal opening is sized and shaped to receive a proximal end of an elongate device body, a proximal opening defined at a proximal end of the port body, wherein the proximal opening is sized and shaped to receive a camera assembly, a seal package disposed in the connection port body, the seal package comprising at least two seals configured to receive a shaft of a camera assembly, a device body coupling mechanism disposed within the connection port body, the device body coupling mechanism comprising first and second hinged coupling mechanisms hingedly coupled to the connection port body, and a camera coupling mechanism disposed within the connection port body. The camera coupling mechanism comprises a slidable body disposed within the connection port body, and a camera receiving opening defined within the slidable body.

Example 11 relates to the removable connection port according to Example 10, wherein each of the first and second hinged coupling mechanisms comprises a coupling mechanism body, a tensioned hinge at a proximal end of the coupling mechanism body, wherein the tensioned hinge is hingedly coupled to the connection port body, and a coupleable structure at a distal end of the coupling mechanism, wherein the coupleable structure comprises at least one coupling feature configured to be coupleable with a matching coupling feature on the proximal end of the elongate device body and an actuable button.

Example 12 relates to the removable connection port according to Example 10, wherein the distal opening is sized and shaped to receive a male connector disposed at the proximal end of the elongate device body.

Example 13 relates to the removable connection port according to Example 10, further comprising a presence detection mechanism operably coupled to the camera coupling mechanism.

Example 14 relates to the removable connection port according to Example 10, wherein the camera coupling mechanism further comprises an actuable camera release button attached to a first end of the slidable body and a tensioned spring operably coupled to a second end of the slidable body.

Example 15 relates to the removable connection port according to Example 10, wherein the slidable body is slidable along a plane substantially transverse to a longitudinal axis of a lumen of the seal package.

Example 16 relates to the removable connection port according to Example 10, further comprising a presence detection mechanism comprising a rotatable lever operably coupled to the camera coupling mechanism at a pivot point, wherein the rotatable lever rotates around the pivot point, and a first sensing component disposed on the rotatable lever, wherein the first sensing component is configured to interact with a second sensing component disposed on the elongate device body when the removable connection port is coupled to the elongate device body.

Example 17 relates to the removable connection port according to Example 16, wherein the first sensing component is a magnet.

In Example 18, a robotic surgical system comprises a robotic surgical device and a removable camera component. The robotic surgical device comprises an elongate device body comprising a distal end and a proximal end, a removable connection port disposed at the proximal end of the device body, and first and second robotic arms operably coupled to the distal end of the device body. The connection port comprises a device body coupling mechanism disposed within the connection port, the device body coupling mechanism comprising first and second hinged coupling mechanisms hingedly coupled to the connection port, an camera receiving opening defined in a proximal end of the connection port, a seal package disposed in the removable connection port, the seal package comprising at least two seals, a camera coupling mechanism disposed within the removable connection port, and a presence detection mechanism operably coupled to the camera coupling mechanism. The camera coupling mechanism comprises a slidable body slidably disposed within the connection port, a camera receiving opening defined within the slidable body, an actuable camera release button attached to a first end of the slidable body, and a tensioned spring operably coupled to a second end of the slidable body. The presence detection mechanism comprises a rotatable lever operably coupled to the camera coupling mechanism at a pivot point, wherein the rotatable lever rotates around the pivot point, a first sensing component disposed on the rotatable lever, and a second sensing component disposed on the elongate body, wherein the second sensing component is configured to sense the presence or absence of the first sensing component. The removable camera component is removably disposable in the camera receiving opening and through the seal package, and the removable camera component comprises a camera body, an elongate camera tube, a flexible section, and a distal imager.

Example 19 relates to the robotic surgical system according to Example 18, wherein each of the first and second hinged coupling mechanisms comprises a coupling mechanism body, a tensioned hinge at a proximal end of the coupling mechanism body, wherein the tensioned hinge is hingedly coupled to the connection port, and a coupleable structure at a distal end of the coupling mechanism, wherein the coupleable structure comprises at least one coupling feature configured to be coupleable with a matching coupling feature on the proximal end of the device body and an actuable button.

Example 20 relates to the robotic surgical system according to Example 18, wherein the slidable body is slidable along a plane substantially transverse to a longitudinal axis of a lumen defined by the at least two seals in the seal package.

In Example 21, a camera assembly for a robotic surgical system comprises an elongate camera shaft, a camera body coupled to a proximal end of the elongate camera shaft, a steerable tip disposed at the distal end of the elongate camera shaft, a first cable coupled at a first end to the first drive carriage and coupled at a second end to the steerable tip, and a second cable coupled at a first end to the second drive carriage and coupled at a second end to the steerable tip. The camera body comprises a distal end configured to be positionable within a robotic device, and at least one actuation mechanism disposed within the camera body. The distal end comprises a distal nose cone disposed around the elongate shaft, and a coupling mechanism acceptance slot defined proximal to the distal nose cone. The at least one actuation mechanism comprises a rotatable shaft, a first drive carriage threadably coupled to the rotatable shaft, and a second drive carriage threadably coupled to the rotatable shaft. The steerable tip comprises a steerable tip body comprising a camera imager and an illumination component, and a flexible section coupled to the elongate camera shaft and the steerable tip body, wherein the steerable tip body is movable in relation to the elongate camera shaft via the flexible section. Further, actuation of the actuation mechanism causes linear movement of the first and second drive carriages in opposite directions, whereby the first and second cables steer the steerable tip.

Example 21 relates to the camera assembly according to Example 21, wherein the camera body further comprises an external housing and a cylindrical heat sink structure, wherein the cylindrical heat sink structure is disposed within the external housing.

While multiple embodiments are disclosed, still other embodiments will become apparent to those skilled in the art from the following detailed description, which shows and describes illustrative embodiments. As will be realized, the various embodiments are capable of modifications in various obvious aspects, all without departing from the spirit and scope thereof. Accordingly, the drawings and detailed description are to be regarded as illustrative in nature and not restrictive.

BRIEF DESCRIPTION OF THE DRAWINGS

FIG. 10A is a cross-sectional side view of the internal components of the camera body of FIG. 9A, according to one embodiment.

FIG. 10B is a cross-sectional front view of the internal components of the camera body of FIG. 9A, according to one embodiment.

FIG. 10D is a perspective view of the lead screw of the actuation mechanism of FIG. 10C, according to one embodiment.

FIG. 10E is a cutaway view of certain components of the actuation mechanism of FIG. 10C, according to one embodiment.

DETAILED DESCRIPTION

Figure 1:
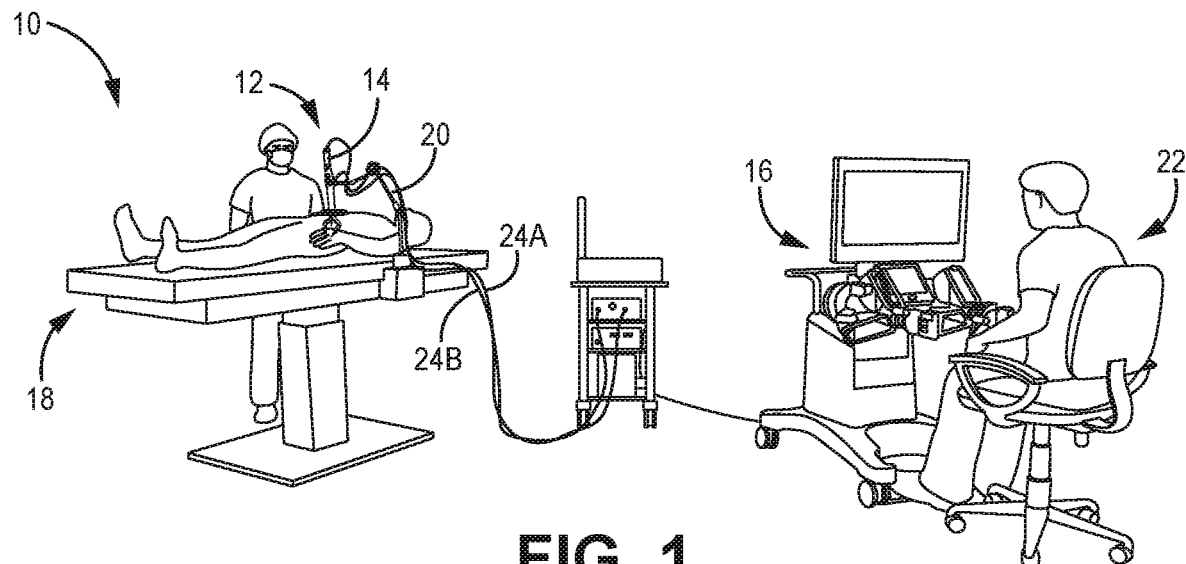
FIG. 1 is a perspective view of a robotic surgical system in an operating room, according to one embodiment.

The various systems and devices disclosed herein relate to devices for use in medical procedures and systems. More specifically, various embodiments relate to various medical devices, including robotic devices and related methods and systems.

It is understood that the various embodiments of robotic devices and related methods and systems disclosed herein can be incorporated into or used with any other known medical devices, systems, and methods.

It is understood that the various embodiments of robotic devices and related methods and systems disclosed herein can be incorporated into or used with any other known medical devices, systems, and methods. For example, the various embodiments disclosed herein may be incorporated into or used with any of the medical devices and systems disclosed in U.S. Pat. No. 8,968,332 (issued on Mar. 3, 2015 and entitled "Magnetically Coupleable Robotic Devices and Related Methods"), U.S. Pat. No. 8,834,488 (issued on Sep. 16, 2014 and entitled "Magnetically Coupleable Surgical Robotic Devices and Related Methods"), U.S. Pat. No. 10,307,199 (issued on Jun. 4, 2019 and entitled "Robotic Surgical Devices and Related Methods"), U.S. Pat. No. 9,579,088 (issued on Feb. 28, 2017 and entitled "Methods, Systems, and Devices for Surgical Visualization and Device Manipulation"), U.S. Patent Application 61/030,588 (filed on Feb. 22, 2008), U.S. Pat. No. 8,343,171 (issued on Jan. 1, 2013 and entitled "Methods and Systems of Actuation in Robotic Devices"), U.S. Pat. No. 8,828,024 (issued on Sep. 9, 2014 and entitled "Methods and Systems of Actuation in Robotic Devices"), U.S. Pat. No. 9,956,043 (issued on May 1, 2018 and entitled "Methods and Systems of Actuation in Robotic Devices"), U.S. patent application Ser. No. 15/966,606 (filed on Apr. 30, 2018 and entitled "Methods, Systems, and Devices for Surgical Access and Procedures"), U.S. patent application Ser. No. 12/192,663 (filed on Aug. 15, 2008 and entitled "Medical Inflation, Attachment, and Delivery Devices and Related Methods"), U.S. patent application Ser. No. 15/018,530 (filed on Feb. 8, 2016 and entitled "Medical Inflation, Attachment, and Delivery Devices and Related Methods"), U.S. Pat. No. 8,974,440 (issued on Mar. 10, 2015 and entitled "Modular and Cooperative Medical Devices and Related Systems and Methods"), U.S. Pat. No. 8,679,096 (issued on Mar. 25, 2014 and entitled "Multifunctional Operational Component for Robotic Devices"), U.S. Pat. No. 9,179,981 (issued on Nov. 10, 2015 and entitled "Multifunctional Operational Component for Robotic Devices"), U.S. Pat. No. 9,883,911 (issued on Feb. 6, 2018 and entitled "Multifunctional Operational Component for Robotic Devices"), U.S. patent application Ser. No. 15/888,723 (filed on Feb. 5, 2018 and entitled "Multifunctional Operational Component for Robotic Devices"), U.S. Pat. No. 8,894,633 (issued on Nov. 25, 2014 and entitled "Modular and Cooperative Medical Devices and Related Systems and Methods"), U.S. Pat. No. 8,968,267 (issued on Mar. 3, 2015 and entitled "Methods and Systems for Handling or Delivering Materials for Natural Orifice Surgery"), U.S. Pat. No. 9,060,781 (issued on Jun. 23, 2015 and entitled "Methods, Systems, and Devices Relating to Surgical End Effectors"), U.S. Pat. No. 9,757,187 (issued on Sep. 12, 2017 and entitled "Methods, Systems, and Devices Relating to Surgical End Effectors"), U.S. Pat. No. 10,350,000 (issued on Jul. 16, 2019 and entitled "Methods, systems, and devices relating to surgical end effectors"), U.S. patent application Ser. No. 16/512,510 (filed on Jul. 16, 2019 and entitled "Methods, Systems, and Devices Relating to Surgical End Effectors"), U.S. Pat. No. 9,089,353 (issued on Jul. 28, 2015 and entitled "Robotic Surgical Devices, Systems, and Related Methods"), U.S. Pat. No. 10,111,711 (issued on Oct. 30, 2018 and entitled "Robotic Surgical Devices, Systems, and Related Methods"), U.S. patent application Ser. No. 16/123,619 (filed on Sep. 6, 2018 and entitled "Robotic Surgical Devices, Systems and Related Methods"), U.S. Pat. No. 9,770,305 (issued on Sep. 26, 2017 and entitled "Robotic Surgical Devices, Systems, and Related Methods"), U.S. patent application Ser. No. 15/661,147 (filed on Jul. 27, 2017 and entitled "Robotic Devices with On Board Control & Related Systems & Devices"), U.S. patent application Ser. No. 13/833,605 (filed on Mar. 15, 2013 and entitled "Robotic Surgical Devices, Systems, and Related Methods"), U.S. patent application Ser. No. 13/738,706 (filed on Jan. 10, 2013 and entitled "Methods, Systems, and Devices for Surgical Access and Insertion"), U.S. patent application Ser. No. 14/661,465 (filed on Mar. 18, 2015 and entitled "Methods, Systems, and Devices for Surgical Access and Insertion"), U.S. patent application Ser. No. 15/890,860 (filed on Feb. 7, 2018 and entitled "Methods, Systems, and Devices for Surgical Access and Insertion"), U.S. Pat. No. 9,498,292 (issued on Nov. 22, 2016 and entitled "Single Site Robotic Devices and Related Systems and Methods"), U.S. Pat. No. 10,219,870 (issued on Mar. 5, 2019 and entitled "Single site robotic device and related systems and methods"), U.S. patent application Ser. No. 16/293,135 (filed Mar. 3, 2019 and entitled "Single Site Robotic Device and Related Systems and Methods"), U.S. Pat. No. 9,010,214 (issued on Apr. 21, 2015 and entitled "Local Control Robotic Surgical Devices and Related Methods"), U.S. Pat. No. 10,470,828 (issued on Nov. 12, 2019 and entitled "Local Control Robotic Surgical Devices and Related Methods"), U.S. patent application Ser. No. 16/596,034 (filed on Oct. 8, 2019 and entitled "Local Control Robotic Surgical Devices and Related Methods"), U.S. Pat. No. 9,743,987 (issued on Aug. 29, 2017 and entitled "Methods, Systems, and Devices Relating to Robotic Surgical Devices, End Effectors, and Controllers"), U.S. patent application Ser. No. 15/687,787 (filed on Aug. 28, 2017 and entitled "Methods, Systems, and Devices Relating to Robotic Surgical Devices, End Effectors, and Controllers"), U.S. Pat. No. 9,888,966 (issued on Feb. 13, 2018 and entitled "Methods, Systems, and Devices Relating to Force Control Surgical Systems"), U.S. patent application Ser. No. 15/894,489 (filed on Feb. 12, 2018 and entitled "Methods, Systems, and Devices Relating to Force Control Surgical Systems"), U.S. patent application Ser. No. 14/212,686 (filed on Mar. 14, 2014 and entitled "Robotic Surgical Devices, Systems, and Related Methods"), U.S. patent application Ser. No. 14/334,383 (filed on Jul. 17, 2014 and entitled "Robotic Surgical Devices, Systems, and Related Methods"), U.S. patent application Ser. No. 14/853,477 (filed on Sep. 14, 2015 and entitled "Quick-Release End Effectors and Related Systems and Methods"), U.S. patent application Ser. No. 16/504,793 (filed on Jul. 8, 2019 and entitled "Quick-Release End Effectors and Related Systems and Methods"), U.S. Pat. No. 10,376,322 (issued on Aug. 13, 2019 and entitled "Robotic Device with Compact Joint Design and Related Systems and Methods"), U.S. patent application Ser. No. 16/538,902 (filed on Aug. 13, 2019 and entitled "Robotic Device with Compact Joint Design and Related Systems and Methods"), U.S. patent application Ser. No. 15/227,813 (filed on Aug. 3, 2016 and entitled Robotic Surgical Devices, System and Related Methods") U.S. patent application Ser. No. 15/599,231 (filed on May 18, 2017 and entitled "Robotic Surgical Devices, Systems, and Related Methods"), U.S. patent application Ser. No. 15/687,113 (filed on Aug. 25, 2017 and entitled "Quick-Release End Effector Tool Interface"), U.S. patent application Ser. No. 15/691,087 (filed on Aug. 30, 2017 and entitled "Robotic Device with Compact Joint Design and an Additional Degree of Freedom and Related Systems and Methods"), U.S. patent application Ser. No. 15/821,169 (filed on Nov. 22, 2017 and entitled "Gross Positioning Device and Related Systems and Methods"), U.S. patent application Ser. No. 15/826,166 (filed on Nov. 29, 2017 and entitled "User controller with user presence detection and related systems and methods"), U.S. patent application Ser. No. 15/842,230 (filed on Dec. 14, 2017 and entitled "Releasable Attachment Device for Coupling to Medical Devices and Related Systems and Methods"), U.S. patent application Ser. No. 16/144,807 (filed on Sep. 27, 2018 and entitled "Robotic Surgical Devices with Tracking Camera Technology and Related Systems and Methods"), U.S. patent application Ser. No. 16/241,263 (filed on Jan. 7, 2019 and entitled "Single-Manipulator Robotic Device With Compact Joint Design and Related Systems and Methods"), U.S. Pat. No. 7,492,116 (filed on Oct. 31, 2007 and entitled "Robot for Surgical Applications"), U.S. Pat. No. 7,772,796 (filed on Apr. 3, 2007 and entitled "Robot for Surgical Applications"), and U.S. Pat. No. 8,179,073 (issued on May 15, 2011, and entitled "Robotic Devices with Agent Delivery Components and Related Methods"), all of which are hereby incorporated herein by reference in their entireties.

Certain device and system implementations disclosed in the applications listed above can be positioned within a body cavity of a patient, or a portion of the device can be placed within the body cavity, in combination with a support component similar to those disclosed herein. An "in vivo device" as used herein means any device that can be positioned, operated, or controlled at least in part by a user while being positioned within a body cavity of a patient, including any device that is coupled to a support component such as a rod or other such component that is disposed through an opening or orifice of the body cavity, also including any device positioned substantially against or adjacent to a wall of a body cavity of a patient, further including any such device that is internally actuated (having no external source of motive force), and additionally including any device that may be used laparoscopically or endoscopically during a surgical procedure. As used herein, the terms "robot," and "robotic device" shall refer to any device that can perform a task either automatically or in response to a command.

Certain embodiments provide for insertion of the present invention into the cavity while maintaining sufficient insufflation of the cavity. Further embodiments minimize the physical contact of the surgeon or surgical users with the present invention during the insertion process. Other implementations enhance the safety of the insertion process for the patient and the present invention. For example, some embodiments provide visualization of the present invention as it is being inserted into the patient's cavity to ensure that no damaging contact occurs between the system/device and the patient. In addition, certain embodiments allow for minimization of the incision size/length. Other implementations include devices that can be inserted into the body via an incision or a natural orifice. Further implementations reduce the complexity of the access/insertion procedure and/or the steps required for the procedure. Other embodiments relate to devices that have minimal profiles, minimal size, or are generally minimal in function and appearance to enhance ease of handling and use.

As in manual laparoscopic procedures, a known insufflation system can be used to pump sterile carbon dioxide (or other gas) into the patient's abdominal cavity. This lifts the abdominal wall from the organs and creates space for the robot. In certain implementations, the system has no direct interface with the insufflation system. Alternatively, the system can have a direct interface to the insufflation system.

In certain implementations in which the device is inserted through an insertion port, the insertion port is a known, commercially-available flexible membrane placed transabdominally to seal and protect the abdominal incision. This off-the-shelf component is the same device or substantially the same device that is used in substantially the same way for Hand-Assisted Laparoscopic Surgery (HALS). The only difference is that the arms of the robotic device according to the various embodiments herein are inserted into the abdominal cavity through the insertion port rather than the surgeon's hand. The robotic device body seals against the insertion port when it is positioned therethrough, thereby maintaining insufflation pressure. The port is single-use and disposable. Alternatively, any known port can be used. In further alternatives, the device can be inserted through an incision without a port or through a natural orifice.

Certain implementations disclosed herein relate to "combination" or "modular" medical devices that can be assembled in a variety of configurations. For purposes of this application, both "combination device" and "modular device" shall mean any medical device having modular or interchangeable components that can be arranged in a variety of different configurations.

Certain embodiments disclosed or contemplated herein can be used for colon resection, a surgical procedure performed to treat patients with lower gastrointestinal diseases such as diverticulitis, Crohn's disease, inflammatory bowel disease and colon cancer. Approximately two-thirds of known colon resection procedures are performed via a completely open surgical procedure involving an 8- to 12-inch incision and up to six weeks of recovery time. Because of the complicated nature of the procedure, existing robot-assisted surgical devices are rarely used for colon resection surgeries, and manual laparoscopic approaches are only used in one-third of cases. In contrast, the various implementations disclosed herein can be used in a minimally invasive approach to a variety of procedures that are typically performed 'open' by known technologies, with the potential to improve clinical outcomes and health care costs. Further, the various implementations disclosed herein can be used for any laparoscopic surgical procedure in place of the known mainframe-like laparoscopic surgical robots that reach into the body from outside the patient. That is, the less-invasive robotic systems, methods, and devices disclosed herein feature small, self-contained surgical devices that are inserted in their entireties through a single incision in the patient's abdomen. Designed to utilize existing tools and techniques familiar to surgeons, the devices disclosed herein will not require a dedicated operating room or specialized infrastructure, and, because of their much smaller size, are expected to be significantly less expensive than existing robotic alternatives for laparoscopic surgery. Due to these technological advances, the various embodiments herein could enable a minimally invasive approach to procedures performed in open surgery today.

FIG. 1 depicts one embodiment of a robotic surgical system 10 having several components that will be described in additional detail below. The components of the various system implementations disclosed or contemplated herein can include an external control console 16 and a robotic device 12 having a removable camera 14 as will also be described in additional detail below. In accordance with the implementation of FIG. 1, the robotic device 12 is shown mounted to the operating table 18 via a known, commercially available support arm 20. The system 10 can be, in certain implementations, operated by the surgeon 22 at the console 16 and one surgical assistant 24 positioned at the operating table 18. Alternatively, one surgeon 22 can operate the entire system 10. In a further alternative, three or more people can be involved in the operation of the system 10. It is further understood that the surgeon (or user) 22 can be located at a remote location in relation to the operating table 18 such that the surgeon 22 can be in a different city or country or on a different continent from the patient on the operating table 18.

In this specific implementation, the robotic device 12 with the camera 14 are both connected to the surgeon console 16 via cables: a device cable 24A and a camera cable 24B that will be described in additional detail below. Alternatively, any connection configuration can be used. In certain implementations, the system can also interact with other devices during use such as a electrosurgical generator, an insertion port, and auxiliary monitors.

Figure 2:
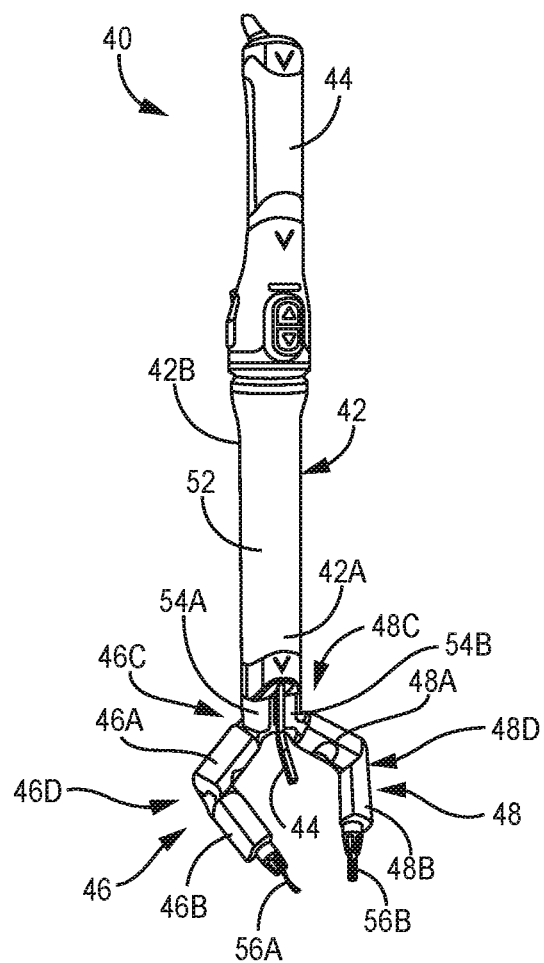
FIG. 2 is perspective view of a robotic device, according to one embodiment.

FIG. 2 depicts one exemplary implementation of a robotic device 40 that can be incorporated into the exemplary system 10 discussed above or any other system disclosed or contemplated herein. The device 40 has a body (or "torso") 42 having a distal end 42A and proximal end 42B, with the imaging device (or "camera") 44 disposed therethrough, as mentioned above and as will be described in additional detail below. Briefly, the robotic device 40 has two robotic arms 46, 48 operably coupled thereto and the camera 44 is removably positionable through the body 42 and disposed between the two arms 46, 48. That is, device 40 has a first (or "right") arm 46 and a second (or "left) arm 48, both of which are operably coupled to the device 40 as discussed in additional detail below. In this embodiment, the body 42 of the device 40 as shown has an enclosure (also referred to as a "cover" or "casing") 52 such that the internal components and lumens of the body 42 are disposed within the enclosure 52. The device body 42 has two rotatable cylindrical bodies (also referred to as "shoulders" or "turrets") 54A, 54B: a first (or "right") shoulder 54A and a second (or "left") shoulder 54B. Each arm 46, 48 in this implementation also has an upper arm (also referred to herein as an "inner arm," "inner arm assembly," "inner link," "inner link assembly," "upper arm assembly," "first link," or "first link assembly") 46A, 48A, and a forearm (also referred to herein as an "outer arm," "outer arm assembly," "outer link," "outer link assembly," "forearm assembly," "second link," or "second link assembly") 46B, 48B. The right upper arm 46A is operably coupled to the right shoulder 54A of the body 42 at the right shoulder joint 46C and the left upper arm 48A is operably coupled to the left shoulder 54B of the body 42 at the left shoulder joint 48C. Further, for each arm 46, 48, the forearm 46B, 48B is rotatably coupled to the upper arm 46A, 48A at the elbow joint 46D, 48D. In various embodiments, the forearms 46B, 48B are configured to receive various removeable, interchangeable end effectors 56A, 56B.

The end effectors 56A, 56B on the distal end of the arms 46, 48 can be various tools 56A, 56B (scissors, graspers, needle drivers and the like), as will be described in additional detail below. In certain implementations, the tools 56A, 56B are designed to be removable, including in some instances by a small twist of the tool knob that couples the end effector 56A, 56B to the arm 46, 48. In certain implementations, at least two single-use, interchangeable, disposable surgical end effectors can be used with any of the robotic device embodiments herein (including device 40). Such end effectors can include, but are not limited to, a fenestrated grasper capable of bi-polar cautery, scissors that deliver mono-polar cautery, a hook that delivers mono-polar cautery, and a left/right needle driver set. The tools can be selected for the specific surgical task. Certain forearm and end effector configurations that allow for the removability and interchangeability of the end effectors are disclosed in detail in U.S. application Ser. No. 14/853,477, which is incorporated by reference above. Further, it is understood that any known forearm and end effector combinations can be used in any of the robotic device embodiments disclosed or contemplated herein.

In various implementations, the body 40 and each of the links of the arms 46, 48 can contain a variety of actuators or motors. In certain implementations, the body 40 has no motors disposed therein, while there is at least one motor in each of the arms 46, 48. In one embodiment, any of the motors discussed and depicted herein can be brush or brushless motors. Further, the motors can be, for example, 6 mm, 8 mm, or 10 mm diameter motors. Alternatively, any known size that can be integrated into a medical device can be used. In a further alternative, the actuators can be any known actuators used in medical devices to actuate movement or action of a component. Examples of motors that could be used for the motors described herein include the EC 10 BLDC+GP10A Planetary Gearhead, EC 8 BLDC+GP8A Planetary Gearhead, or EC 6 BLDC+GP6A Planetary Gearhead, all of which are commercially available from Maxon Motors, located in Fall River, MA There are many ways to actuate these motions, such as with DC motors, AC motors, permanent magnet DC motors, brushless motors, pneumatics, cables to remote motors, hydraulics, and the like. As such, the actuation source can be at least one motor, hydraulic pressure source, pneumatic pressure source, or any other actuation source disposed remotely from or proximally to the device 40 such that an appropriate coupling or transmission mechanism (such as at least one cable, at least one hydraulic transmission hose, at least one pneumatic transmission hose, or any other transmission mechanism) is disposed through the body 42.

In one embodiment, the various joints discussed above in accordance with any of the embodiments disclosed or contemplated herein can be driven by electrical motors disposed within the device and, in some implementations, near each joint. Other embodiments include the incorporation of pneumatic or hydraulic actuators in any of the device implementations herein. In additional alternative embodiments, the driving actuators are disposed outside the device and/or body cavity and power transmission mechanisms are provided to transmit the energy from the external source to the various joints of any device herein. Such a transmission mechanism could, for example, take the form of gears, drive shafts, cables, pulleys, or other known mechanisms, or any combination thereof.

Figure 3A:
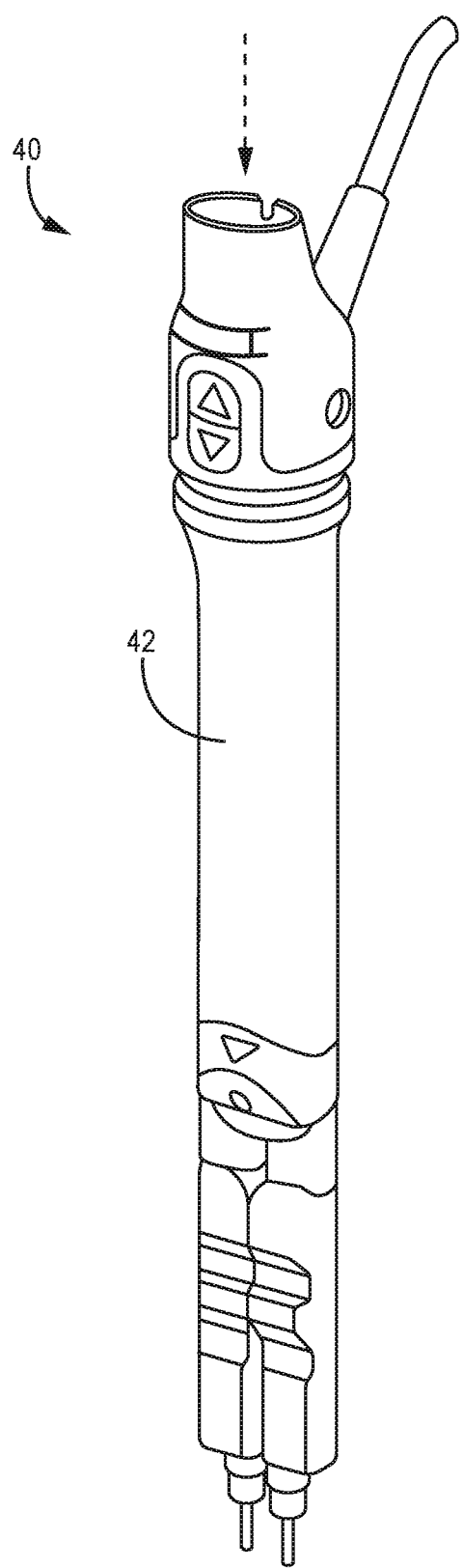
FIG. 3A is another perspective view of the robotic device of FIG. 2, according to one embodiment.
Figure 3B:
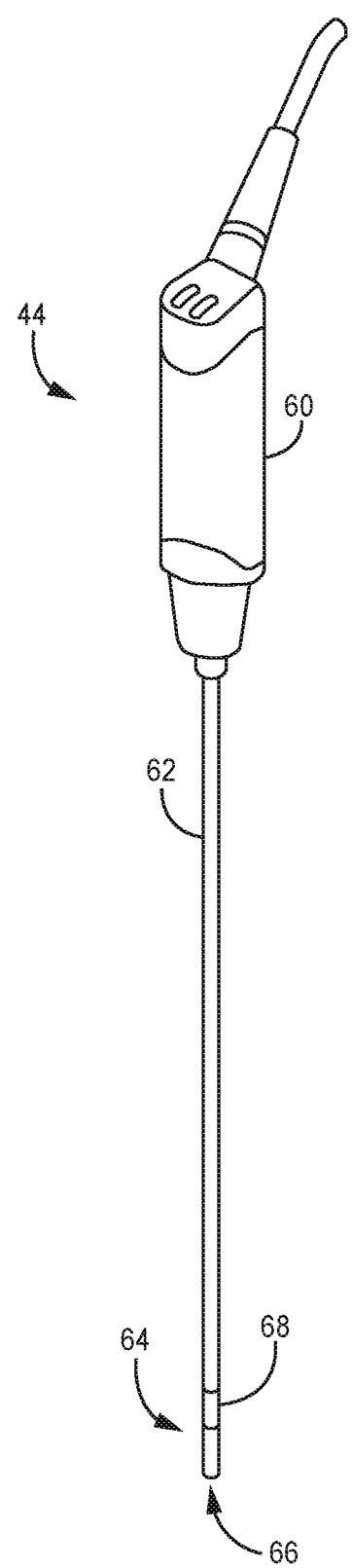
FIG. 3B is a perspective view of camera that is insertable into the robotic device of FIG. 3A, according to one embodiment.

FIGS. 3A and 3B depict one embodiment of the robotic device 40 with the camera assembly 44 removed, according to one implementation. That is, FIG. 3A depicts the device 40 without the camera positioned through the body 42, and FIG. 3B depicts one embodiment of the camera 44. In certain implementations, and as best shown in FIG. 3B, the camera 44 has a handle (or "camera body") 60 with an elongate shaft 62 coupled thereto such that the shaft 62 extends distally from the distal end of the handle 60. In addition, the camera 44 has a steerable tip 64 coupled to the distal end of the shaft 62 via a flexible section 68 such that the steerability allows the user to adjust the viewing direction, as will be discussed in further detail below. Further, the tip 64 also includes a camera imager 66 at the distal end of the tip 64 that is configured to capture the desired images. Further, the tip 64 in certain implementations has an illumination light (not shown) disposed thereon, such that the light can illuminate the objects in the field of view. In one specific implementation, the camera 44 provides 1080p 60 Hz. digital video. Alternatively, the camera 44 can provide any known video quality.

Figure 3C:
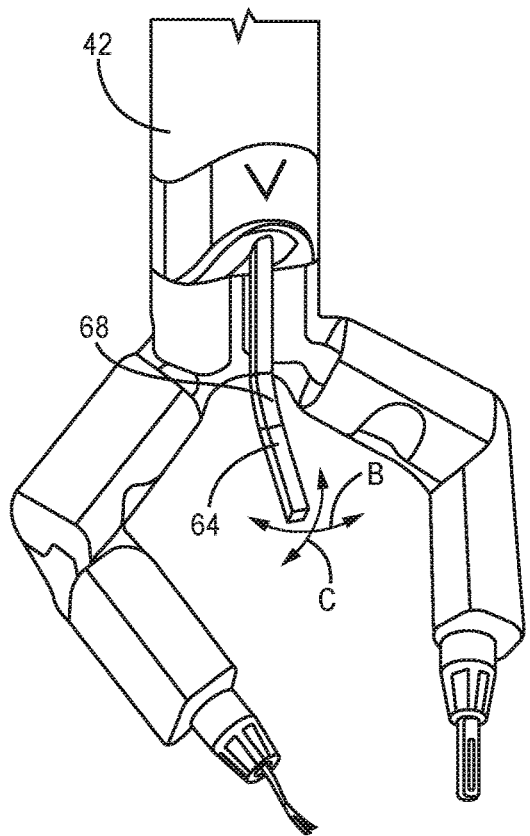
FIG. 3C is an expanded perspective view of the distal end and robotic arms of the robotic device of FIG. 2, according to one embodiment.

As best shown in FIGS. 3A and 3C, the camera assembly 44 can be inserted into the body 42 of the robotic device 40 by positioning the distal end of the shaft 62 through a lumen (not shown) defined through the body 42 of the robotic device 40 as shown by the arrow A in FIG. 3A. As will be described in further detail below, certain implementations of the device 40 include a removable nest (or "dock") (not shown) disposed near the proximal end of the body 42 that includes a seal (not shown) that operates to ensure that the patient's cavity remains insufflated. When the shaft 62 is inserted through the lumen of the body 42 as desired, according to certain embodiments as best shown in FIGS. 2 and 3C, the distal end of the shaft 62, including the flexible section 68 and the steerable tip 64 (containing the imager 66) extends out of an opening at the distal end of the body 42 such that the tip 64 is positioned between the two arms 46, 48 in the surgical environment as shown. Thus, the imager 66 is positioned to capture the view between the two arms 46, 48 and the steerable tip 64 can be actuated to provide views of the surgical tools and surgical target. That is, the tip 64 can be moved such that the surgical tools and/or surgical target are captured within the field of view of the imager 66. It is understood that this camera 44 embodiment and any other such camera embodiment disclosed or contemplated herein can be used with any similar robotic device having a camera lumen defined therethrough.

In various implementations, as best shown in FIG. 3C, the steerable tip 64 and therefore also the camera imager 66 can be steered or otherwise moved in two independent directions in relation to the shaft 62 at a flexible section 68 disposed between the shaft 62 and the steerable tip 64 to change the direction of view. That is, FIG. 3C shows that the steerable tip 64 can be robotically articulated in the yaw direction (left and right in relation to the device 40) as represented by arrow B or pitch direction (up and down in relation to the device 40) as represented by arrow C. In various implementations, the camera 44 can be controlled via a console (such as console 16 discussed above, for example) or via control buttons (not shown) as will be discussed in additional detail below. In one embodiment, the features and operation (including articulation) of the steerable tip are substantially similar to the steerable tip as described in U.S. application Ser. Nos. 14/334,383 and 15/227,813, both of which are incorporated by reference above. Alternatively, any known robotic articulation mechanism for cameras or similar apparatuses can be incorporated into any camera embodiment utilized in any device or system disclosed or contemplated herein.

In various implementations, the camera 44 can be re-sterilized for multiple uses. In one specific embodiment, the camera 44 can be reused up to one hundred times or more. Alternatively, it is understood that any known endoscopic camera that can fit through a device body according to any implementation herein can be utilized.

Figure 4A:
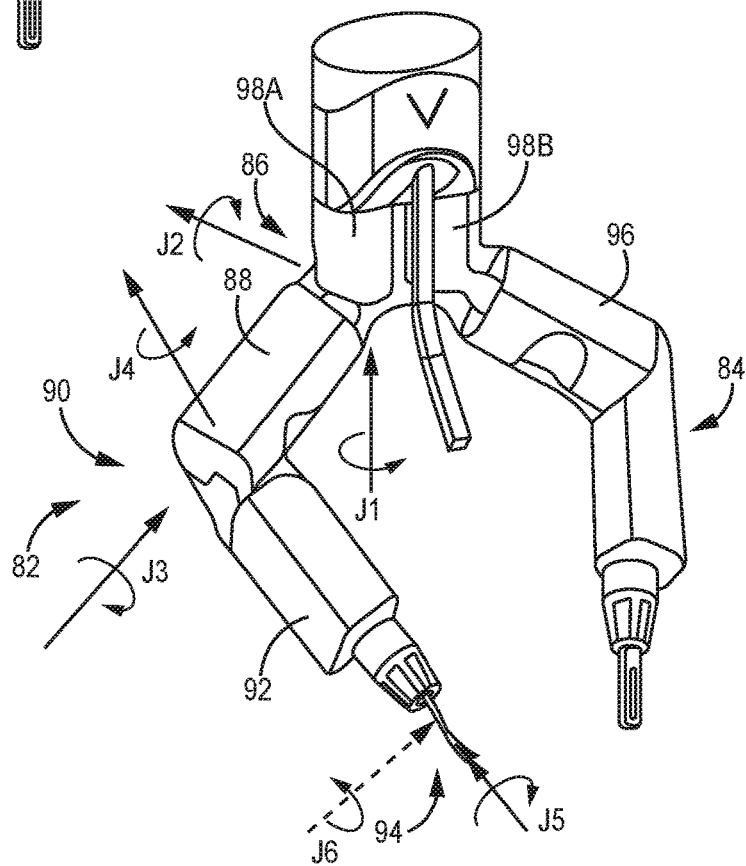
FIG. 4A is an expanded perspective view of the distal end and robotic arms of another robotic device, according to another embodiment.
Figure 4B:
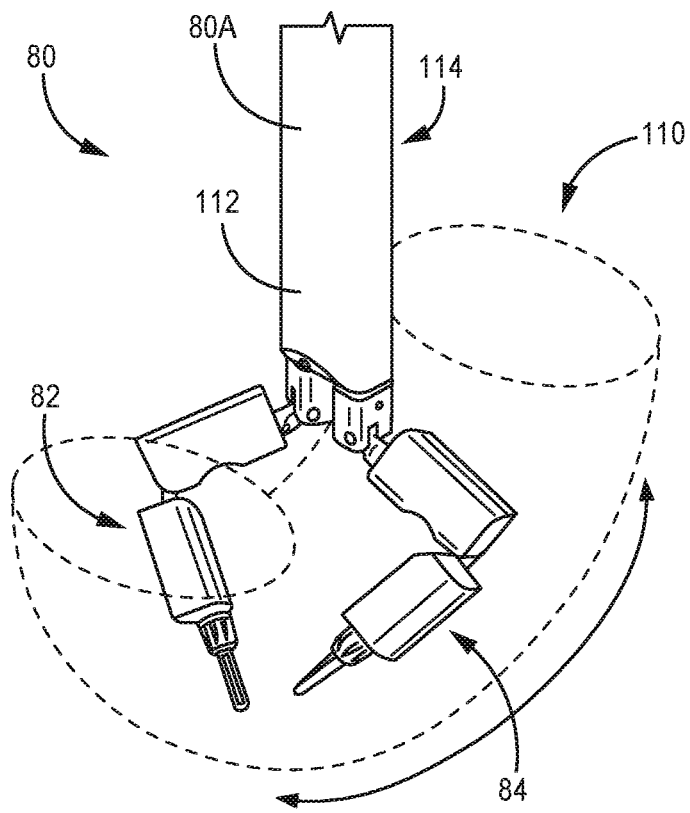
FIG. 4B is another expanded perspective view of the distal end and robotic arms of the robotic device of FIG. 4A, according to one embodiment.

Focusing now on the robotic arms 82, 84 of a robotic device 80 according to one embodiment as shown in FIGS. 4A-4B, each robot arm 82, 84 in this implementation has six degrees of freedom, including the open/close function of the tool, as best shown in FIG. 4A. For purposes of this discussion, the various degrees of freedom will be discussed in the context of the right arm 82 as shown in FIG. 4A, but it is understood that both arms have the same degrees of freedom. The right shoulder joint 86 is approximately a spherical joint similar to a human shoulder. The upper arm 88 can yaw (J1), pitch (J2), and roll about the shoulder joint 86 (J3). These first three axes of rotation roughly intersect at the shoulder joint 86. The robot elbow 90 (J4) allows rotation of the forearm 92 with respect to the upper arm 88. Finally, the end effector 94 can roll (J5) about the long axis of the tool 94 and some tools that can be replaceably attached to the forearm 92 have an open/close actuation function. On the other hand, it is understood that a hook cautery tool, for example, does not open/close.

The robotic arms 82, 84 in this implementation have significant dexterity. As shown in FIG. 4B, the six degrees of freedom described above allow the arms 82, 84 to reach into the confined spaces of the abdominal cavity. FIG. 4B schematically depicts the entire workspace 110 of the arms 82, 84 of the robotic device 80, according to certain implementations. In these implementations, "workspace" 110 means the space 110 around the robotic device 80 in which either arm 82, 84 (and/or end effector thereof) can move, access, and perform its function within that space 110. According to one embodiment, the arms 82, 84 herein are substantially the same as the arms, the degrees of freedom, and the overall workspace and the individual workspaces of each arm as disclosed in U.S. Published Application 2019/0090965, which is hereby incorporated herein by reference in its entirety.

FIG. 4B depicts a perspective view of the device 80 and further schematically shows the collective workspace 110 of the first and second arms 82, 84. Note that the each arm 82, 84 has a range of motion and corresponding workspace that extends from the front 112 of the device 80 to the back 114 of the device 80. Thus, the first arm 82 moves equally to the front 112 and the back 114, through about 180° of space relative to the axis of the device body 80A for each arm 14, 16. This overall workspace 110, which constitutes an intersecting or collective workspace 110 based on the separate workspaces of the two arms 82, 84, allows the robotic device 80 to work to the front 112 and back 114 equally well without having to reposition the body 80A. Thus, the workspace 110 represents a region that is reachable by both the left and right arms 112, 114 and is defined as the bi-manual robot workspace 110. The surgeon will have full robot dexterity when working in this bi-manual region 110.

The bi-manual workspace 110 is approximated by an ellipse that is rotated 180 degrees about the shoulder pitch joint (J2 in FIG. 4A) and is shown in FIG. 4B. For one specific design implementation, the ellipse is approximately 4.5″ (11.5 cm) on the long axis and 3.25″ (8.25 cm) on the minor axis. The bi-manual workspace 110 extends from in front of the robotic device 80 to below the device 80 and is also behind the back of the device 80. This dexterity of the robotic arms 82, 84 allows the surgeon to operate the arms 82, 84 to work equally well anywhere inside this bi-manual workspace 110.

As can be seen in FIG. 4A, the arms 82, 84 in this exemplary implementation have a molded silicon protective sleeve 96 that is disposed over the arms 82, 84 and shoulder turrets 98A, 98B. In one embodiment, the sleeve 96 is fluidically sealed such that it protects the arms 82, 84 and the robotic device 80 from fluid ingress and also helps to simplify post-surgery cleaning and sterilization. The fluidically sealed sleeve 96 is substantially similar to any of the sleeve embodiments disclosed or contemplated in U.S. applications Ser. Nos. 14/334,383, 15/227,813, and 16/144,807, all of which are incorporated by reference above.

Additional features and components of the robotic device include those disclosed in U.S. applications Ser. Nos. 14/334,383, 15/227,813, and 16/144,807, all of which are incorporated by reference above, along with all of the other patents and applications incorporated by reference above. It is understood that any robotic device embodiment disclosed or contemplated herein (including, for example, the robotic devices 12, 40, 80 discussed above), can be incorporated into not only the system embodiments disclosed herein, but any other known robotic surgical system. It is further understood that, according to certain implementations, any robotic device disclosed or contemplated herein can be configured such that it can be cleaned and sterilized for multiple uses. In some embodiments, the device can be reused up to ten times or more.

Figure 5A:
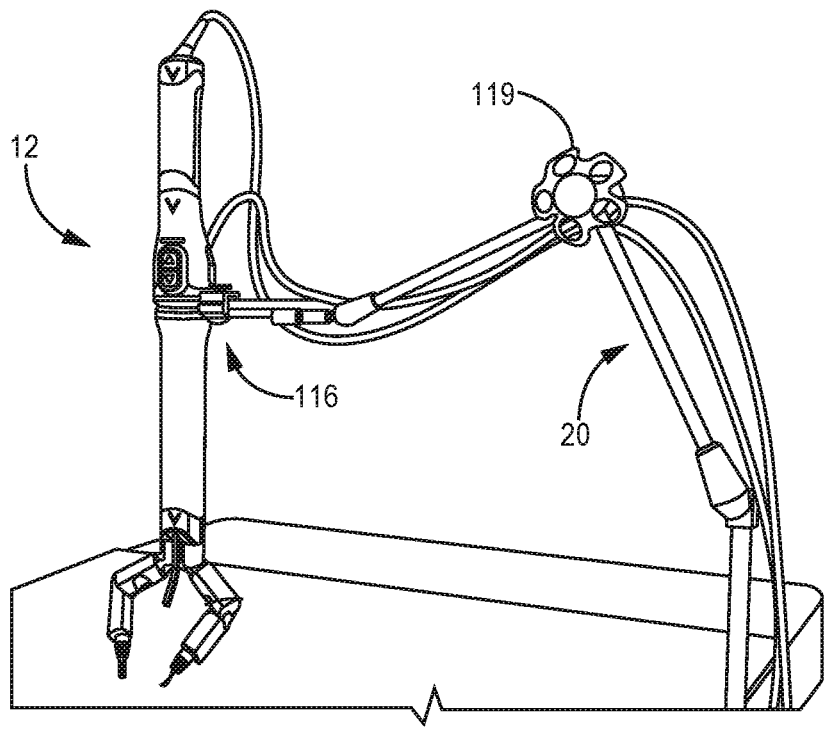
FIG. 5A is a perspective view of a robotic device attached to a support arm coupled to an operating table, according to one embodiment.
Figure 5B:
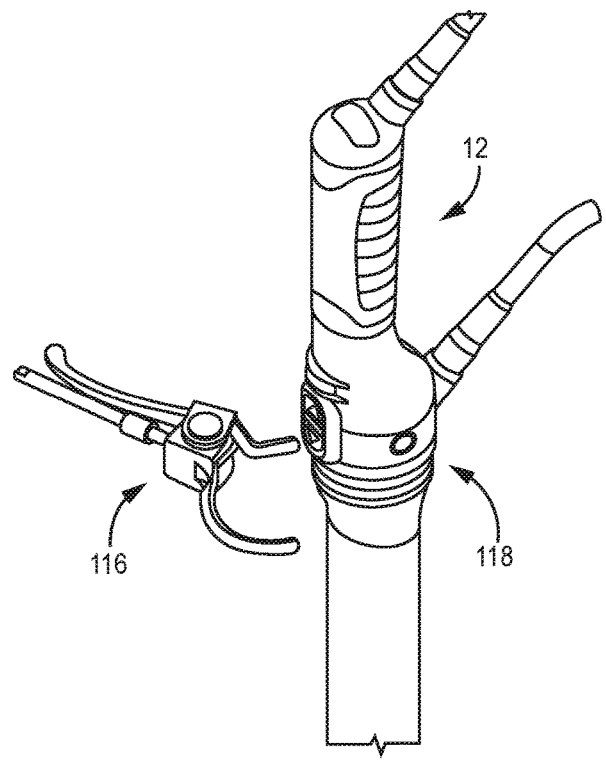
FIG. 5B is an expanded perspective view of the device clamp and robotic device of FIG. 5A, according to one embodiment.

As shown in FIGS. 5A and 5B (and as discussed above with respect to FIG. 1), the device 12 is attached to the operating table 18 via support arm 20. More specifically, the support arm 20 is coupled at one end to the operating table 18 as shown. Further, the support arm 20 has a robotic device body clamp 116 at the other end of the arm 20 such that the clamp 116 can be coupled to a clamp interface ring 118 defined in an outer surface of the enclosure 52 of the device body 42, as best shown in FIG. 5B. Certain embodiments of the clamp 116 are disclosed in additional detail in U.S. Published Application 2017/0035526, which is hereby incorporated herein by reference in its entirety. In addition, the support arm 20 has an adjustment knob 119 that allows for the arm 20 to be adjusted such that the attached device 12 can be repositioned to numerous different position options as needed. As such, the device 12 is adjustably attached to the table 18 via the arm 20. Alternatively, any known support arm can be used to support the various robotic device embodiments herein. Thus, in addition to the positioning of the device 12 and arms 46, 48 as discussed above, in various implementations, the robotic device 12 can reach any area of the surgical cavity because it can be easily repositioned during the procedure via "gross positioning." That is, the device 12 can be quickly, in a matter of seconds, moved by manually adjusting the external support arm 20 and robot clamp 116. The combination of gross positioning of the robotic device 12 and the dexterity of the robot arms 46, 48 as described above allow the surgeon to place the device 12 so it can work anywhere in the target cavity of the patient with, in certain embodiments, the arms 46, 48 well triangulated for the given procedure, as discussed elsewhere herein.

The various camera embodiments herein (including cameras 14 and 44, for example) can, in certain implementations, be coordinated with the device to which it is coupled to create coordinated triangulation between the camera and the arms and end effectors for any configuration, positioning, and use of the device. Further, the steerable tip of any such camera can be robotically articulated so as to reposition the field of view, either automatically or via control by the surgeon using the system console. That is, the camera articulates to ensure the surgeon can view all possible locations of the robotic arms as well as the desired areas of the surgical theater. Further, as the robotic arms move—the steerable camera tip can be coordinated with the arms to move using active joints in coordination with the arm movements to view the entire robot workspace. In certain implementations, the joints of the camera are actively controlled using motors and sensors and a processor (and, in some implementations, a control algorithm contained therein). In these implementations, the processor allows for automated and/or semi-automated positioning and re-positioning of the camera 12 about the pitch ($\alpha$) and/or yaw ($\beta$) rotations relative to the robotic device. It is understood that the various embodiments of systems and devices having such a coordination between the camera and the device (and arms) and the resulting features thereof are disclosed in detail in U.S. Published Application 2019/0090965, which is incorporated by reference above.

Figure 6:
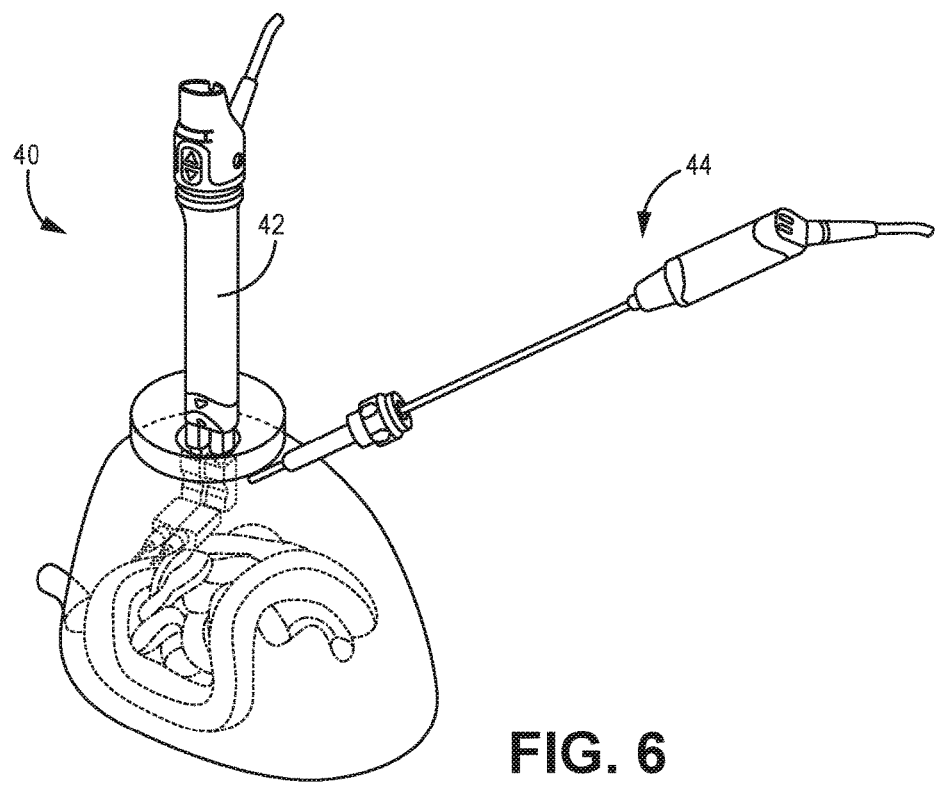
FIG. 6 is a schematic perspective view of a robotic device and a camera component that is not positioned in the device and is instead being operated via a separate port in a patient, according to one embodiment.

Alternatively, in certain implementations as shown in FIG. 6, the camera 44 can be removed from the robotic device 40 and positioned through another, known laparoscopic port 120 typically used with a standard manual laparoscope. As such, in this embodiment, the device 40 is disposed through a main port (also known as an "insertion port") 122 and the camera 44 is positioned through the known laparoscopic port 120 as shown. It is understood that this arrangement may be useful to visualize the robotic device 40 to ensure safe insertion and extraction via the main port 122. According to various embodiments, the camera 44 can also be removed from the robotic device 40 so the optics can be cleaned, the camera 44 can be repaired, or for any other reason in which it is beneficial to remove the camera 44. It is understood that while the device 40 and camera 44 are depicted and discussed herein, any device or camera according to any implementation disclosed or contemplated herein can also be used in a similar arrangement and any such camera can also be removed from the device for any reason as discussed herein.

It is understood that the insertion port 122 also can represent the port 122 through which any robotic device embodiment disclosed or contemplated herein is positioned for any procedure as contemplated herein (including those procedures in which the camera 44 is disposed through the device 40). In one embodiment, the insertion port 122 can be a single use commercially available flexible membrane disposed transabdominally to seal and protect the abdominal incision and allow for positioning the body 42 of the device 40 therethrough. In specific implementations, the insertion port 122 is the same device used in Hand-Assisted Laparoscopic Surgery (HALS), including the exemplary port 122 depicted in FIG. 6, which, according to one embodiment, is a GelPort™ 122. The device body 42 seals against the insertion port 122, thereby establishing a fluidic seal and thus maintaining insufflation pressure. Alternatively, any known insertion port (or incision) that is configured to receive a device similar to that disclosed herein can be used.

Figure 7:
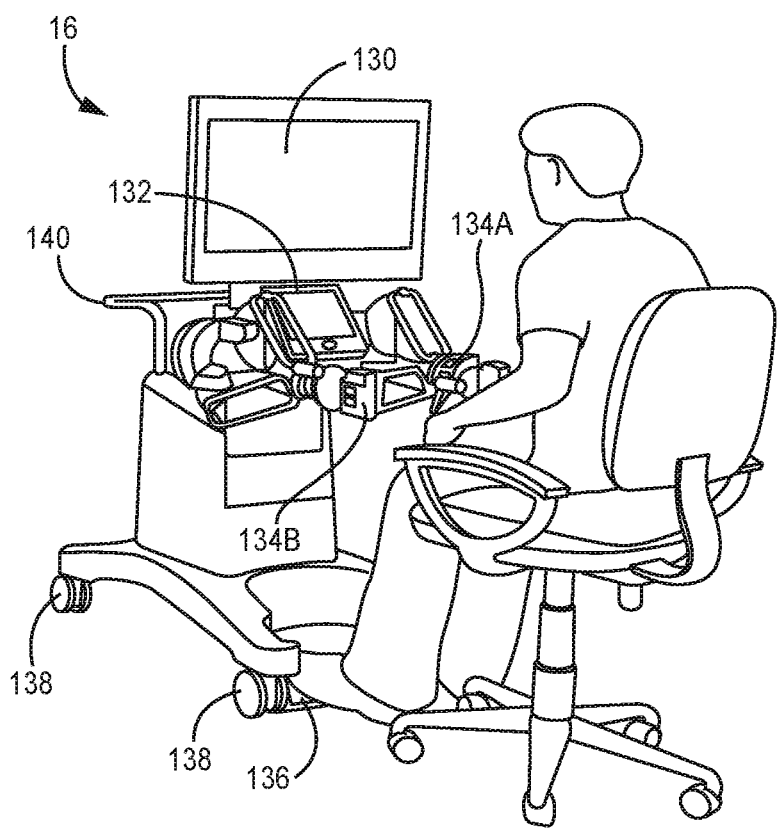
FIG. 7 is an expanded perspective view of the console of the surgical system of FIG. 1, according to one embodiment.

Returning to the overall system embodiments, such as the system 10 depicted in FIG. 1 and discussed above, the robotic device (such as device 12 or device 40) can be piloted, in accordance with certain embodiments, via the surgeon console 16 as shown in FIGS. 1 and 7. This exemplary implementation of the surgeon console 16 contains a main processor (not shown) that performs robot control functions, system monitoring, and any other known processes or functionalities necessary or beneficial for controlling a system according to any embodiment herein. In these implementations, the console 16 also has a real-time display 130 that can display real-time images of the surgical environment using the output of the camera (such as camera 14 or 44). In one embodiment, the display 130 is a high definition display 130. Alternatively, any known display can be used. In addition, the console 16 can also have a touchscreen interface 132 that can be used to control several functions of the console 16 and device 12 (or device 40). In certain implementations, the touch screen 132 can also display various types of information about the state of the robotic device 12 (or 40) or any other component of the system 10. Alternatively, any known console can be used with the various implementations of the system disclosed or contemplated herein.

The console 16 in this implementation also has right and left hand controllers (or "input devices") 134A, 134B that can be used to control various aspects of the device 12, 40 and/or camera 14, 44, including movement thereof. The surgeon can interface with the input devices 134A, 134B using the surgeon's hands such that the input devices 134A, 134B can track the movement of the surgeon's hands. In certain embodiments, each of the input devices 134A, 134B can have a surgeon presence sensor to track whether the surgeon's hands are properly engaged. In one exemplary embodiment, the user presence sensor is any of the embodiments disclosed or contemplated in U.S. patent application Ser. No. 15/826,166, which is incorporated by reference above. In certain implementations, the input devices 134A, 134B can also be configured to provide haptic feedback by pushing on the surgeon's hands to indicate things such as workspace boundaries and collisions between the robot arms, as is described in detail in U.S. patent application Ser. No. 15/227,813 and U.S. Pat. No. 9,888,966, both of which are incorporated by reference above. According to various embodiments, the input devices 134A, 134B can also control open/close functions of the robot's end effectors.

In accordance with some implementations, the surgeon console 16 can also have foot pedals 136 that are configured to be operable by the surgeon's feet to control various robot functions, including, for example, clutching, camera movements, and various electro cautery functions. Alternatively, the pedals 136 can be used to operate any known functions of the robotic device 12, 40 or any other component of the system 10. In a further alternative, any other input devices on the console 16 can be used to control those various functions.

The surgeon console 16 according to certain implementations can be configured such that it can be operated by a surgeon positioned in either a sitting position (similar to Intuitive's da Vinci console) or a standing position (similar to manual laparoscopy). The console 16 in this exemplary embodiment is designed to be easily transported between operating rooms using castors 138 and a transport handle 140. In certain embodiments, the height of the console 16 is adjustable.

Other console and system embodiments that can be incorporated into any system disclosed or contemplated herein are disclosed in U.S. applications Ser. Nos. 14/334,383, 15/227,813, and 16/144,807, all of which are incorporated by reference above, along with any of the other relevant patents and applications incorporated by reference above.

The various components in said applications include companion carts, an interface pod, an electrosurgical generator, and the appropriate cables and connections, for example. Further, it is understood that any other known console or controller can be utilized with any robotic device or system disclosed or contemplated herein.

Figure 8A:
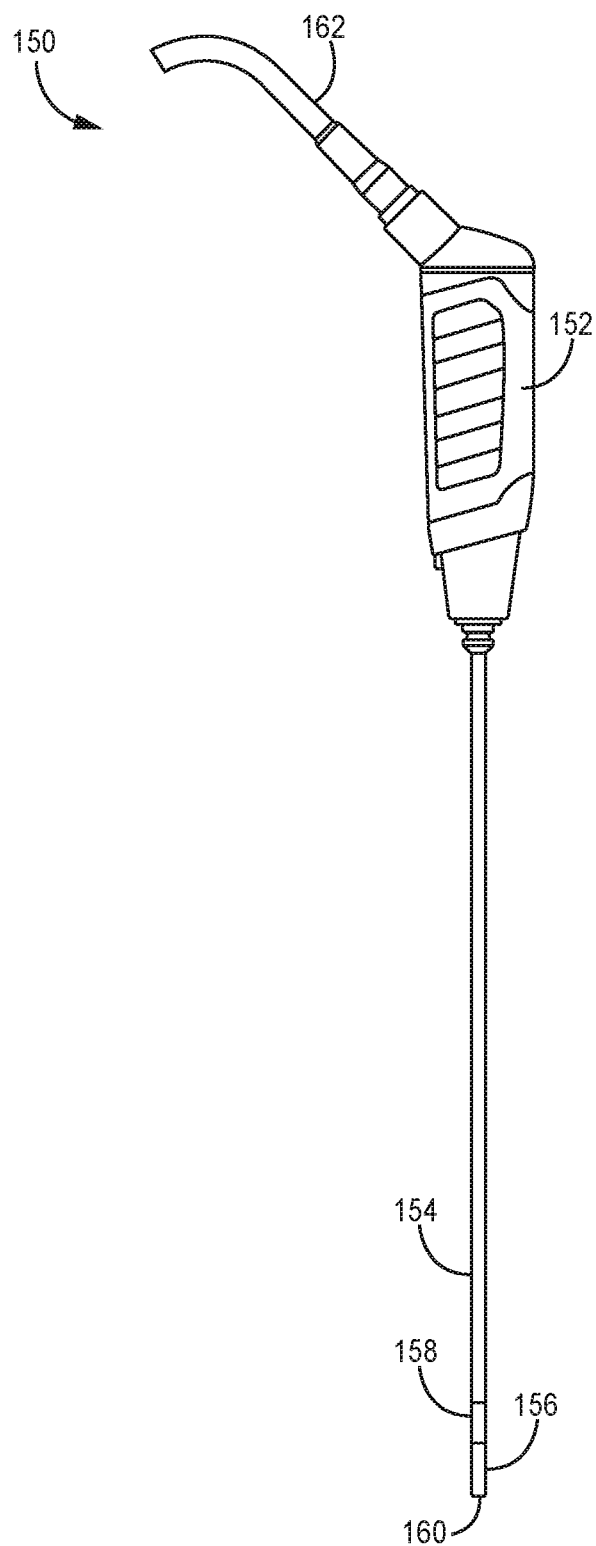
FIG. 8A is an side view of camera assembly, according to one embodiment.
Figure 8B:
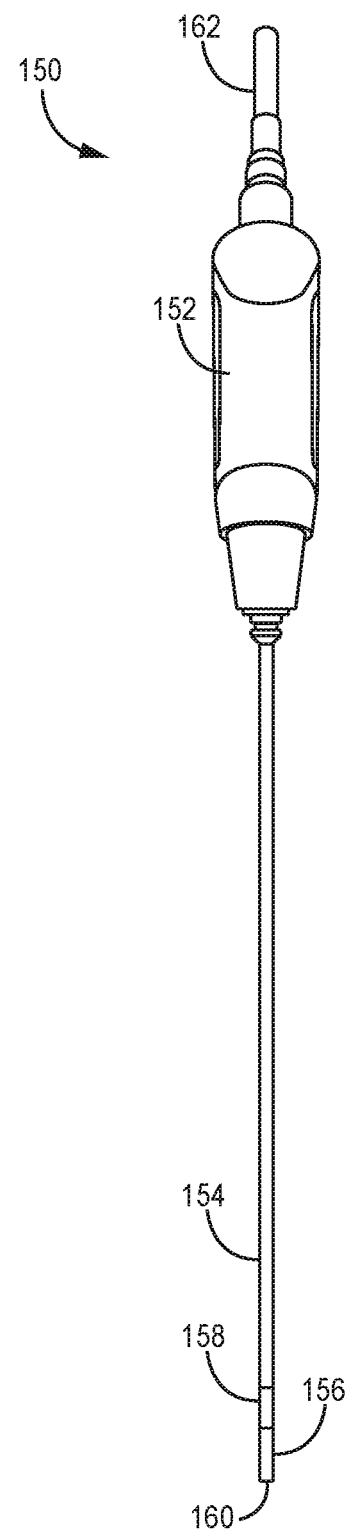
FIG. 8B is a front view of the camera assembly of FIG. 8A, according to one embodiment.

Another camera embodiment is depicted in FIGS. 8A and 8B (with FIG. 8A depicting a side view and FIG. 8B depicting a front view), in which the camera assembly 150 has a handle (or "camera body") 152 with an elongate shaft 154 coupled thereto such that the shaft 154 extends distally from the distal end of the handle 152. In addition, the camera 150 has a steerable tip 156 coupled to the distal end of the shaft 154 via a flexible section 158 that couples the tip 156 to the shaft 154 such that the steerability allows the user to adjust the viewing direction, as will be discussed in further detail below. The tip 156 includes a camera imager (also referred to as an "imaging sensor") 160 at the distal end of the tip 156 that is configured to capture the desired images, along with optics and support electronics (not shown). In this embodiment, the camera 150 also has light fibers (not shown) that are disposed through the shaft 154, flexible section 158, and tip 156 such that the light fibers provide light output at the tip 156 so as to light the surgical target for imaging. In addition, the assembly 150 has a cable 162 that is coupled to the handle 152 and extends therefrom to an external controller (such as the console 16 discussed above or any other controller) such that the cable 162 can provide electrical signals to and from the camera 150, including a video signal and any power and other signals or information necessary to operate the camera 150.

The steerable tip 156 can be robotically articulated in two independent directions, according to one embodiment. More specifically, as discussed above in additional detail with respect to the camera assembly 44 embodiment and depicted in FIG. 3C, the steerable tip 156 can be articulated to move in both the pitch and yaw directions.

Figure 9A:
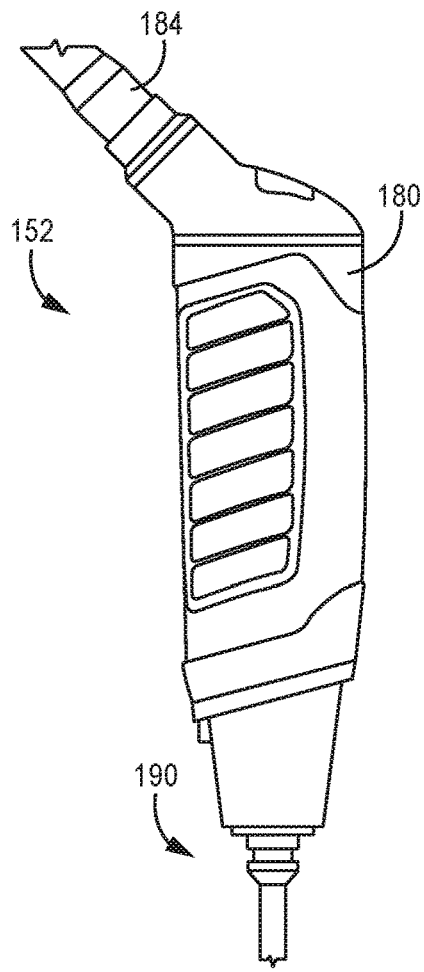
FIG. 9A is an expanded side view of the camera body of the camera assembly of FIG. 8A, according to one embodiment.
Figure 9B:
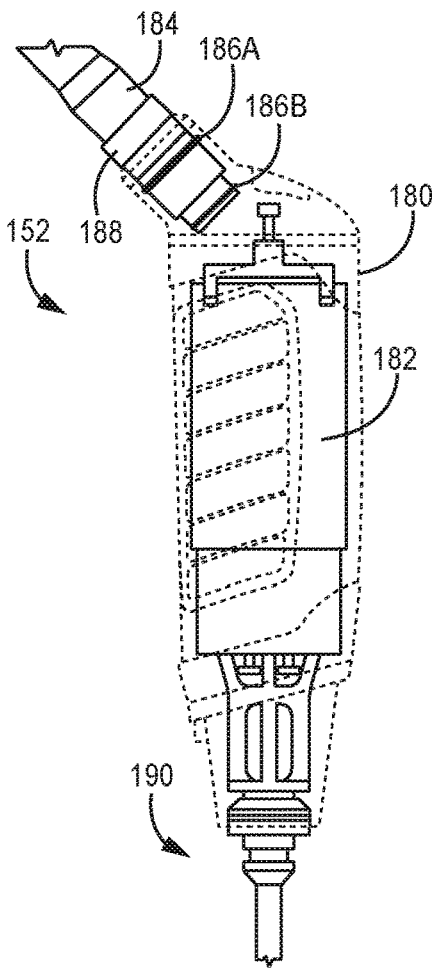
FIG. 9B is an expanded cutaway side view of the camera body of FIG. 9A, according to one embodiment.
Figure 9C:
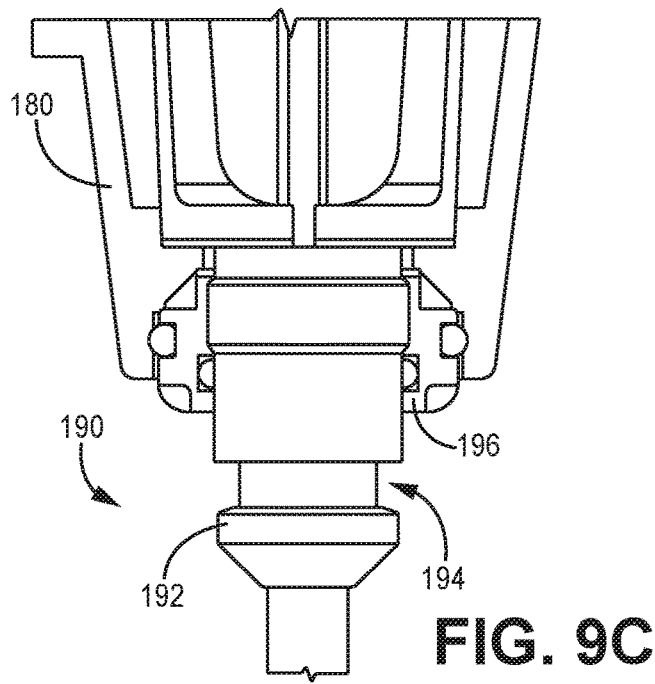
FIG. 9C is an expanded cross-sectional view of the distal end of the camera body of FIG. 9A, according to one embodiment.

FIGS. 9A, 9B, and 9C are expanded views of the camera handle 152 according to one embodiment. In this exemplary implementation, the camera handle 152 has an outer enclosure (also referred to as "exterior housing," "housing," or "enclosure") 180, as best shown in FIG. 9A, with an inner housing 182 disposed within the enclosure 180, as best shown in FIG. 9B. In certain embodiments, the inner housing 182 is an inner heat distribution sink 182 that can function to distribute heat inside the camera handle exterior housing 180. More specifically, the heat distribution sink 182 is a cylinder 182 or structure 182 of any appropriate shape that is disposed within the enclosure 180 and around the internal components of the handle 152. The sink 182 is made of a material that distributes heat across the structure 182 and has a thermal capacity for heat. In one specific embodiment, the material is aluminum. Alternatively, the sink 182 can be made of any known heat sink material. The outer enclosure 180 helps to enclose the heat sink 182 and the internal mechanical and electrical components of the handle 152.

In addition, the handle 152 according to various implementations also has a cable strain relief assembly 184 extending from the proximal end of the handle 152 such that the cable 162 is disposed through the relief assembly 184. In one embodiment, the relief assembly 184 is a tube 184 or other elongate structure 184 through which the cable 162 can be disposed such that the relief assembly 184 has a reinforced structure to reduce the strain applied on the cable 162 when force is applied to the cable 162. It is understood that the cable strain relief assembly 184 can be any known structure for providing strain relief. Alternatively, the assembly 184 can be any known cable strain relief assembly.

The camera handle 152 also has, in this specific implementation, two O-ring seals 186A, 186B disposed around the cable connection 188. The seals 186A, 186B are disposed between the connection 188 and the housing 180, thereby establishing a fluidic seal therebetween and thus helping to prevent fluid ingress. Alternatively, there can be one seal, three seals, or any number of seals disposed around the connection 188. In a further alternative, the seal(s) need not be an O-ring seal, and instead can be any known type of seal.

The distal end of the camera handle 152 has a nose cone 190 extending therefrom, according to one embodiment. As best shown in FIG. 9C, the nose cone 190 is a distal structure 190 that extends distally from the handle 152. The nose cone 190 includes a nose cone tip 192 at the distal end of the nose cone 190 and slot 194 defined in the nose cone proximal to the tip 192. In one embodiment, the nose cone slot 194 is a camera coupling mechanism acceptance slot 194 such that the camera latch 420 discussed in further detail below can be received in the slot 194. As such, the camera latch acceptance slot 194 can work in conjunction with the camera latch 420 to assist with attaching the camera to the elongate body 42 of the elongate device 40 (or any other device embodiment herein) via the nest structure 346 as also discussed in detail below.

In addition, the nose cone 190 has a protrusion (or "collar") 196 that is disposed around the cone 190 and has both an outer O-ring seal 198A and an inner O-ring seal 198B attached to the protrusion 196 as shown. The outer O-ring seal 198A is disposed on an outer circumference of the collar 196 such that the seal 198A is disposed between the collar 196 and the camera body enclosure 180. Further, the inner O-ring seal 198B is disposed on an inner circumference of the collar 196 such that the seal 198B is disposed between the collar 196 and the cone 190. As such, the seals 198A, 198B help to establish a fluidic seal between the nose cone 190 and the camera housing 180, thereby creating a sealed camera handle 152 that helps to protect the internal mechanical and electrical components during use and cleaning.

In use, the camera assembly 150 is typically held by a user (such as a surgical assistant and/or surgeon) via the camera handle/body 152 when the camera 150 is moved around and inserted into or removed from the device body 42 (or any other device body embodiment herein) (or when used independently of any robotic device as discussed above). Further, the nose cone 190 of the handle 152 is sized and shaped to couple with and assist with attachment to the elongate body 42 (or any other device body embodiment herein) as discussed in additional detail below.

In accordance with one embodiment as shown in FIGS. 10A and 10B, the camera body/handle 152 can contain several internal components. FIG. 10A is a side view of the internal components of the handle 152 (the same view as that provided in FIGS. 8A, 9A, and 9B), while FIG. 10B is a front view (the same view as FIG. 8B). As best shown in FIG. 10A, the handle 152 in this implementation has an LED light source 220 with two light transmission fibers 222A, 222B coupled thereto that extend distally from the light source 220 through the interior of the handle 152 and toward and toward through camera shaft 154 to the distal tip of the shaft 154. Thus, the fibers 222A, 222B transmit light from the source 220 along the fibers 222A, 222B to the field of view of the imager 160 as discussed above. As such, the light from the light source 220 ultimately shines on the imaging target. It is understood that the light source 220 can be adjusted via a controller (such as the console 16), including via software in the controller or console 16, in a known fashion to adjust the light intensity produced therefrom. Alternatively, the handle 152 can have two LED light sources, with each separate source coupled to a different one of the two transmission fibers. In a further alternative, one transmission fiber can be used, or three or more fibers can be used. In yet another alternative, any configuration for transmitting light to the steerable tip 156 can be incorporated into any of the camera embodiments disclosed or contemplated herein.

In addition, the camera body 152 also has at least one circuit board 224 disposed therein. In one embodiment, the at least one circuit board 224 can be used to control the camera assembly 150 in any number of known ways. In some non-limiting examples, the at least one circuit board 224 can control the light source 220 or any facet of the lighting, the video signal, the image sensor 160, the actuation mechanisms 226A, 226B, or any sensors present anywhere on or in the camera 150. Alternatively, the camera body 152 can have two or more circuit boards for controlling various components and/or features of the camera 150. Further, the camera body 152 also has an actuator unit (also referred to herein as an "articulation unit") 226 that actuates the steerable tip 156. That is, the actuator unit 226 is operably coupled to the steerable tip 156 such that the actuator unit 226 actuates the tip 156 to move in both directions as described in additional detail herein: pitch and yaw. In this specific embodiment, the actuator unit 226 is actually made up of two actuator mechanisms: a first (or yaw or left/right) actuation mechanism 226A and a second (or pitch or north/south) actuation mechanism 226B. As will be described in additional detail below, each of the two mechanisms is coupled to the steerable tip 156 via cables that can be used to transfer the motive force use to move the steerable tip 156 as described herein. In one embodiment as best shown in FIG. 10B, each of the two mechanisms is coupled to the steerable tip 156 via a pair of cables, with the first mechanism 226A coupled to the tip 156 via cable pair 228 and the second mechanism 226B coupled to the tip 156 via cable pair 230. That is, as best shown in the side view of FIG. 10A, the first pair of cables 228A, 228B is coupled at the proximal ends of the pair 228A, 228B to the first mechanism 226A and further is coupled at the distal ends of the pair 228A, 228B to the steerable tip 156. Similarly, as shown in profile in FIG. 10B, the second pair of cables 230 is coupled at the proximal ends thereof to the second mechanism 226B and at the distal ends of the pair 230 to the steerable tip 156. In one embodiment, the cable pairs 228, 230 are known Bowden cables 228, 230, as will be described in additional detail below.

Figure 10C:
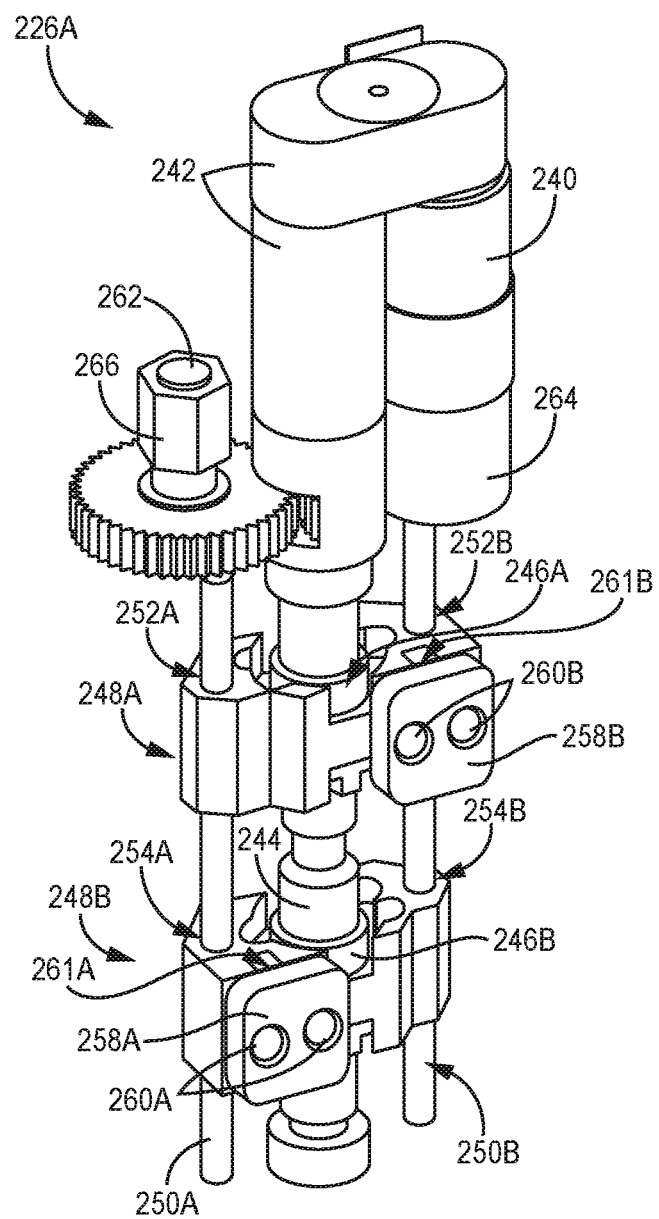
FIG. 10C is a perspective cutaway view of an actuation mechanism for the camera body of FIG. 9A, according to one embodiment.

FIG. 10C depicts one of the two actuation mechanisms, according to one embodiment. That is, the first actuation mechanism 226A is depicted in FIG. 10C, but it is understood that the second actuation mechanism 226B has similar components and operates in a similar fashion, according to one embodiment. The mechanism 226A has a drive motor 240, a gear train 242 rotationally coupled to the drive motor 240, and a double thread lead screw 244 rotationally coupled to the gear train 242. Thus, actuation of the drive motor 240 causes rotation of the gear train 242, which causes rotation of the lead screw 244. Alternatively, the motor 240 can be rotationally coupled to the lead screw 244 via any gear or other rotational coupling combination. According to one implementation, the actuation mechanism 226A can also have two sensors 262, 264 that are used to measure the angular position of the lead screw 244. One sensor 262 has a magnet 262 that is rotatably coupled to the lead screw 244 such that the sensor 262 provides for absolute position measurement. The other sensor 264 in this implementation is a position sensor 264 as shown. It is understood that either of these sensors 262, 264 can be any known sensors for tracking the position of the lead screw 244. In accordance with certain implementations, the actuation mechanism 226A also allows for manually driving the lead screw 244. That is, this embodiment has a manual drive input 266 which, in this exemplary embodiment, is a nut 266 that can be turned using a simple tool such as a wrench or the user's fingers. This manual drive mechanism 266 can be used for unpowered movement during assembly or service of the actuation mechanism 226A.

As best shown in FIGS. 10C and 10D, the double thread lead screw 244 has two sets of threads: a first set of threads 246A and a second set of threads 246B. In one embodiment, the two sets of threads 246A, 246B have opposite threads. That is, one of the two sets of threads 246A, 246B has right-handed threads, while the other set has left-handed threads. As best shown in FIGS. 10C and 10E, the actuation mechanism 226A also has two carriages threadably coupled to the double thread lead screw 244. More specifically, the first carriage 248A is threadably coupled to the first set of threads 246A, while the second carriage 248B is threadably coupled to the second set of threads 246B. Each of the two carriages 248A, 248B are slidably disposed in the actuation mechanism 226A along the rods (also referred to as "linear bearings") 250A, 250B. That is, each of the carriages 248A, 248B have lumens 252A, 252B, 254A, 254B disposed therethrough as shown such that the rods 250A, 250B are disposed therethrough. In other words, the first carriage 248A is slidably disposed on the rods 250A, 250B via lumens 252A, 252B, while the second carriage 248B is slidably disposed on the rods 250A, 250B via lumens 254A, 254B as shown. Thus, given that the sets of threads 246A, 246B have opposite threads, rotation of the lead screw 244 in one direction causes the carriages 248A, 248B to move linearly toward each other (closer together), while rotation of the lead screw 244 in the opposite direction causes the carriages 248A, 248B to move linearly away from each other (farther apart). It is understood that, according to certain embodiments, if the threads of the two sets 246A, 246B have the same pitch, then the carriages 248A, 248B will move in equal and opposite directions.

In addition, each carriage 248A, 248B is coupled to a separate one of the two cables of the cable pair 228, as mentioned above with respect to FIGS. 10A and 10B. More specifically, the first carriage 248A is coupled to the first cable 228A of the pair 228, and the second carriage 248B is coupled to the second cable 228B. In one specific embodiment as best shown in FIG. 10C, each carriage has a coupling structure 258A, 258B that is used to attach the cable 228A, 228B in place. That is, the first carriage 248A has the first coupling structure 258A that can removably couple the cable 228A to the carriage 248A. Similarly, the second carriage 258B has the second coupling structure 258B that can removably couple the cable 228B to the carriage 248B. In this specific implementation, the coupling structures 258A, 258B are clamping structures 258A, 258B in which screws 260A, 260B can be used to loosen or tighten the clamping structures 258A, 258B to removably couple the cables 228A, 228B thereto. Further, each of the coupling structures 258A, 258B also have a half lumen 261A, 261B defined in the side of each carriage 248A, 248B such that the cable 228A, 228B can be disposed within the half lumen 261A, 261B and the clamping structure 258A, 258B can be positioned against the cable 228A, 228B and tightened with the screws 260A, 260B to fix the cables 228A, 228B in place. It is understood that the cables 228A, 228B are coupled at their distal ends to the steerable tip 156, as discussed above. More specifically, one of the two cables 228A, 228B is coupled to the steerable tip 156 such that actuation of that cable 228A, 228B causes the tip 156 to move to the left, while the other of the two cables 228A, 228B is coupled to the tip 156 such that actuation of that cable 228A, 228B causes the tip 156 to move to the right.

Figure 10F:
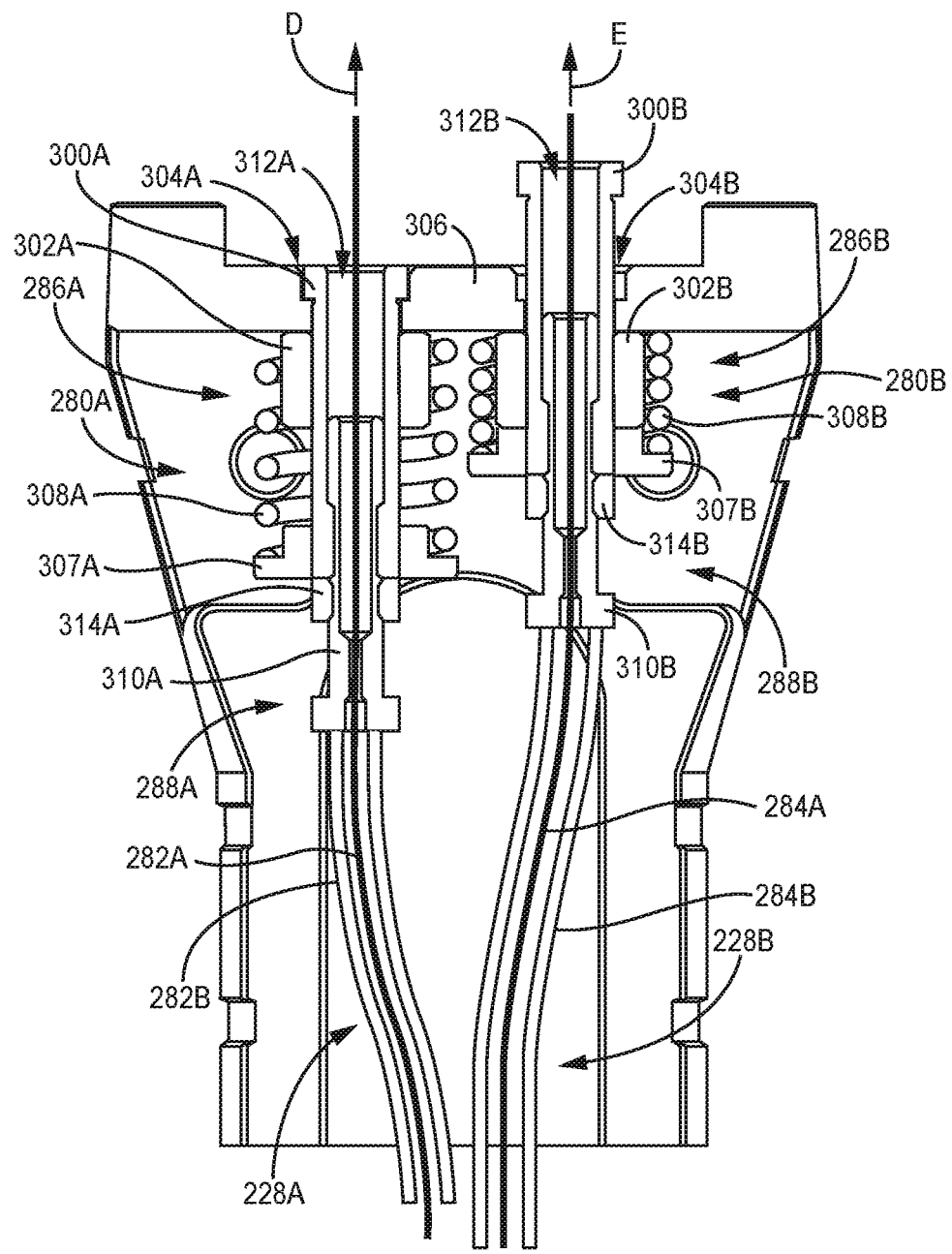
FIG. 10F is a cutaway view of certain components of the camera body of FIG. 9A, according to one embodiment.

FIG. 10F depicts an expanded view of a section of FIG. 10A depicting the internal components of the camera body 152, according to one embodiment. More specifically, FIG. 10F depicts the relationship between the cables 228A, 228B and the connection assemblies 280A, 280B disposed distally of the actuation mechanism 226A. In this exemplary implementation, each of the cables 228A, 228B is a known Bowden cable having an inner cable that is slidably disposed within a cable housing along part of the length of the inner cable. More specifically, the first cable 228A has both an inner cable 282A and a housing 282B. The inner cable 282A extends from the actuation assembly 226A to the steerable tip 156, while the housing 282B extends from the connection assembly 280A to the steerable tip 156. Similarly, the second cable 228B has an inner cable 284A that extends from the actuation assembly 226A to the steerable tip 156 and a housing 284B extending from the connection assembly 280B to the steerable tip 156. Thus, a distal length of the inner cable 282A is slidably disposed within the cable housing 282B, while a proximal length of the inner cable 282A extends out of the housing 282B at the connection assembly 280A and extends toward the actuation assembly 226A as shown at arrow D. Similarly, a distal length of the inner cable 284A is slidably disposed within the cable housing 284B, while a proximal length of the inner cable 284A extends out of the housing 284B at the connection assembly 280B and extends toward the actuation assembly 226A as shown at arrow E. Thus, the inner cables 282A, 284A are actuable by the actuation assembly 226A as discussed above to articulate the steerable tip 156 via linear movement of the inner cables 282A, 284A. In one embodiment, each of the cable housings 282B, 284B is made of a known composite construction with an inner lining (to facilitate movement of the inner cable therein) and is longitudinally incompressible.

Each connection assembly 280A, 280B has both a tension spring assembly 286A, 286B and a tension adjustment mechanism 288A, 288B, both of which will be described in detail below.

According to one embodiment, each tension spring assembly 286A, 286B is operable to absorb force applied to the cable housings 282B, 284B and thereby reduce the strain applied thereto and potentially prevent resulting damage. That is, each tension spring assembly 286A, 286B has a tension spring retainer body 300A, 300B that is slidably disposed through a bushing 302A, 302B and an opening 304A, 304B defined in a body wall 306. Each bushing 302A, 302B is fixedly attached to the body wall 306 such that each spring retainer body 300A, 300B is slidable in relation to the body 152. Each retainer body 300A, 300B has a tension spring 308A, 308B disposed around the body 300A, 300B and positioned between a lip 307A, 307B on the retainer body 300A, 300B and the body wall 306 such that each tension spring 308A, 308B can move between an extended state (as shown in assembly 280A) and a compressed state (as shown in assembly 280B). In addition, each retainer body 300A, 300B has an extendable barrel 310A, 310B extending from a distal end of the retainer body 300A, 300B. Each cable housing 282B, 284B is coupled to the extendable barrel 310A, 310B as shown. It is understood that both the retainer bodies 300A, 300B and the extendable barrels 310A, 310B have lumens 312A, 312B defined therethrough as shown such that the inner cables 282A, 284A can extend therethrough as shown.

Thus, each tension spring assembly 286A, 286B is structured to provide strain relief. For example, if the steerable tip 156 has force applied thereto from an external source (such as a user's hand or collision of the tip 156 with an object), that external force is applied to one or both of the cable housings 282B, 284B. Given that each of the cable housings 282B, 284B is longitudinally incompressible, the force is transferred axially along the length of the housing 282B, 284B and into the retainer body 300A, 300B, which causes the tension spring 308A, 308B to be urged from its relaxed state toward either its compressed or its extended state. All of this occurs without any external force being applied to the inner cable 282A, 284A. Thus, each tension spring assembly 286A, 286B helps to prevent damage to the cables 228A, 228B by absorbing any application of external force thereto through the cable housings 282B, 284B and tension springs 308A, 308B. That is, compression of the tension springs 308A, 308B allows for adjustment of the length of the cable housing 282B, 284B as a result of the external force while protecting the inner cables 282A, 284A from that external force.

Alternatively, the configuration of the tension spring assemblies 286A, 286B need not be limited to the specific components thereof. It is understood that any known assembly for absorbing strain from external forces can be incorporated herein.

Turning now to the tension adjustment mechanisms 288A, 288B, each such assembly 288A, 288B is operable to allow for manually adjusting the tension of each inner cable 282A, 284A. That is, if a user determines that either cable 282A, 284A is too loose or too tight, the user can utilize the appropriate adjustment mechanism 288A, 288B to adjust the tension thereof. Each mechanism 288A, 288B includes the extendable barrel 310A, 310B extending from a distal end of the retainer body 300A, 300B, as discussed above. Each adjustable barrel 310A, 310B has an adjuster nut 314A, 314B that is threadably coupled to the barrel 310A, 310B such that rotation of either nut 314A, 314B by a user causes axial extension or retraction of the respective barrel 310A, 310B. Thus, if either cable 282A, 284A is too loose, the user can rotate either nut 314A, 314B to lengthen the respective barrel 310A, 310B, thereby tightening the cable 282A, 284A. On the other hand, if either cable 282A, 284A is too tight, the user can rotate either nut 314A, 314B to shorten the appropriate barrel 310A, 310B, thereby loosening the cable 282A, 284A.

Alternatively, the configuration of the tension adjustment assemblies 286A, 286B need not be limited to the specific components thereof. It is understood that any known assembly for adjusting the tension of the cables can be incorporated herein.

Further, it is understood that the various camera body embodiments disclosed or contemplated herein are not limited to the specific components and features discussed above. That is, the camera body/handle can incorporate any known mechanisms or components for lighting, transmission of energy/information, articulation, and adjustment/strain relief mechanisms.

Figure 11A:
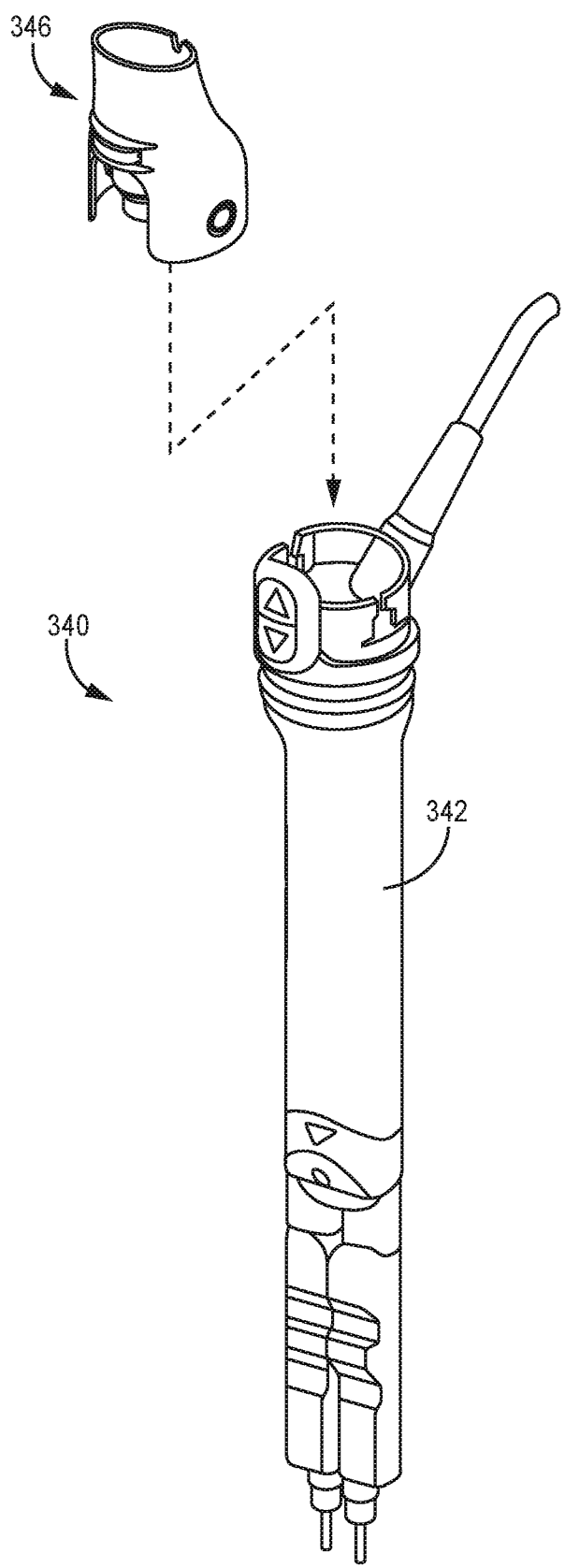
FIG. 11A is a perspective view of an elongate body and robotic arms of a robotic device and a nest that is coupleable thereto, according to one embodiment.
Figure 11B:
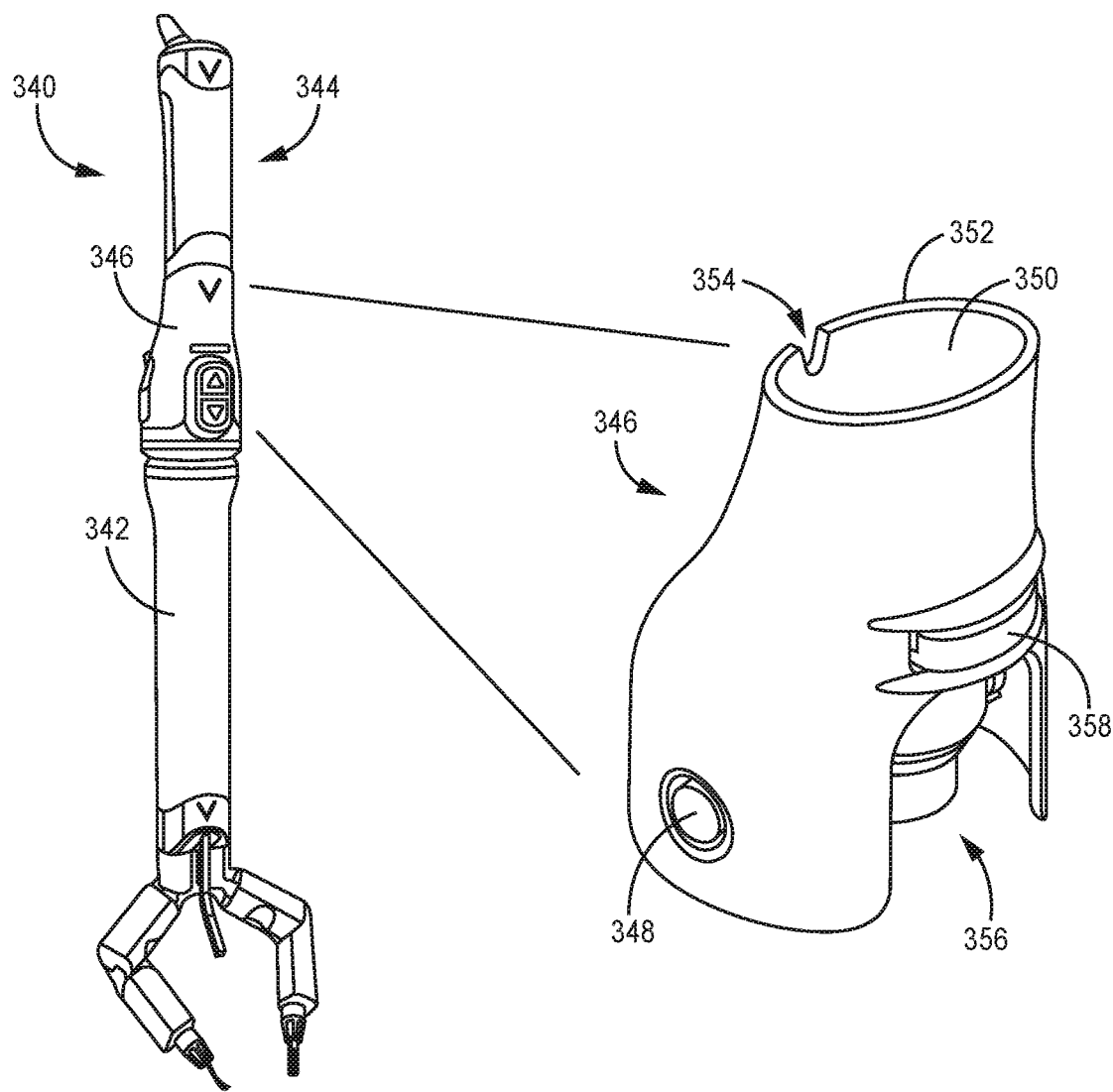
FIG. 11B is a perspective view depicting the robotic device of FIG. 11 with the nest and a camera coupled thereto, along with an expanded view of the nest itself, according to one embodiment.
Figure 13:
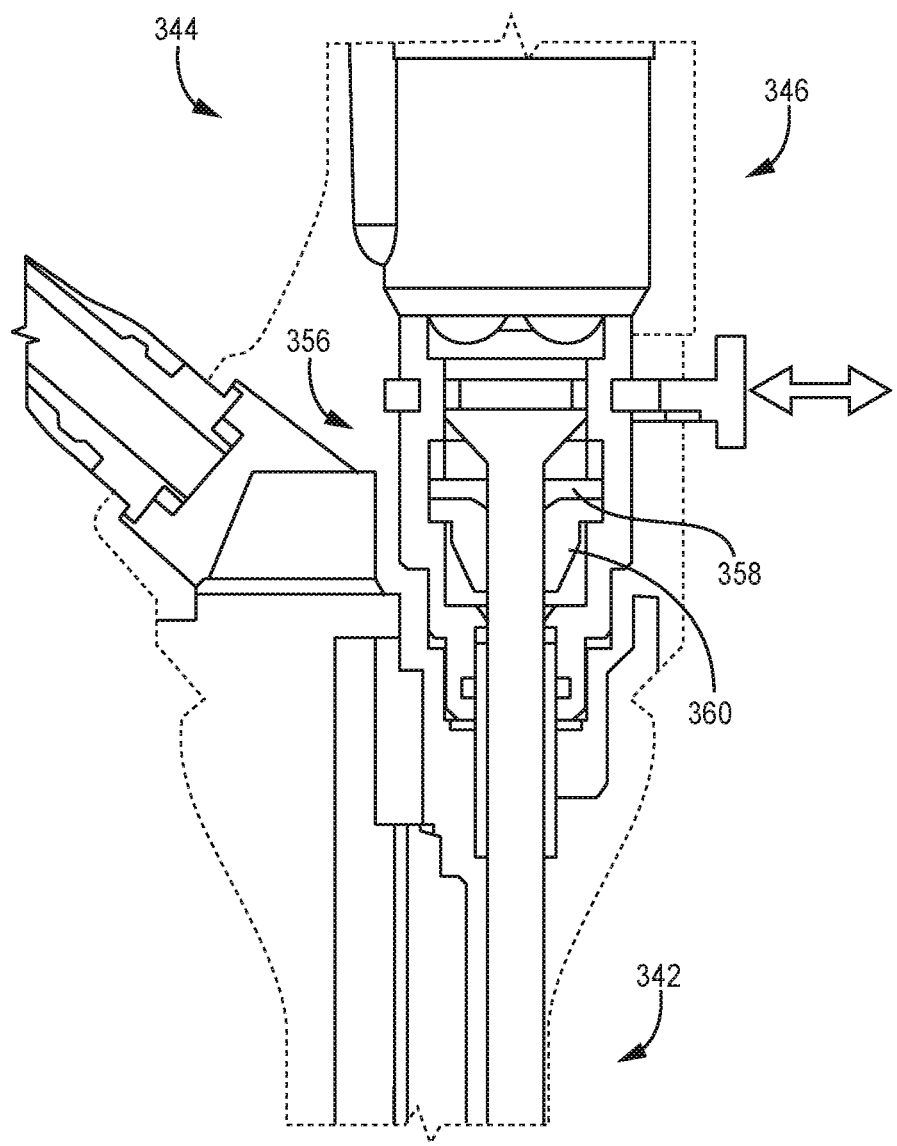
FIG. 13 is a cross-sectional cutaway view of a a proximal end of a device body with the nest of FIG. 11B attached thereto and a camera disposed therethrough, according to one embodiment.

As shown in FIGS. 11A and 11B, various implementations of the robotic device 340 can include a removable nest 346 that is removably coupleable to a proximal end of the device body 342 (as best shown in FIG. 11A) and is designed to receive an insertable camera assembly 344 (including, for example, any camera embodiment disclosed or contemplated herein) and couple or lock the device 340 and camera 344 together, as is shown in FIG. 13. That is, the nest 346 is a coupling component or port that can couple to both the device 340 and camera 344 as shown such that the nest 346 is disposed between the device body 342 and the camera 344 when the three components 342, 344, 346 are coupled together (as best shown in FIG. 11B and FIG. 13). In this embodiment, the nest 346 removably attaches to the proximal portion of the elongate body 342 as best shown in FIG. 11A, and can be released therefrom by the nest release buttons 348 as best shown in FIG. 11B (in which one of the two buttons 348 is visible, with the other button disposed on the opposing side of the nest 346). The release buttons 348 will be discussed in additional detail below. Further, as best shown in FIG. 11B, the nest 346 has a proximal opening 350 which is also known as the camera acceptance opening 350 that receives the camera (such as camera 344) such that the camera 344 mechanically couples or mates with the nest 346 in the opening 350. The lip 352 of the opening 350 in this embodiment includes a slot 354, which is a rotation registration feature 354 that mates with a matching feature (in this case, a protrusion) on the camera 344 to ensure that the camera 344 will only fully mate with the nest 346 in one specific orientation. Further, the nest 346 also has a seal package 356 disposed therein that helps to ensure the insufflation pressure in the target cavity of the patient does not leak out though the camera lumen (not shown) in the device body 342, regardless of whether the camera 344 is disposed in the lumen or not. In addition, the nest 346 has a camera lock/release button 358 as shown. Both the seal package 356 and the button 358 will be discussed in additional detail below.

Figure 12A:
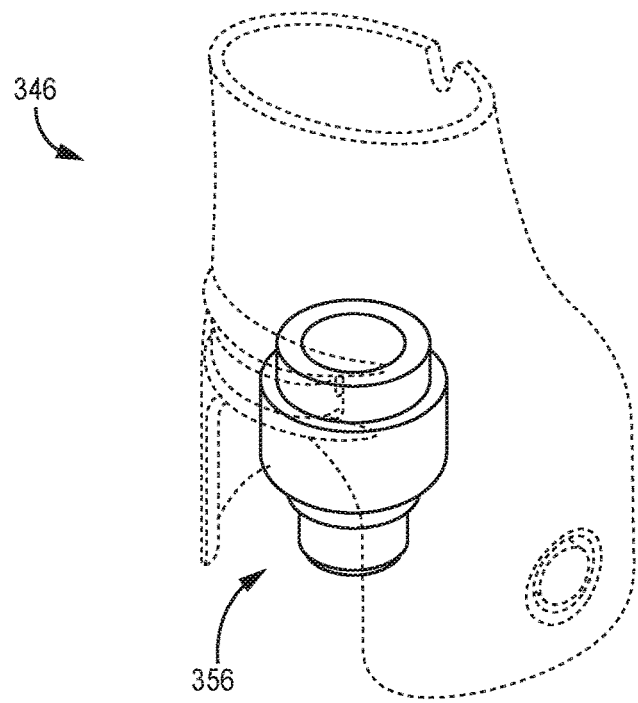
FIG. 12A is a perspective cutaway view of the nest of FIG. 11B and a seal package disposed therein, according to one embodiment.
Figure 12B:
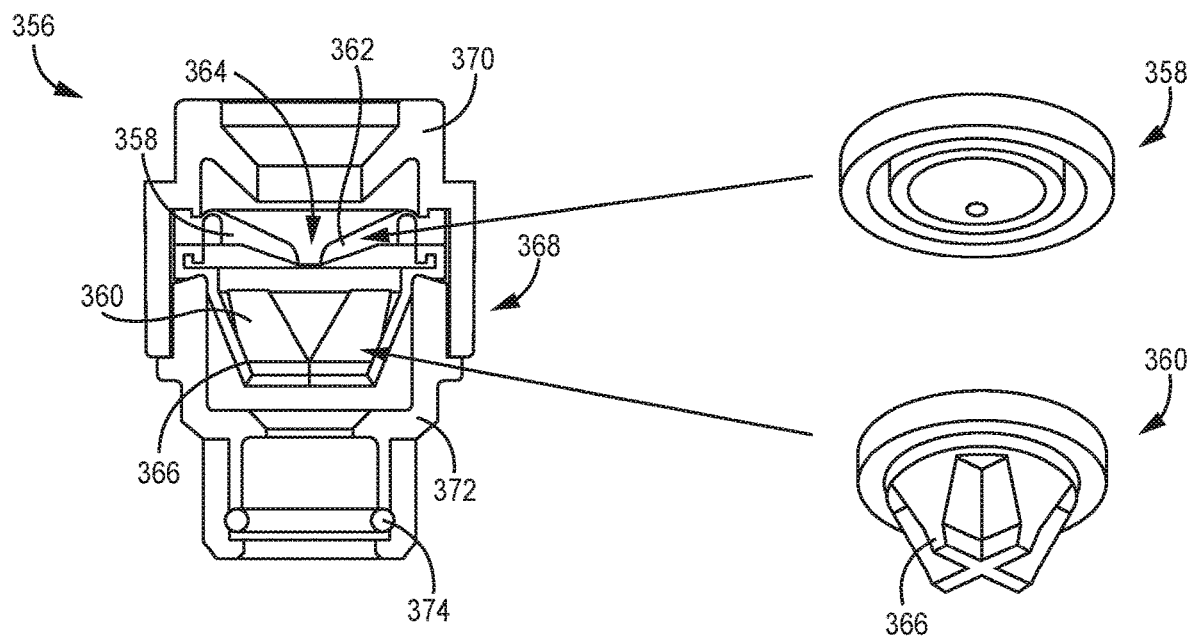
FIG. 12B is a cross-sectional cutaway view of the seal package of FIG. 12A, along with an expanded view of the two seals disposed therein, according to one embodiment.

One embodiment of the seal package 356 is depicted in FIGS. 12A and 12B. As best shown in FIG. 12A, the seal package 356 is disposed within the nest 346 such that the seal package 356 receives the camera (such as camera 344) as it is positioned in the nest 346 and thus disposed in and coupled to the device body 342 (as shown in FIG. 13). It is understood that the seal package 356 is any structure having at least one seal disposed therein for establishing a fluidic seal in the presence or absence of the camera. In various implementations, the structure 356 can have one seal, two seals, three seals, or any number of seals as needed to maintain the fluidic seal as described herein. As best shown in FIG. 12B, the seal package 356 in this exemplary embodiment has two seals: a first seal 358 and a second seal 360. In one embodiment as shown, the first seal 358 is disposed above the second seal 360. Alternatively, the second seal 360 can be disposed above the first seal 358.

As best shown in FIG. 12B, the first seal 358 is configured to receive the camera 344 and maintain a fluidic seal between the camera 344 and the seal 358. In the exemplary embodiment as shown, the seal 358 is a circular seal with tensioned seal walls 362 in which an opening 364 is defined. The opening 364 has a diameter that is less than the outer diameter of the camera 344 to be positioned therethrough. When the camera 344 is disposed through the opening 364 in the first seal 358 (as shown in FIG. 13, for example), the walls 362 are urged away from the center of the seal 358 as a result of the smaller diameter of the opening 364, thereby causing the tension in the walls 362 to increase. As such, the tension in the walls 362 causes the walls 362 to be urged toward the camera 344, thereby establishing a seal therebetween. Alternatively, the first seal 358 can be any seal that can receive a camera therethrough and establish a fluidic seal between the seal and the camera.

The second seal 360 is configured to maintain a fluidic seal when the camera is not disposed through the seal package 356. In this embodiment as shown, the seal 360 is a circular seal having hinged seal walls 366 that can move between an open position (when the camera is disposed therethrough) and a closed position (when the camera is not present) such that the closed walls 366 establish a fluidic seal. According to one implementation, the seal walls 366 are urged closed by the higher gas pressure inside the target cavity of the patient, thereby reducing or preventing leakage or loss of air pressure as a result. Alternatively, the second seal 360 can be any seal that can receive a camera therethrough and establish a fluidic seal when the camera is not present.

Continuing with FIG. 12B, the seal structure 356 also has a frame 368 having a top frame structure 370 and a bottom frame structure 372 coupled to the top frame structure 370. The two seals 358, 360 are disposed between the top and bottom frame structures 370, 372 as shown. In one embodiment, the bottom frame structure 372 also has a third seal 374 disposed therein. More specifically, in this specific embodiment, the third seal 374 is an O-ring seal 374. Alternatively, the third seal 374 can be any known seal.

In use, the seal package 356 allows for the camera 344 to be inserted or removed at any time, including during a procedure, without risking loss of insufflation. That is, the first seal 358 maintains a fluidic seal while the camera 344 is present (such as shown in FIG. 13), and the second seal 360 maintains a fluidic seal while the camera 344 is not present.

It is understood that the seal structure 346 embodiments disclosed or contemplated herein can be incorporated into any nest embodiment disclosed or contemplated herein. Further, it is also understood that any other known seal mechanisms or structures can be used to establish a fluidic seal within any nest embodiment for receiving any camera embodiment herein.

Figure 14A:
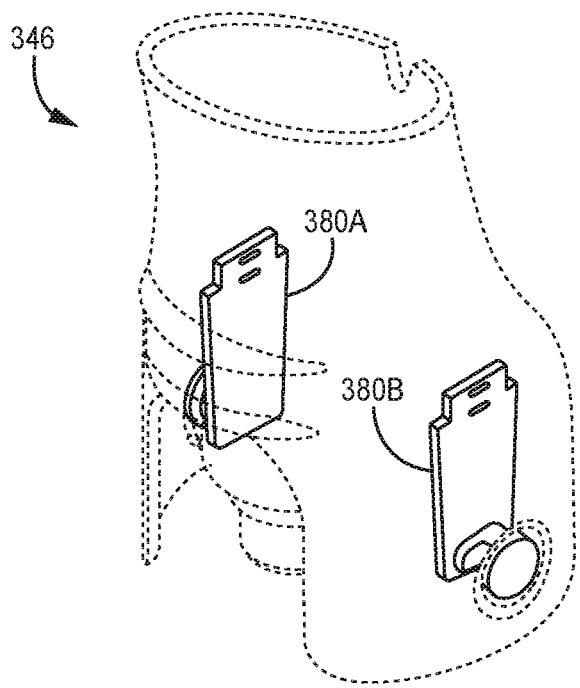
FIG. 14A is a cutaway view of the nest of FIG. 11B and two latches disposed therein, according to one embodiment.
Figure 14B:
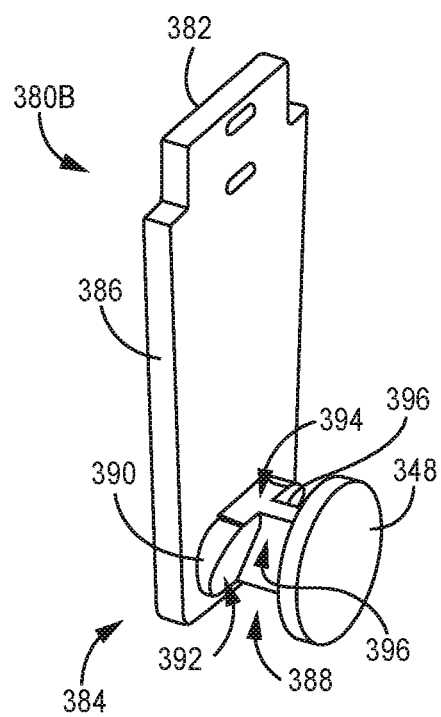
FIG. 14B is a perspective view of one of the latches of FIG. 14A, according to one embodiment.

Returning to the coupling of the nest 346 to the proximal end of the device body 342, FIG. 14A depicts two hinged latches 380A, 380B disposed within the nest 346 such that the latches 380A, 380B can be used to couple the nest 346 to the device body 342, and FIG. 14B depicts an expanded view of one of those latches 380B. The latches 380A, 380B are coupling mechanisms that can be used to both couple the nest 346 to the proximal end of the device body 342 and to uncouple therefrom. While FIG. 14B depicts solely the hinged latch 380B for purposes of describing the latch 380B in further detail, it is understood that the other hinged latch 380A has substantially the same or similar components. The latch 380B has a proximal end 382 that is hingedly coupled to or cantilevered from an interior portion of the nest 346 such that the distal end 384 of the latch 380B is movable in relation to the nest 346. Further, each latch 380A, 380B is hingedly attached in such a fashion that the latches 380A, 380B are tensioned such that when the latches 380A, 380B are urged radially inward, force is applied to the latches 380A, 380B such that the force is directed to urge them back to their natural state (and thus the force is applied such that the latches 380A, 380B are urged radially outwardly). In addition, the latch button 348 discussed above with respect to FIG. 11B is disposed at the distal end of the latch 380B, with the latch button 348 coupled to the latch body 386 via an arm 388 such that the button 348 is disposed at a distance from the latch body 386. The arm 388 has several structural features that assist with interaction with and coupling/uncoupling of the latch 380B in relation to the device body 342. That is, the arm 388 includes a protrusion or protruding body 390 with an angled surface 392 on the side of the protrusion 390 and a nest latching surface 394 on the top of the protrusion 390. Further, the sides of the arm 388 are guidance surfaces 396. The functions of these surfaces are explained in detail below.

Figure 15A:
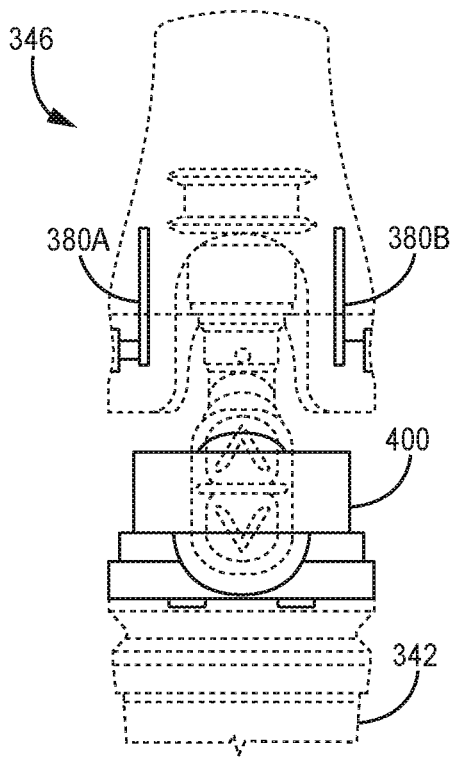
FIG. 15A is a side cutaway view of the nest of FIG. 11B disposed adjacent to the proximal end of the robotic device body of FIG. 11A, according to one embodiment.
Figure 15B:
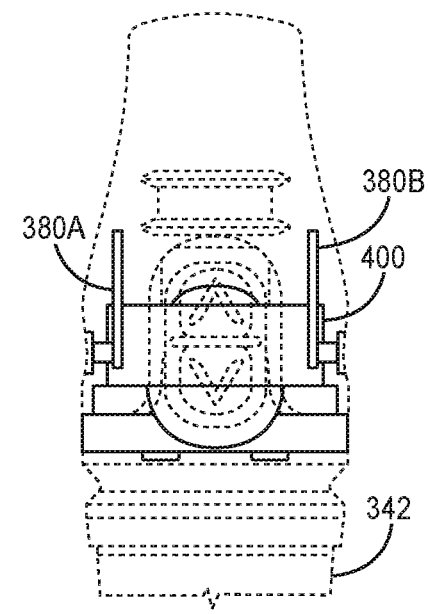
FIG. 15B is a side cutaway view of the nest and device body of FIG. 15A coupled together, according to one embodiment.

FIGS. 15A and 15B show the coupling of the nest 346 to the proximal end of the device body 342. More specifically, FIG. 15A depicts the nest 346 positioned in close proximity to the proximal end of the body 342, while FIG. 15B depicts the nest 346 coupled to the proximal end of the body 342. The proximal end of the device body 342 has a male connector 400 disposed on the proximal end of the body 342 that is configured to couple with the nest 346 such that the nest 346 is disposed over the male connector 400 when the nest 346 is coupled thereto.

Figure 16A:
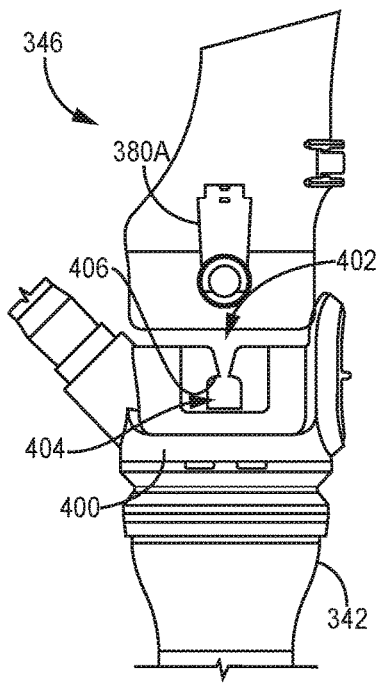
FIG. 16A is a side cutaway view of the nest of FIG. 11B disposed adjacent to the male connector of the device body of FIG. 11A, according to one embodiment.
Figure 16B:
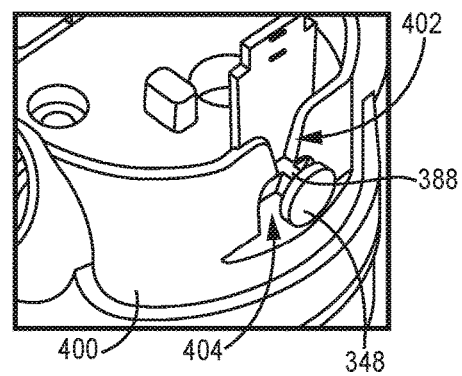
FIG. 16B is a perspective expanded view of one latch of the nest of FIG. 16A being coupled with the male connector of FIG. 16A, according to one embodiment.

FIGS. 16A-17B depict the operation of the hinged latches 380A, 380B in coupling the nest 346 to the device body 342. As best shown in FIGS. 16A and 16B, the male connector 400 has V-shaped receiving slots 402 defined on both sides thereof, with only one of the slots 402 depicted in the figures. The slots 402 are disposed on opposing sides of the connector 400 and are aligned to receive the two hinged latches 380A, 380B. Further, as also shown in FIGS. 16A and 16B, the slot 402 (and the undepicted slot on the opposing side of the connector 400) is in communication with a protrusion receiving opening 404 that is also defined in the side of the connector 400. Again, the connector has two such protrusion receiving openings, with one such opening 404 depicted and the other opening positioned on the opposing side of the connector 400 but not depicted in the figures.

Figure 17A:
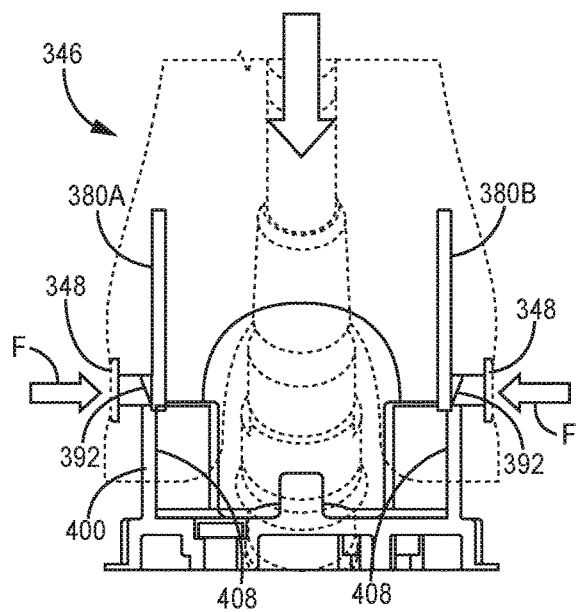
FIG. 17A is a side cutaway view of the nest of FIG. 11B disposed adjacent to the male connector of the device body of FIG. 11A, according to one embodiment.
Figure 17B:
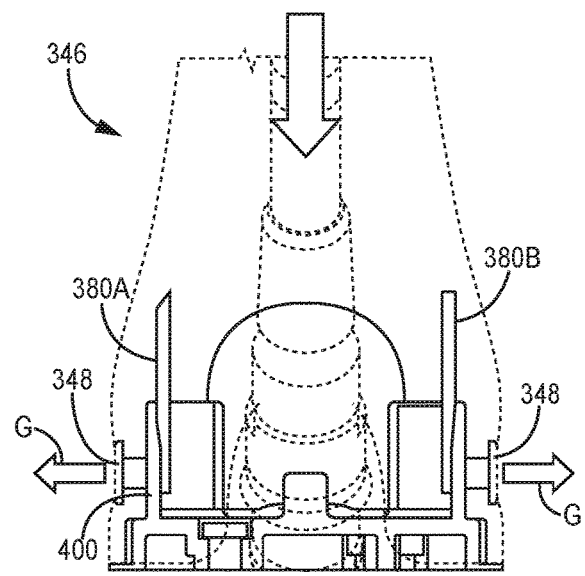
FIG. 17B is a side cutaway view of the nest and male connector of FIG. 17A coupled together, according to one embodiment.

Thus, as the nest 346 is urged downward toward the male connector 400, the latches 380A, 380B are aligned with the V-shaped slots (including the slot 402), as best shown in FIG. 16A, such that the guidance surfaces 396 of the arms 388 are aligned as well. As the distal ends 384 of the latches 380A, 380B approach and come into contact with the connector 400 (as best shown in FIG. 17A), the arms 388 are aligned with the V-shaped slots 402 and the angled surfaces 392 contact the inner walls 408 of the connector 400. Thus, as the nest 346 is urged further downward, the V-shaped slots 402 help to guide the arms 388 of the latches 380A, 380B and the angled surfaces 392 contacting the inner walls 408 cause the distal ends of the latches 380A, 380B to be urged radially inward, as indicated by the arrows F in FIG. 17A. Once the nest 346 is urged into full connection with the connector 400, the protrusions 390 of the latches 380A, 380B are positioned parallel with the protrusion receiving openings 404 such that the tensioned nature of the latches 380A, 380B results in the latches 380A, 380B being urged radially outwardly such that the protrusions 390 are urged into the openings 404. That is, the distal ends of the latches 380A, 380B and the buttons 348 thereon are urged radially outwardly as depicted by the arrows G in FIG. 17B. At this point, the nest latching surfaces 394 are disposed to be in contact with the upper walls 406 of the openings 404, thereby retaining the latches 380A, 380B in place.

When the nest 346 is coupled to the device body 342 as described herein, the latches 380A, 380B are releasably locked to the male connector 400 as described above. Thus, in order to remove the nest 346, a user must reverse the process described above by pressing both buttons 348 on the latches 380A, 380B, thereby urging the distal ends of the latches 380A, 380B radially inwardly such that the nest latching surfaces 394 are no longer in contact with the upper walls 406. As such, once the buttons 348 are depressed far enough, the latches 380A, 380B release and the nest 346 can be urged proximally off of the proximal end of the device body 342, thereby removing the nest from the device 340.

It is understood that the latch 380A, 380B embodiments disclosed or contemplated herein can be incorporated into any nest embodiment disclosed or contemplated herein, and can be used to couple to any device body disclosed or contemplated herein. Further, it is also understood that any other known attachment mechanisms can be used to removably couple any nest embodiment herein to any device body herein.

Figure 18:
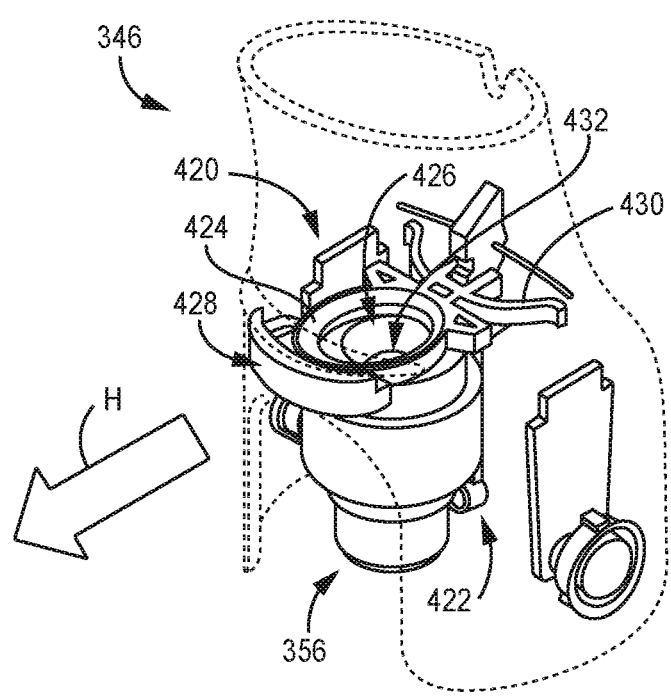
FIG. 18 is a perspective cutaway view of the nest of FIG. 11B with a camera coupling mechanism disposed therein, according to one embodiment.

As shown in FIG. 18, once the nest 346 is coupled to the device body 342 as described above, the nest 346 can have a camera coupling mechanism (or "latch mechanism") 420 that can be used to couple the camera (such as camera 344) to the nest 346 and thus the device 340, according to one embodiment. Further, the mechanism 420 can also be used to release or uncouple the camera 344 from the device body 342. In addition, the mechanism 420 can also have a presence detection mechanism 422 coupled thereto that can operate in conjunction with the latch mechanism 420 to detect the presence or absence of the camera 344. Both the camera coupling mechanism 420 and the presence detection mechanism 422 will be described in further detail below.

Continuing with FIG. 18, the camera latch mechanism 420 has a slidable latch body 424 with a camera receiving opening 426 defined therein as shown. The camera receiving opening 426 is disposed above the camera lumen 432 in the seal package 356 as shown. Further, the coupling mechanism 420 also has a latch button 428 attached to the body 424 on one side, and a tension spring 430 attached to the body 424 on the side opposite the button 428 as shown. The tension spring 430 is configured to urge the latch body 424 away from the spring 430 as shown by arrow H such that the opening 426 is not aligned with the camera lumen 432 in the seal package 356.

Figure 19A:
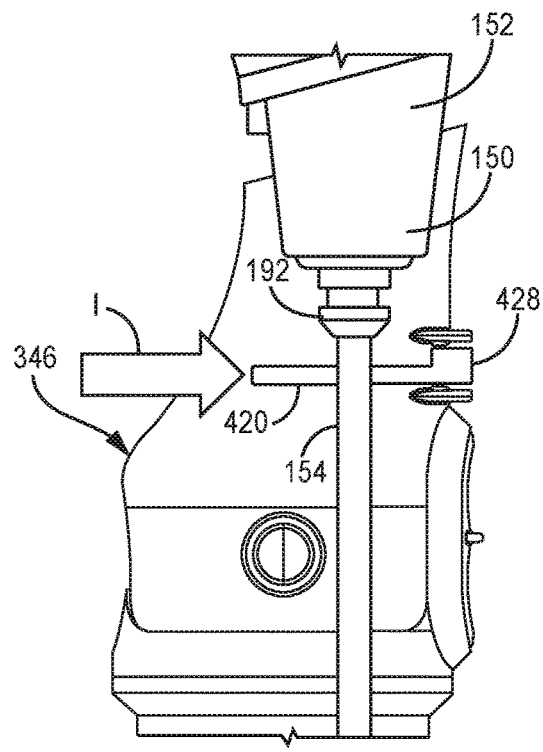
FIG. 19A is a side cross-sectional cutaway view of the nest and camera coupling mechanism of FIG. 18 in which the camera is not yet coupled to the nest, according to one embodiment.
Figure 19B:
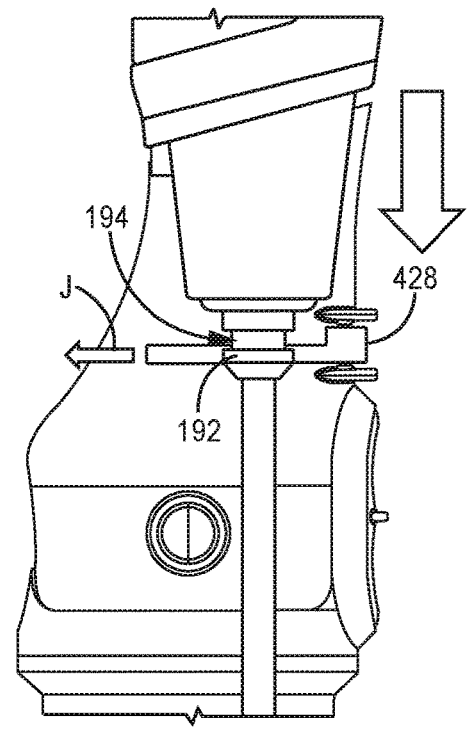
FIG. 19B is a side cross-sectional cutaway view of the nest and camera coupling mechanism of FIG. 18 in which the camera is being urged into its fully coupled position in the nest, but is not yet fully coupled, according to one embodiment.
Figure 19C:
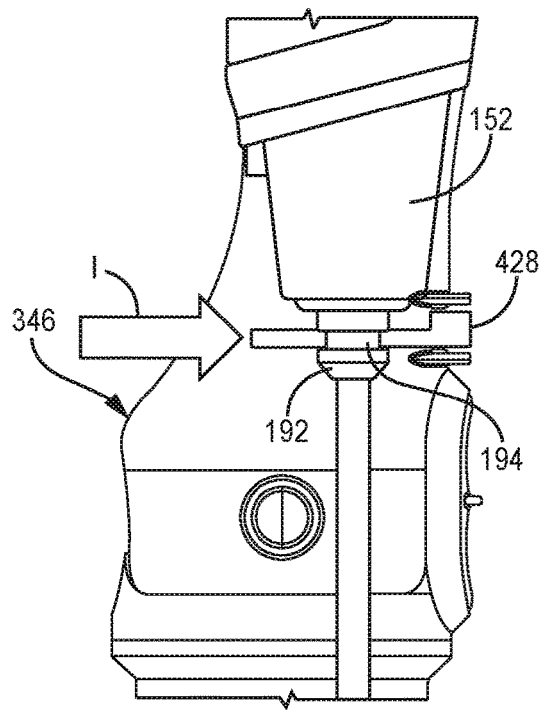
FIG. 19C is a side cross-sectional cutaway view of the nest and camera coupling mechanism of FIG. 18 in which the camera is fully coupled to the nest, according to one embodiment.

Insertion of a camera 150 into the nest 346 (and thus the device 340) and the resulting interaction with the camera latch mechanism 420 will now be described with respect to FIGS. 19A-19C, according to one embodiment. As shown in FIG. 19A, as the shaft 154 of the camera (such as camera 150) is inserted into the nest 346 but before the distal end of the handle 152 reaches the latch mechanism 420, the tension spring 430 continues to urge the mechanism 420 toward the button in the direction represented by arrow I. As shown in FIG. 19B, when the camera 150 is urged distally into the nest 346 such that the nose cone tip 192 is urged through the opening 426 in the latch body 424, the tip 192 contacts the body 424 and urges the body 424 back toward the tension spring 430 as represented by arrow J. This allows for passage of the tip 192 through the opening 426 in the latch body 424. As shown in FIG. 19C, once the tip 192 passes through the opening 426, the latch receiving slot 194 is disposed in the opening 426, which releases the force applied by the tip 192 and allows the force of the tension spring 430 to once again urge the latch body 424 away from the spring 430 as again represented by arrow I. This urges the latch body 424 into the slot 294 in the camera 150, thereby coupling the latch mechanism 420 and the camera 150 such that the camera 150 is locked into place in the nest 346 and thus the elongate body 342. When it is desirable to remove the camera 150, a user can depress the button 428, thereby urging the latch mechanism 420 toward the latch springs, thereby urging the latch body 424 out of the slot 194, which releases the camera 150 such that a user can remove it proximally from the nest 346 and the device body 342.

It is understood that the camera coupling mechanism 420 embodiments disclosed or contemplated herein can be incorporated into any nest embodiment disclosed or contemplated herein, and can be used to couple to camera embodiment disclosed or contemplated herein. Further, it is also understood that any other known camera coupling mechanisms can be used to removably couple any camera embodiment herein to any device body herein.

Figure 20:
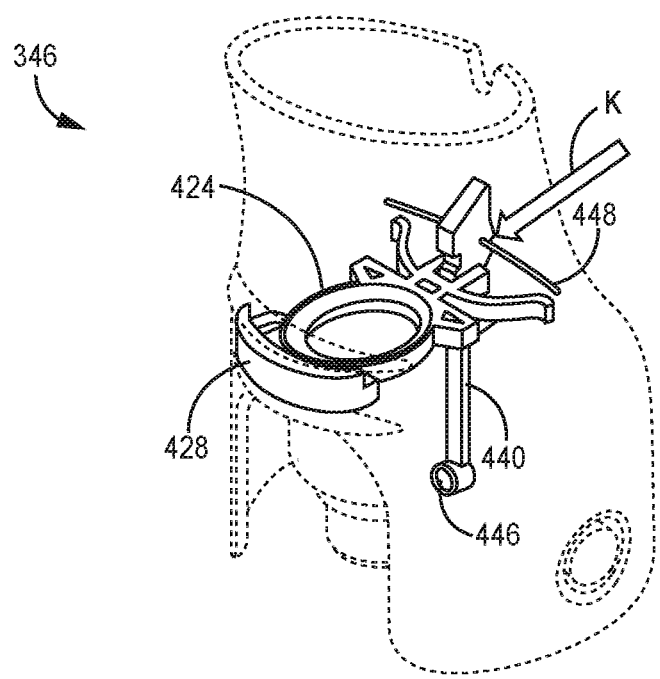
FIG. 20 is a perspective cutaway view of the nest of FIG. 11B with a presence detection mechanism disposed therein, according to one embodiment.
Figure 21:
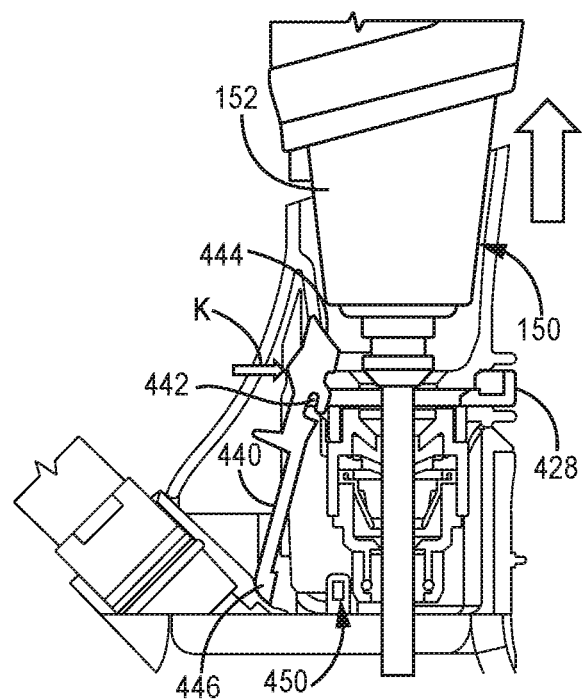
FIG. 21 is a side cross-sectional cutaway view of the nest and presence detection mechanism of FIG. 20 in which the camera is not yet coupled to the nest, according to one embodiment.

As mentioned above, the nest 346 also has a presence detection mechanism 422 that will now be described in detail with respect to FIGS. 20-22B, according to one embodiment. The mechanism 422 includes a lever 440 that is pivotally coupled to the latch body 424 at a pivot point 442 as best shown in FIG. 21. The lever 440 has a contact pad 444 at one end of the lever 440 as shown, and a magnet 446 at the opposite end of the lever 440. In addition, the detection mechanism 422 also includes a tension spring 448 in contact with the lever 440 at a point along the lever identified by arrow K as best shown in FIGS. 20 and 21, such that the tension spring 448 urges the lever 440 to rotate clockwise around the pivot point 442 as shown in FIG. 21. Further, the detection mechanism 422 includes a sensor 450 disposed in a proximal end of the device body 342 such that the magnet 446 on the lever 440 is configured to interact with the sensor 450 as described in further detail below.

According to one embodiment, the presence detection mechanism 422 can detect three different configurations: (1) the presence of the fully installed camera (such as camera 150), (2) the proper coupling of the nest 346 to the device body 342, and (3) actuation of the camera release button 428 by a user. Each of these will be described in turn below.

FIG. 21 depicts the presence detection mechanism 422 when the camera 150 is not yet coupled properly to the nest 346 and device body 342. Because the camera body 152 is not positioned adjacent to and in contact with the contact pad 444, the force applied by the tension spring 448 urges the portion of the lever 440 forward, which urges the magnet 446 away from the sensor 450. The gap between the magnet 446 and the sensor 450 causes the sensor 450 to indicate that the magnet 446 is not in contact with the sensor 450, thereby indicating that the camera 150 is not properly coupled to the device body 342.

Figure 22:
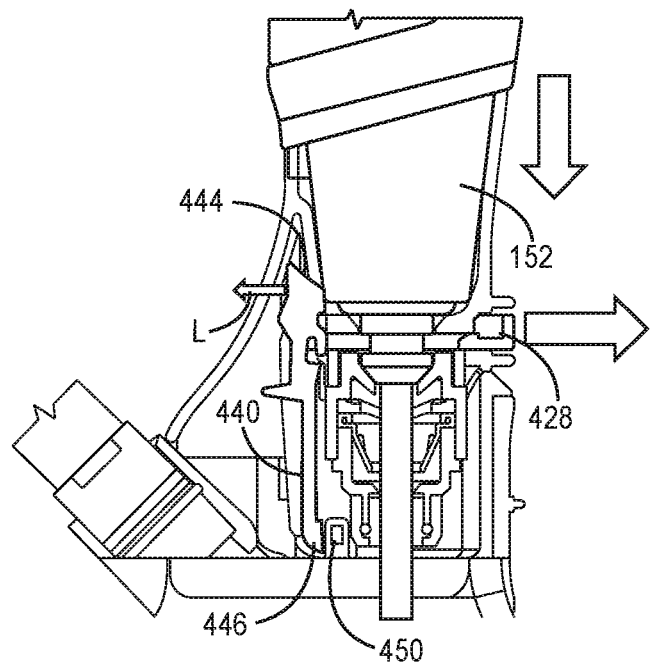
FIG. 22 is a side cross-sectional cutaway view of the nest and presence detection mechanism of FIG. 20 in which the camera is coupled to the nest, according to one embodiment.

FIG. 22 depicts the present detection mechanism 422 when the camera 150 is properly coupled to the nest 346 and the device body 342. With the camera body 152 positioned in contact with the contact pad 444, that urges the contact pad 444 and thus the portion of the lever 440 above the pivot point 442 radially outward as represented by arrow L. Thus, the magnet 446 is urged into contact with the sensor 450 such that the sensor 450 indicates the presence of the magnet 446, thereby indicating that the camera 150 is properly coupled to the device body 342. In addition, this position of the lever 440 and contact of the magnet 446 with the sensor 450 also indicates that the nest 346 is properly coupled to the device body 342.

Figure 23:
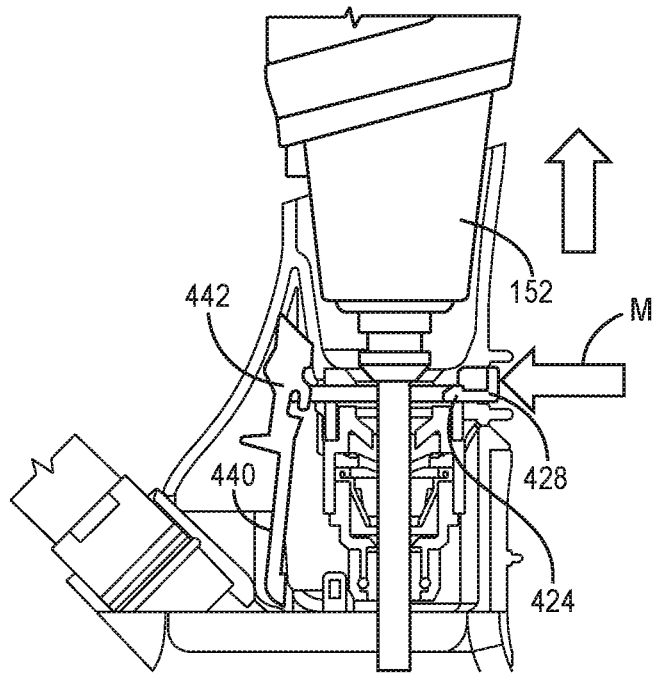
FIG. 23 is a side cross-sectional cutaway view of the nest and presence detection mechanism of FIG. 20 in which the camera coupling mechanism button has been depressed, according to one embodiment.

FIG. 23 depicts the present detection mechanism 422 when the camera latch button 428 is depressed by a user as indicated by arrow M. Given that the lever 440 is pivotally coupled to the latch body 424 at the pivot point 442, the depression of the latch button 428 causes the pivot point 442 to move away from the button 428 (in the direction of arrow M). The movement of the pivot point 442 in combination with the force applied by the tension spring 448 causes the portion of the lever 440 below the pivot point 442 to move radially outward such that the magnet 446 is urged away from the sensor 450. The gap between the magnet 446 and the sensor 450 causes the sensor 450 to indicate that the magnet 446 is not in contact with the sensor 450, thereby indicating that the button 428 has been depressed. This indication of the depression of the button 428 is a precursor to removal of the camera. Thus, in certain embodiments, the overall system might use this information to straighten the camera tip (bring the tip co-axial with the camera shaft) so that it can be more easily removed, or take any other similar steps.

Alternatively, the magnet 446 need not be a magnet. Instead, the component at the end of the lever 440 can be any sensor component or sensor detectable component that can interact with the sensor 450 to indicate whether that end of the lever 440 is in contact (or close proximity) with the sensor 450 or is not in proximity with the sensor 450. For example, both the component 446 and the sensor 450 can be sensors that can sense the presence of the other sensor. Alternatively, the component 446 and the sensor 450 can be any types of mechanisms that provide for sensing the presence or absence of that end of the lever 440.

It is understood that the presence detection mechanism embodiments disclosed or contemplated herein can be incorporated into any nest embodiment disclosed or contemplated herein. Further, it is also understood that any other known presence detection mechanisms can be used in any nest embodiment herein to detect the presence of any camera embodiment herein.

It is understood that the various nest embodiments disclosed or contemplated herein are not limited to the specific coupling and uncoupling mechanisms, sensors, etc. as described above with respect to the exemplary nest embodiment described herein. It is understood that other known mechanisms or components that can accomplish the same results can be incorporated herein.

In one implementation, the various device embodiments herein can have fluidic seals at all potential fluid entry points in the device, thereby reducing or eliminating the risk of fluid entering any of the internal areas or components of the device. For example, in one embodiment, each of the robotic arms in the device can have fluidic seals disposed at certain locations within the arms to reduce or prevent fluidic access to the internal portions of the arms. In addition, the arms can also have a flexible protective sleeve disposed around the arms as discussed above. The sleeve at one end is attached at the distal end of the elongate device body and at the other end is attached at the distal end of the forearm of each arm.

Figure 24:
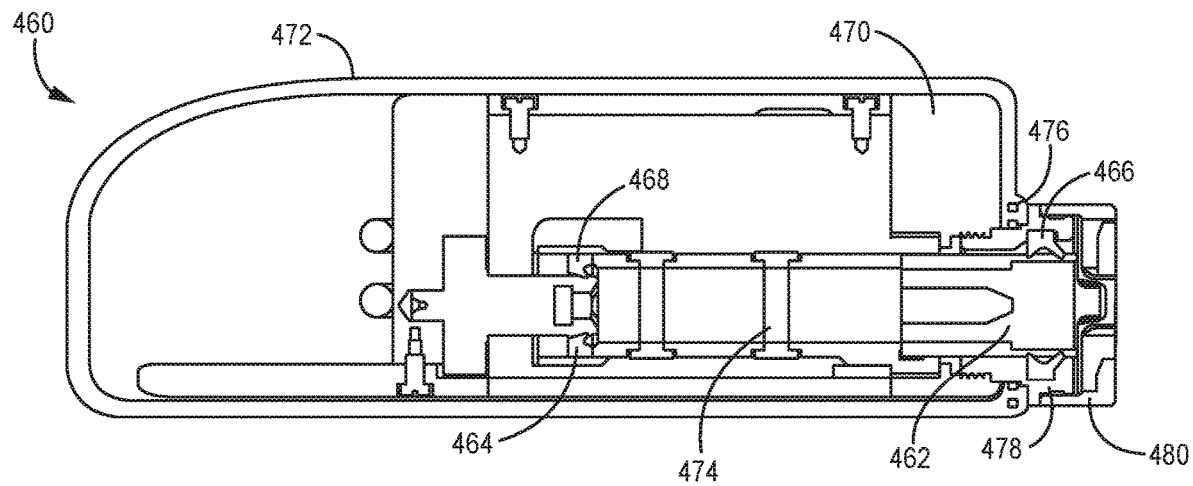
FIG. 24 is a cross-sectional cutaway view of a forearm, according to one embodiment.

One exemplary forearm 460 with appropriate fluidic seals is depicted in FIGS. 23 and 24, according to one embodiment. As best shown in FIG. 23, the forearm 460 has a tool lumen 462 defined therein, with a tool drive 464 disposed at the proximal end of the lumen 462. Further, the forearm 460 has a protective sleeve 472 around the forearm body 470 and fluidic seals at both ends of the lumen 462: a proximal seal 468 at the proximal end and an arrangement of seals at the distal end. As best shown in FIG. 24, the arrangement of seals at the distal end of the forearm 460 includes a seal 476 (which can be a compression ring 476) that engages the protective sleeve 472 and retains it in place around the opening to the tool lumen 462. The seal 476 can be molded into the protective sleeve 472 or alternatively can be a separate component. In addition, the arrangement of distal seals also includes a threaded seal holder 478 that is threaded into the lumen opening in the forearm body 470. This holder 478 compresses the seal 476 and the protective sleeve 472, thereby forming a fluidic seal between the protective sleeve 472 and the threaded seal holder 478. In certain implementations, the threaded seal holder 478 is removable, thereby allowing the protective sleeve 472 to be removed and replaced as necessary. Further, the arrangement of distal seals includes a ring seal 466 that can be positioned to form a seal between the threaded seal holder 478 and the tool lumen 462 while still allowing relative rotation between the tool lumen 462 and the forearm body 470. Finally, a tool bayonet 480 is positioned over the seal assembly as shown. The bayonet 480 is configured to receive and couple to any interchangeable end effectors (not shown) that are inserted into the tool lumen 462. It is understood that the bayonet interface 480 can be used to allow only certain end effectors to be inserted into the forearm 460.

The fluidic seals 466, 468 establish a fluidic seal between the tool lumen 462 and the internal areas and components of the forearm body 470. More specifically, each of the fluidic seals 466, 468 prevent fluid ingress while still allowing the tool lumen body 474 to rotate relative to the forearm body 470. The distal seal 466 establishes a fluidic seal between the tool lumen 462 and the protective sleeve 472, as mentioned above, while the proximal 468 seal establishes a fluidic seal between the tool lumen 462 and the internal portions of the body 470, thereby preventing fluids that enter the lumen 462 from accessing the internal portions of the body 470. As such, the two seals 466, 468 in combination with the protective sleeve 472 and the rest of the distal seal assembly discussed above prevent fluid from entering the forearm body 470 even if an end effector (not shown) is not present in the tool lumen 462.

Figure 25:
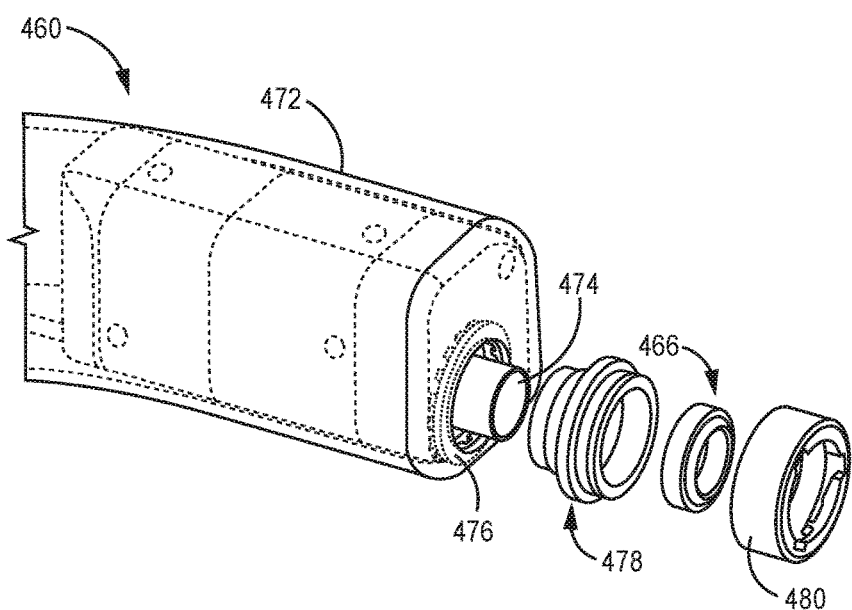
FIG. 25 is a perspective view of the forearm of FIG. 24, according to one embodiment.
Figure 27:
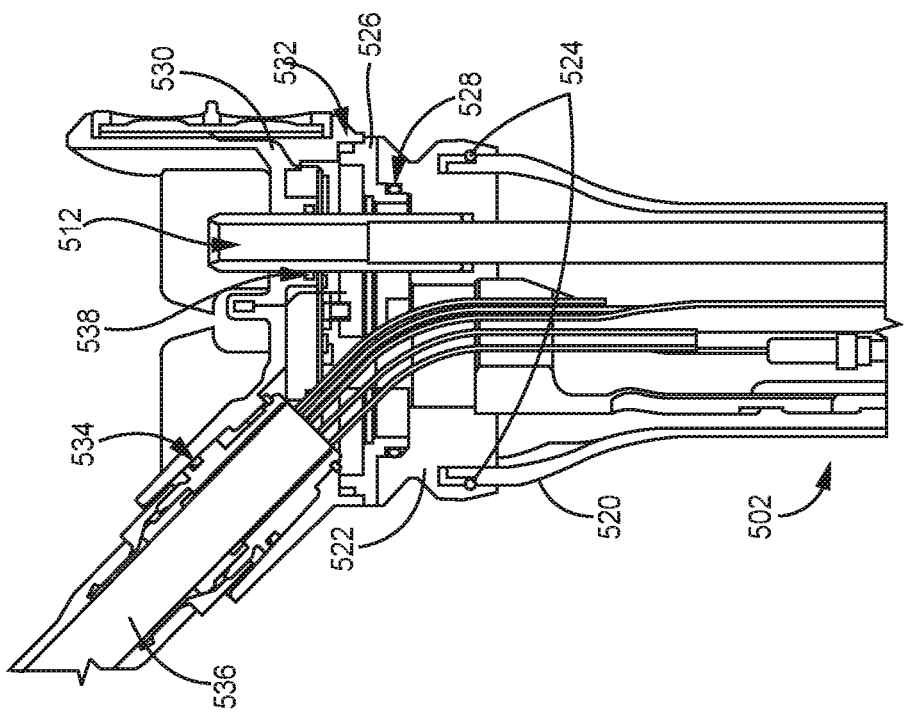
FIG. 27 is a cross-sectional cutaway view of the proximal end of the device body of FIG. 26, according to one embodiment.

As shown in FIG. 25, a fluidic seal is also established at the shoulder joint 500 between the device body 502 and the upper arm 504. As discussed above, the protective sleeve 472 is disposed around the upper arm 504 and extends across the shoulder joint 500 to the elongate body 502. In one embodiment as shown, the sleeve 472 is mechanically retained against the elongate body 502 with a retention band 506 that is disposed around the sleeve 472 at a groove 508 formed in the body 502 such that the band 506 pulls the sleeve 472 into the groove 508. Further, according to certain implementations, the sleeve 472 can have two seals 510 molded or otherwise formed into the sleeve 472 itself as shown. These bands 510 extend around the outer circumference of the sleeve 472 and act similarly to two O-rings by establishing a redundant compression seal between the sleeve 472 (at the bands 510) and the robot assembly. The camera lumen 512 in the device body 502 extends past and adjacent to the sleeve 472 such that it allows the camera (not shown) to be positioned therethrough and pass by the protective sleeve 472 and extend in front of the body 502 unencumbered.

Figure 26:
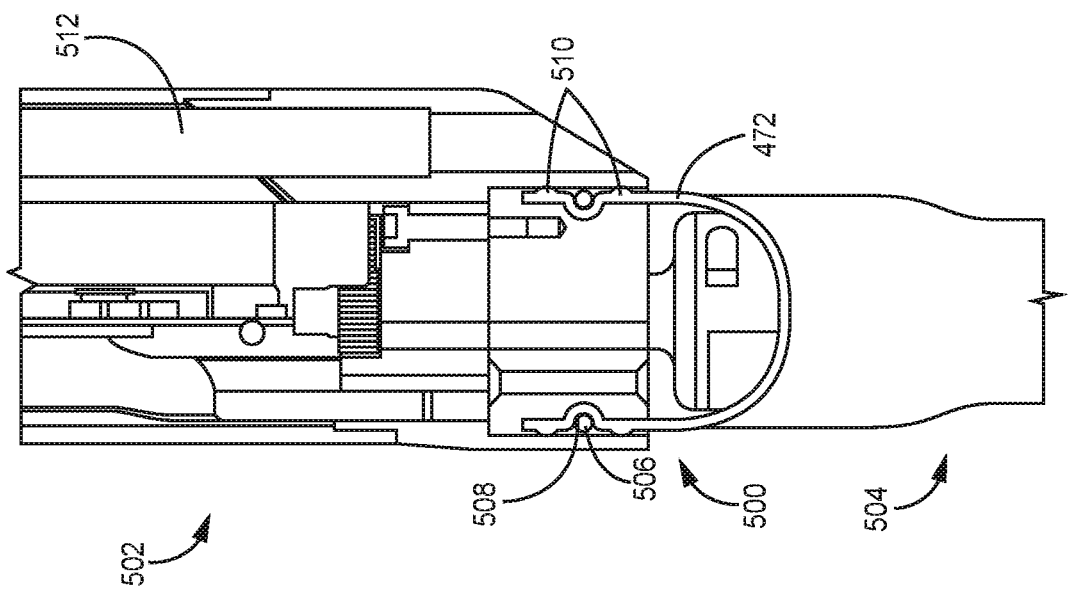
FIG. 26 is a cross-sectional cutaway view of an upper arm coupled to a device body at the shoulder joint, according to one embodiment.

As shown in FIG. 26, a fluidic seal is also established at the proximal end of the elongate device body 502 via several seals to prevent fluid ingress. First, the body housing 520 is coupled to the groove ring body 522 with a seal 524 (such as, for example, an O-ring 524) to establish a fluidic seal between the housing 520 and the groove ring body 522. Further, a fluidic seal is established between the groove ring body 522 and the light ring 526 with another seal 528 (such as, for example, an O-ring seal 528). Finally, a fluidic seal is established between the light ring 526 and the male connector 530 with another seal 532 (such as, for example, an O-ring seal 532). In certain embodiments, there can also be seals 534 where the electrical cable 536 enters the elongate body 502 and also seals 538 where the elongate body is pierced by the camera lumen 512.

It is understood that the fluidic seals as disclosed or contemplated herein can be incorporated into any device embodiment disclosed or contemplated herein. Further, it is also understood that any other known seal mechanisms can be used and positioned in any known fashion in any device embodiment herein to establish a fluidic seal for any device embodiment herein.

Although the various inventions have been described with reference to preferred embodiments, persons skilled in the art will recognize that changes may be made in form and detail without departing from the spirit and scope thereof.

What is claimed is:

1. A robotic surgical system, comprising:
   (a) a robotic surgical device comprising:
      (i) an elongate device body comprising a distal end and a proximal end;
      (ii) a removable connection port disposed at the proximal end of the device body, the connection port comprising:
         (A) a device body coupling mechanism disposed within the connection port;
         (B) an camera receiving opening defined in a proximal end of the connection port;
         (C) a seal package disposed in the removable connection port, the seal package comprising at least two seals; and
         (D) a camera coupling mechanism disposed within the removable connection port; and
      (ii) first and second robotic arms operably coupled to the distal end of the device body; and
   (b) a removable camera component removably disposable in the camera receiving opening and through the seal package, the removable camera component comprising a camera body, an elongate camera tube, a flexible section, and a distal imager; and
   (c) a presence detection mechanism comprising:
      (i) a rotatable lever operably coupled to the camera coupling mechanism at a pivot point, wherein the rotatable lever rotates around the pivot point;
      (ii) a first sensing component disposed on the rotatable lever; and
      (iii) a second sensing component disposed on the elongate body, wherein the second sensing component is configured to sense the presence or absence of the first sensing component.

2. The robotic surgical system of claim 1, wherein the device body coupling mechanism comprises first and second hinged coupling mechanisms hingedly coupled to the connection port.

3. The robotic surgical system of claim 2, wherein each of the first and second hinged coupling mechanisms comprises:
   (a) a coupling mechanism body;
   (b) a tensioned hinge at a proximal end of the coupling mechanism body, wherein the tensioned hinge is hingedly coupled to the connection port; and
   (c) a coupleable structure at a distal end of the coupling mechanism, wherein the coupleable structure comprises at least one coupling feature configured to be coupleable with a matching coupling feature on the proximal end of the device body and an actuable button.

4. The robotic surgical system of claim 1, wherein the elongate device body comprises a male connector disposed at a proximal end of the elongate device body, wherein the male connector is coupleable with the connection port.

5. The robotic surgical system of claim 1, wherein the camera coupling mechanism comprises:
   (a) a slidable body disposed within the connection port;
   (b) a camera receiving opening defined within the slidable body;
   (c) an actuable camera release button attached to a first end of the slidable body; and
   (d) a tensioned spring operably coupled to a second end of the slidable body.

6. The robotic surgical system of claim 5, wherein the slidable body is slidable along a plane substantially transverse to a longitudinal axis of the elongate device body.

7. The robotic surgical system of claim 1, wherein the first sensing component is a magnet.

8. A removable connection port for a robotic surgical device, the port comprising:
   (a) a connection port body;
   (b) a distal opening defined at a distal end of the port body, wherein the distal opening is sized and shaped to receive a proximal end of an elongate device body;
   (c) a proximal opening defined at a proximal end of the port body, wherein the proximal opening is sized and shaped to receive a camera assembly;
   (d) a seal package disposed in the connection port body, the seal package comprising at least two seals configured to receive a shaft of a camera assembly;
   (e) a device body coupling mechanism disposed within the connection port body, the device body coupling mechanism comprising first and second hinged coupling mechanisms hingedly coupled to the connection port body;
   (f) a camera coupling mechanism disposed within the connection port body, the camera coupling mechanism comprising:
      (i) a slidable body disposed within the connection port body; and
      (ii) a camera receiving opening defined within the slidable body; and
   (g) a presence detection mechanism comprising:
      (i) a rotatable lever operably coupled to the camera coupling mechanism at a pivot point, wherein the rotatable lever rotates around the pivot point; and
      (ii) a first sensing component disposed on the rotatable lever, wherein the first sensing component is configured to interact with a second sensing component disposed on the elongate device body when the removable connection port is coupled to the elongate device body.

9. The removable connection port of claim 8, wherein each of the first and second hinged coupling mechanisms comprises:
   (a) a coupling mechanism body;
   (b) a tensioned hinge at a proximal end of the coupling mechanism body, wherein the tensioned hinge is hingedly coupled to the connection port body; and
   (c) a coupleable structure at a distal end of the coupling mechanism, wherein the coupleable structure comprises at least one coupling feature configured to be coupleable with a matching coupling feature on the proximal end of the elongate device body and an actuable button.

10. The removable connection port of claim 8, wherein the distal opening is sized and shaped to receive a male connector disposed at the proximal end of the elongate device body.

11. The removable connection port of claim 8, wherein the camera coupling mechanism further comprises:
   (a) an actuable camera release button attached to a first end of the slidable body; and (b) a tensioned spring operably coupled to a second end of the slidable body.

12. The removable connection port of claim 8, wherein the slidable body is slidable along a plane substantially transverse to a longitudinal axis of a lumen of the seal package.

13. The removable connection port of claim 8, wherein the first sensing component is a magnet.

14. A robotic surgical system, comprising:
  (a) a robotic surgical device comprising:
    (i) an elongate device body comprising a distal end and a proximal end;
    (ii) a removable connection port disposed at the proximal end of the device body, the connection port comprising:
      (A) a device body coupling mechanism disposed within the connection port, the device body coupling mechanism comprising first and second hinged coupling mechanisms hingedly coupled to the connection port;
      (B) an camera receiving opening defined in a proximal end of the connection port;
      (C) a seal package disposed in the removable connection port, the seal package comprising at least two seals;
      (D) a camera coupling mechanism disposed within the removable connection port, the camera coupling mechanism comprising:
        (1) a slidable body slidably disposed within the connection port;
        (2) a camera receiving opening defined within the slidable body;
        (3) an actuable camera release button attached to a first end of the slidable body; and
        (4) a tensioned spring operably coupled to a second end of the slidable body; and
      (E) a presence detection mechanism operably coupled to the camera coupling mechanism, the presence detection mechanism comprising:
        (1) a rotatable lever operably coupled to the camera coupling mechanism at a pivot point, wherein the rotatable lever rotates around the pivot point;
        (2) a first sensing component disposed on the rotatable lever; and
        (3) a second sensing component disposed on the elongate body, wherein the second sensing component is configured to sense the presence or absence of the first sensing component; and
    (iii) first and second robotic arms operably coupled to the distal end of the device body; and
  (b) a removable camera component removably disposable in the camera receiving opening and through the seal package, the removable camera component comprising a camera body, an elongate camera tube, a flexible section, and a distal imager.

15. The robotic surgical system of claim 14, wherein each of the first and second hinged coupling mechanisms comprises:
  (a) a coupling mechanism body;
  (b) a tensioned hinge at a proximal end of the coupling mechanism body, wherein the tensioned hinge is hingedly coupled to the connection port; and
  (c) a coupleable structure at a distal end of the coupling mechanism, wherein the coupleable structure comprises at least one coupling feature configured to be coupleable with a matching coupling feature on the proximal end of the device body and an actuable button.

16. The robotic surgical system of claim 14, wherein the slidable body is slidable along a plane substantially transverse to a longitudinal axis of a lumen defined by the at least two seals in the seal package.

* * * * *